United States Patent
Finke et al.

(10) Patent No.: US 6,506,777 B1
(45) Date of Patent: Jan. 14, 2003

(54) CYCLOPENTYL MODULATORS OF CHEMOKINE RECEPTOR ACTIVITY

(75) Inventors: Paul E. Finke, Milltown; Jennifer L. Loebach, Westfield; Malcolm Maccoss, Freehold; Sander G. Mills, Scotch Plains, all of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/589,972

(22) Filed: Jun. 8, 2000

Related U.S. Application Data
(60) Provisional application No. 60/138,872, filed on Jun. 11, 1999.

(51) Int. Cl.$^7$ ..................... A61K 31/445; C07D 211/08
(52) U.S. Cl. ....................... 514/329; 514/327; 514/330; 514/331; 514/317; 546/192
(58) Field of Search ................. 546/192; 514/329, 514/330, 331, 317, 327

(56) References Cited

U.S. PATENT DOCUMENTS

| | | |
|---|---|---|
| 4,105,666 A | 8/1978 | Ward |
| 4,246,271 A * | 1/1981 | Cousse et al. |
| 4,281,132 A | 7/1981 | Ward |
| 5,169,844 A | 12/1992 | Commons et al. |
| 5,424,319 A | 6/1995 | Hanson et al. |
| 5,712,279 A | 1/1998 | Biller et al. |
| 5,750,549 A | 5/1998 | Caldwell et al. |
| 5,935,974 A | 8/1999 | Rae et al. |
| 6,054,468 A | 4/2000 | Geerts et al. |

FOREIGN PATENT DOCUMENTS

| | | |
|---|---|---|
| WO | WO 98/25617 | 6/1998 |
| WO | WO 98/31364 | 7/1998 |
| WO | WO 99/04794 | 2/1999 |
| WO | WO 99/09984 | 3/1999 |

OTHER PUBLICATIONS

Chow et al., "Addition Reactions of Aminium Radicals: Oxidative and Non–oxidative Photoaddition of Nitrosoamines to Non–conjugated Polyenes", J. Chem. Soc. Perkin Trans. I, vol. 7, pp. 1419–1428, 1982.*
J.J. Gomez–Reino et al., "Association of Rheumatoid Arthritis with a Functional Chemokine Receptor, CCR5", Arthritis & Rheumatism, vol. 42, No. 5, May 1999, pp. 989–992.*
T. J. Schall, "Biology of the Rantes/sis Cytokine Family", Cytokine, vol. 3, No. 3, May 1991, pp. 165–183.*
P.M. Murphy, "The Molecular Biology of Leukocyte Chenoattractant Receptors", Annual Review of Immunology, vol. 12, 1994, pp. 593–633.*
H. Deng et al., "Identification of a major co–receptor for primary isolates of HIV–1", Nature, vol. 381, Jun. 1996, pp. 661–666.*

R. Horuk, "Molecular properties of the chemokine receptor family", Trends Pharm. Science, vol. 15, 1994, pp. 159–165.*
A. Ben–Baruch et al., "Monocyte Chemotactic Protein–3 (MCP3) Interacts with Multiple Leukocyte Receptors", J. Biol. Chem., vol. 270, No. 38, Sep. 1995, pp. 22123–22128.*
K. Neote et al., "Molecular Cloning, Functional Expression, and Signaling Characteristics of C–C Chemokine Receptor", Cell, vol. 72, Feb. 1993, pp. 415–425.*
C. Combadiere et al., "Cloning and Functional Expression of a Human Eosinophil CC Chemokine Receptor", J. Biol. Chem., vol. 270, No. 27, Jul. 1995, pp. 16491–16494.*
C. A. Power et al., "Molecular Cloning and Functional Expression of a Novel CC Chemokine Receptor cDNA from a Human Basophilic Line", J. Biol. Chem., vol. 270, No. 33, Aug. 1995, pp. 19495–19500.*
M. Samson et al., "Molecular Cloning and Functional Expression of a New Human CC–Chemokine Receptor Gene", Biochemistry, vol. 35, 1996, pp. 3362–3367.*
A. Chaudhuri et al., "Expression of the Duffy Antigen in K562 Cells,", J. Biol. Chem., vol. 269, No. 11, Mar. 1994, pp. 7835–7838.*
H. Kita et al., "Chemokines Active on Eosinophils: Potential Roles in Allergic Inflammation", J. Exp. Med., vol. 183, Jun. 1996, pp. 2421–2426.*
D. Smith et al., "Blocking of HIV–1 Infectivity by a Soluble, Secreted Form of the CD4 Antigen", Science, vol. 238, 1987, pp. 1704–1707.*

(List continued on next page.)

*Primary Examiner*—John Kight
*Assistant Examiner*—Binta Robinson
(74) *Attorney, Agent, or Firm*—Kenneth R. Walton; Melvin Winokur; J. Eric Thies

(57) ABSTRACT

The present invention is directed to compounds of the formula I:

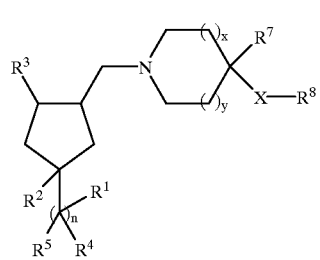

(wherein $R^1$, $R^2$, $R^3$, $R^4$, $R^5$, $R^7$, $R^8$, X, n, x and y are defined herein) which are useful as modulators of chemokine receptor activity. In particular, these compounds are useful as modulators of the chemokine receptors CCR-5 and/or CCR-3.

23 Claims, No Drawings

OTHER PUBLICATIONS

J. A. Levy, "Infection by Human Immunodeficiency Virus–CD4 is not Enough", N. Eng. J. Med., vol. 335, No. 20, Nov. 1996, pp. 1528–1530.*

T. Dragic et al., "HIV–1 entry into CD4+ cells is mediated by chemokine receptor CC–CKR5", Nature, vol. 381, Jun. 1996, pp. 667–673.*

L. Wu et al., "CD4–induced interaction of primary HIV–1 gp120 glycoproteins with the chemokine receptor CCR–5", Nature, vol. 384, Nov. 1996, pp. 179–183.

A. Trkola et al., "CD4–dependent, antibody–sensitive interactions between HIV–1 and its co–receptor CCR–5", Nature, vol. 384, Nov. 1996, pp. 184–187.

M. Samson et al., "Resistence to HIV–1 infection in caucasian individuals bearing mutant alleles of the CCR–5 cehmokine receptor gene", Nature, vol. 382, Aug. 1996, pp. 722–725.

C. M. Hill et al., "Natural resistence to HIV?", Nature, vol. 382, Aug. 1996, pp. 668–669.

Y. Huang et al., "The Role of a mutant CCR5 allele in HIV–1 transmission and disease progression", Nature Medicine, vol. 2, No. 11, Nov. 1996, pp. 1240–1243.

L. Zhang et al., "HIV–1 subtype and second–receptor use", Nature, vol. 383, Oct. 1996, p. 768.

M. Baba et al., "A small–molecule, nonpeptide CCR5 antagonist with highly potent and selective anti HIV–1 activity", Proc. Natl. Acad. Sci., vol. 96, May 1999, pp. 5698–5703.

Chemical Abstracts, 54:4542h, "Syntheses of analgesics–(XXIII) aminocyclopentane derivs.", Yakugaku Zasshi, 79, 1087–91 (1959), Takahashi et. al., vol. 54, 1960.

Ko et al., "Preparation of N–ureidoalkyl–piperidines as modulators of chemokine receptor activity", Chemical Abstracts No. 133:43441, Abstract of WO 00/35449.

* cited by examiner

CYCLOPENTYL MODULATORS OF CHEMOKINE RECEPTOR ACTIVITY

This application claims the benefit of U.S. Provisional Application No. 60/138,872, filed Jun. 11, 1999, the disclosure of which is hereby incorporated by reference in its entirety.

BACKGROUND OF THE INVENTION

Chemokines are chemotactic cytokines that are released by a wide variety of cells to attract macrophages, T cells, eosinophils, basophils and neutrophils to sites of inflammation (reviewed in Schall, *Cytokine*, 3, 165–183 (1991) and Murphy, *Rev. Immun.*, 12, 593–633 (1994)). There are two classes of chemokines, C-X-C ($\alpha$) and C-C ($\beta$), depending on whether the first two cysteines are separated by a single amino acid (C-X-C) or are adjacent (C-C). The $\alpha$-chemokines, such as interleukin-8 (IL-8), neutrophil-activating protein-2 (NAP-2) and melanoma growth stimulatory activity protein (MGSA) are chemotactic primarily for neutrophils, whereas $\beta$-chemokines, such as RANTES, MIP-1$\alpha$, MIP-1$\beta$, monocyte chemotactic protein-1 (MCP-1), MCP-2, MCP-3 and eotaxin are chemotactic for macrophages, T-cells, eosinophils and basophils (Deng, et al., *Nature*, 381, 661–666 (1996)).

The chemokines bind specific cell-surface receptors belonging to the family of G-protein-coupled seven-transmembrane-domain proteins (reviewed in Horuk, *Trends Pharm. Sci.*, 15, 159–165 (1994)) which are termed "chemokine receptors." On binding their cognate ligands, chemokine receptors transduce an intracellular signal though the associated trimeric G protein, resulting in a rapid increase in intracellular calcium concentration. There are at least sixteen human chemokine receptors that bind or respond to $\beta$-chemokines with the following characteristic pattern: CCR-1 (or "CKR-1" or "CC-CKR-1") [MIP-1$\alpha$, MIP-1$\beta$, MCP-3, RANTES] (Ben-Barruch, et al., *J. Biol. Chem.*, 270, 22123–22128 (1995); Beote, et al, *Cell*, 72, 415–425 (1993)); CCR-2A and CCR-2B (or "CKR-2A"/ "CCKR-2A" or "CC-CKR-2A"/"CC-CKR-2A") [MCP-1, MCP-3, MCP-4]; CCR-3 (or "CKR-3" or "CC-CKR-3") [eotaxin, RANTES, MCP-3] (Combadiere, et al., *J. Biol. Chem.*, 270, 16491–16494 (1995); CCR-4 (or "CKR-4" or "CC-CKR-4") [MIP-1$\alpha$, RANTES, MCP-1] (Power, et al., *J. Biol. Chem.*, 270, 19495–19500 (1995)); CCR-5 (or "CKR-5" or "CC-CKR-5") [MIP-1$\alpha$, RANTES, MIP-1$\beta$] (Sanson, et al., *Biochemistry*, 35, 3362–3367 (1996)); and the Duffy blood-group antigen [RANTES, MCP-1] (Chaudhun, et al., *J. Biol. Chem.*, 269, 7835–7838 (1994)). The $\beta$-chemokines include eotaxin, MIP ("macrophage inflammatory protein"), MCP ("monocyte chemoattractant protein") and RANTES ("regulation-upon-activation, normal T expressed and secreted").

Chemokine receptors, such as CCR-1, CCR-2, CCR-2A, CCR-2B, CCR-3, CCR-4, CCR-5, CXCR-3, CXCR-4, have been implicated as being important mediators of inflammatory and immunoregulatory disorders and diseases, including asthma, rhinitis and allergic diseases, as well as autoimmune pathologies such as rheumatoid arthritis and atherosclerosis. A review of the role of chemokines in allergic inflammation is provided by Kita, H., et al., *J. Exp. Med.* 183, 2421–2426 (1996). Accordingly, agents which modulate chemokine receptors would be useful in such disorders and diseases. Compounds which modulate chemokine receptors would be especially useful in the treatment and prevention of atopic conditions including allergic rhinitis, dermatitis, conjunctivitis, and particularly bronchial asthma.

A retrovirus designated human immunodeficiency virus (HIV-1) is the etiological agent of the complex disease that includes progressive destruction of the immune system (acquired immune deficiency syndrome; AIDS) and degeneration of the central and peripheral nervous system. This virus was previously known as LAV, HTLV-III, or ARV.

Certain compounds have been demonstrated to inhibit the replication of HIV, including soluble CD4 protein and synthetic derivatives (Smith, et al., *Science*, 238, 1704–1707 (1987)), dextran sulfate, the dyes Direct Yellow 50, Evans Blue, and certain azo dyes (U.S. Pat. No. 5,468,469). Some of these antiviral agents have been shown to act by blocking the binding of gp120, the coat protein of HIV, to its target, the CD4 glycoprotein of the cell.

Entry of HIV-1 into a target cell requires cell-surface CD4 and additional host cell cofactors. Fusin has been identified as a cofactor required for infection with virus adapted for growth in transformed T-cells, however, fusin does not promote entry of macrophagetropic viruses which are believed to be the key pathogenic strains of HIV in vivo. It has recently been recognized that for efficient entry into target cells, human immunodeficiency viruses require a chemokine receptors, most probably CCR-5 or CXCR-4, as well as the primary receptor CD4 (Levy, *N. Engl. J. Med.*, 335(20), 1528–1530 (Nov. 14, 1996). The principal cofactor for entry mediated by the envelope glycoproteins of primary macrophage-trophic strains of HIV-1 is CCR5, a receptor for the $\beta$-chemokines RANTES, MIP-1$\alpha$ and MIP-1$\beta$ (Deng, et al., *Nature*, 381, 661–666 (1996)). HIV attaches to the CD4 molecule on cells through a region of its envelope protein, gp120. It is believed that the CD-4 binding site on the gp120 of HIV interacts with the CD4 molecule on the cell surface, and undergoes conformational changes which allow it to bind to another cell-surface receptor, such as CCR5 and/or CXCR-4. This brings the viral envelope closer to the cell surface and allows interaction between gp41 on the viral envelope and a fusion domain on the cell surface, fusion with the cell membrane, and entry of the viral core into the cell. It has been shown that $\beta$-chemokine ligands prevent HIV-1 from fusing with the cell (Dragic, et al., *Nature*, 381, 667–673 (1996)). It has further been demonstrated that a complex of gp120 and soluble CD4 interacts specifically with CCR-5 and inhibits the binding of the natural CCR-5 ligands MIP-1$\alpha$ and MIP-1$\beta$ (Wu, et al., *Nature*, 384, 179–183 (1996); Trkola, et al., *Nature*, 384, 184–187 (1996)).

Humans who are homozygous for mutant CCR-5 receptors which do not serve as co-receptors for HIV-1 in vitro appear to be unusually resistant to HIV-1 infection and are not immuno-compromised by the presence of this genetic variant (*Nature*, 382, 722–725 (1996)). Absence of CCR-5 appears to confer substantial protection from HIV-1 infection (*Nature*, 382, 668–669 (1996)). Other chemokine receptors may be used by some strains of HIV-1 or may be favored by non-sexual routes of transmission. Although most HIV-1 isolates studied to date utilize CCR-5 or fusin, some can use both as well as the related CCR-2B and CCR-3 as co-receptors (*Nature Medicine*, 2(11), 1240–1243 (1996)). Nevertheless, drugs targeting chemokine receptors may not be unduly compromised by the genetic diversity of HIV-1 (Zhang, et al., *Nature*, 383, 768 (1996)). Accordingly, an agent which could block chemokine receptors in humans who possess normal chemokine receptors should prevent infection in healthy individuals and slow or halt viral progression in infected patients. By focusing on the host's cellular immune response to HIV infection, better therapies towards all subtypes of HIV may be provided. These results indicate that inhibition of chemokine receptors presents a viable method for the prevention or treatment of infection by HIV and the prevention or treatment of AIDS.

The peptides eotaxin, RANTES, MIP-1α, MIP-1β, MCP-1, and MCP-3 are known to bind to chemokine receptors. As noted above, the inhibitors of HIV-1 replication present in supernatants of CD8+ T cells have been characterized as the β-chemokines RANTES, MIP-1α and MIP-1β.

SUMMARY OF THE INVENTION

The present invention is directed to compounds which inhibit the entry of human immunodeficiency virus (HIV) into target cells and are of value in the prevention of infection by HIV, the treatment of infection by HIV and the prevention and/or treatment of the resulting acquired immune deficiency syndrome (AIDS). The present invention also relates to pharmaceutical compositions containing the compounds and to a method of use of the present compounds and other agents for the prevention and treatment of AIDS and viral infection by HIV.

The present invention is further directed to compounds which are modulators of chemokine receptor activity and are useful in the prevention or treatment of certain inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis. The invention is also directed to pharmaceutical compositions comprising these compounds and the use of these compounds and compositions in the prevention or treatment of such diseases in which chemokine receptors are involved.

DETAILED DESCRIPTION OF THE INVENTION

The present invention is directed to compounds of formula I:

I wherein:

X is —($C_{0-2}$ alkyl)—Y—($C_{0-6}$ alkyl)—,
  where the alkyl is unsubstituted or substituted with 1–7 substituents where the substituents are independently selected from:
    (a) halo,
    (b) hydroxy,
    (c) —O—$C_{1-3}$ alkyl, and
    (d) trifluoromethyl,
  where Y is selected from: —(CO)—, —(CO)O—, —O(CO)—, —(CO)$NR^9$—, —$NR^9$(CO)—, —O(CO)$NR^9$—, —$NR^9$(CO)O—, and —$NR^9$(CO)$NR^{10}$—,
  where $R^9$ is independently selected from: hydrogen, $C_{1-10}$ alkyl, $C_{3-6}$ cycloalkyl, $C_{1-6}$ alkyl-$C_{3-6}$ cycloalkyl, $C_{2-10}$ alkenyl, $C_{2-10}$ alkynyl, benzyl or phenyl, which is unsubstituted or substituted with 1–3 substituents where the substituents are independently selected from: halo, $C_{1-3}$ alkyl, $C_{1-3}$ alkoxy and trifluoromethyl,
  and where $R^{10}$ is independently selected from: hydrogen, $C_{1-6}$ alkyl, benzyl, or phenyl, which is unsubstituted or substituted with 1–3 substituents where the substituents are independently selected from: halo, $C_{1-3}$ alkyl, $C_{1-3}$ alkoxy and trifluoromethyl,
  or where $R^9$ and $R^{10}$ may be joined together to form a 5–8 membered ring which may be unsubstituted or substituted with halo, $C_{1-3}$ alkyl, and $C_{1-3}$ alkoxy;

$R^1$ is selected from:
  (1) —$CO_2H$,
  (2) —$NO_2$,
  (3) —tetrazolyl,
  (4) —hydroxyisoxazole,
  (5) —$SO_2$NHCO—($C_{0-3}$ alkyl)—$R^9$, and
  (6) —P(O)(OH)$_2$;

$R^2$ is selected from:
  (1) hydrogen, and
  (2) hydroxy;

$R^3$ is selected from the group consisting of:
  phenyl and heterocycle, which is unsubstituted or substituted with 1–7 substituents where the substituents are independently selected from:
    (a) halo,
    (b) trifluoromethyl,
    (c) hydroxy,
    (d) $C_{1-3}$ alkyl,
    (e) —O—$C_{1-3}$ alkyl,
    (f) —$CO_2R^9$,
    (g) —$NR^9R^{10}$, and
    (h) —$CONR^9R^{10}$;

$R^4$ and $R^5$ are independently selected from:
  hydrogen, hydroxy, fluoro, $C_{1-10}$ alkyl, $C_{3-8}$ cycloalkyl, $C_{2-10}$ alkenyl, $C_{2-10}$ alkynyl, phenyl, —($C_{1-6}$ alkyl)-phenyl, —($C_{1-6}$ alkyl)—$C_{3-8}$ cycloalkyl, naphthyl, biphenyl, and heterocycle, which is unsubstituted or substituted with 1–7 of $R^{11}$ where $R^{11}$ is independently selected from:
    (a) halo,
    (b) trifluoromethyl,
    (c) hydroxy,
    (d) $C_{1-3}$ alkyl,
    (e) —O—$C_{1-3}$ alkyl,
    (f) —$CO_2R^9$, and
    (g) —$CONR^9R^{10}$,
  or where $R^4$ and $R^5$ may be joined together to form a 3–8 membered saturated ring which may be unsubstituted or substituted with 1–7 of $R^{11}$, or where, if n is 1, $R^2$ and $R^4$ may be joined together to form a double bond;

$R^7$ is selected from:
  (1) hydrogen,
  (2) $C_{1-6}$ alkyl, which is unsubstituted or substituted with 1–4 substituents where the substituents are independently selected from: hydroxy, cyano, and halo,
  (3) hydroxy, and
  (4) halo;

$R^8$ is selected from:
  hydrogen, phenyl, naphthyl, biphenyl, and heterocycle, which is unsubstituted or substituted with 1–7 of $R^{12}$ where $R^{12}$ is independently selected from:

(a) halo,
(b) cyano,
(c) hydroxy,
(d) $C_{1-6}$ alkyl, which is unsubstituted or substituted with 1–5 of $R^{13}$ where $R^{13}$ is independently selected from: halo, cyano, hydroxy, $C_{1-6}$ alkoxy, —$CO_2H$, —$CO_2(C_{1-6}$ alkyl), phenyl, trifluoromethyl, and —$NR^9R^{10}$,
(e) —O—$C_{1-6}$ alkyl, which is unsubstituted or substituted with 1–5 of $R^{13}$,
(f) —$CF_3$,
(g) —$CHF_2$,
(h) —$CH_2F$,
(i) —$NO_2$,
(j) phenyl,
(k) —$CO_2R^9$,
(l) tetrazolyl,
(m) —$NR^9R^{10}$,
(n) —$NR^9$—$COR^{10}$,
(o) —$NR^9$—$CO_2R^{10}$,
(p) —CO—$NR^9R^{10}$,
(q) —OCO—$NR^9R^{10}$,
(r) —$NR^9CO$—$NR^9R^{10}$,
(s) —$S(O)_m$—$R^9$, wherein m is an integer selected from 0, 1 and 2,
(t) —$S(O)_2$—$NR^9R^{10}$,
(u) —$NR^9S(O)_2$—$R^{10}$, and
(v) —$NR^9S(O)_2$—$NR^9R^{10}$;

n is an integer selected from 1, 2, 3 and 4;

x is an integer selected from 0, 1 and 2, and y is an integer selected from 0, 1 and 2, with the proviso that the sum of x and y is 2;

and pharmaceutically acceptable salts thereof and individual diastereomers thereof.

One one embodiment of the present invention is a compound of Formula I, wherein $R^1$ is selected from:
(1) —$CO_2H$,
(2) —$NO_2$,
(3) —tetrazolyl,
(4) —hydroxyisoxazole, and
(5) —$P(O)(OH)_2$;

and all other variables are as previously defined;
and pharmaceutically acceptable salts thereof and individual diastereomers thereof.

Preferred compounds of the present invention include those of formula Ia:

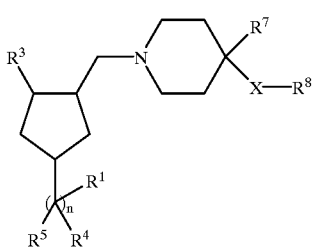

Ia wherein $R^1$, $R^3$, $R^4$, $R^5$, $R^7$, $R^8$, X and n are defined herein; and pharmaceutically acceptable salts and individual diastereomers thereof.

More preferred compounds of the present invention include those of formula Ic:

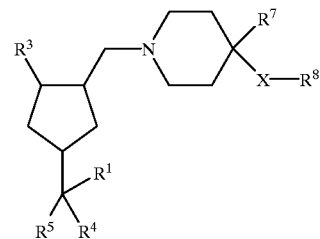

Ic wherein $R^1$, $R^3$, $R^4$, $R^5$, $R^7$, $R^8$ and X are defined herein; and pharmaceutically acceptable salts and individual diastereomers thereof.

Highly preferred compounds of the present invention include those of formula Id:

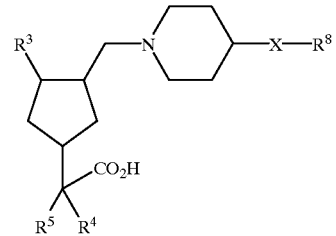

Id wherein $R^3$, $R^4$, $R^5$, $R^8$ and X are defined herein; and pharmaceutically acceptable salts and individual diastereomers thereof.

More highly preferred compounds of the present invention include those of formula Ie:

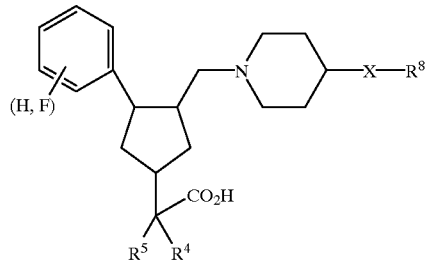

Ie wherein $R^4$, $R^5$, $R^8$ and X are defined herein; and pharmaceutically acceptable salts and individual diastereomers thereof.

In the present invention it is preferred that $R^1$ is selected from:
(1) —$CO_2H$,
(2) —$P(O)(OH)_2$, and
(3) —tetrazolyl.

In the present invention it is more preferred that $R^1$ is selected from:
(1) —$CO_2H$, and
(2) —tetrazolyl.

In the present invention it is even more preferred that $R^1$ is —$CO_2H$.

In the present invention it is preferred that $R^3$ is selected from the group consisting of:

phenyl and thienyl, which may be unsubstituted or substituted with 1–5 substituents where the substituents are independently selected from:

(a) halo,
(b) trifluoromethyl,
(c) hydroxy,
(d) $C_{1-3}$ alkyl, and
(e) —O—$C_{1-3}$ alkyl.

In the present invention it is more preferred that $R^3$ is selected from the group consisting of:
  phenyl and thienyl, which may be unsubstituted or substituted with 1–5 substituents where the substituents are independently selected from:
    (a) fluoro,
    (b) chloro,
    (c) trifluoromethyl,
    (d) hydroxy, and
    (e) $C_{1-3}$ alkyl.

In the present invention it is even more preferred that $R^3$ is selected from the group consisting of:
  phenyl, which may be unsubstituted or substituted with 1–5 substituents where the substituents are independently selected from:
    (a) fluoro, and
    (b) chloro; and unsubstituted thienyl.

In the present invention it is still more preferred that $R^3$ is unsubstituted phenyl, (3-fluoro)phenyl or 3-thienyl.

In the present invention it is preferred that $R^2$ is hydrogen.

In the present invention it is preferred that $R^4$ is hydrogen or $C_{1-6}$ alkyl.

In the present invention it is more preferred that $R^4$ is hydrogen or methyl.

In the present invention it is preferred that $R^5$ is selected from: hydrogen, $C_{1-6}$ alkyl, $C_{3-8}$ cycloalkyl, —$CH_2$—$C_{3-8}$ cycloalkyl, and phenyl.

In the present invention it is more preferred that $R^5$ is selected from: hydrogen, methyl, n-propyl, isopropyl, n-butyl, isobutyl, secbutyl, cyclohexyl, —$CH_2$-cyclopropyl, —$CH_2$-cyclobutyl and phenyl.

In the present invention it is preferred that $R^4$ and $R^5$ are joined together to form a $C_{3-8}$ cycloalkyl ring.

In the present invention it is also preferred that $R^4$ and $R^2$ are joined together to form a double bond.

In the present invention it is preferred that $R^7$ is hydrogen, fluoro, hydroxy or $C_{1-6}$ alkyl.

In the present invention it is more preferred that $R^7$ is hydrogen or fluoro.

In the present invention it is even more preferred that $R^7$ is hydrogen.

In the present invention it is preferred that X is: —($C_{0-2}$ alkyl)—Y—($C_{0-4}$ alkyl)—,
  where the alkyl is unsubstituted or substituted with 1–7 substituents where the substituents are independently selected from:
    (a) halo,
    (b) hydroxy,
    (c) —O—$C_{1-3}$ alkyl, and
    (d) trifluoromethyl,
  where Y is selected from:
    —(CO)$NR^9$—, —$NR^9$(CO)—, —O(CO)$NR^9$—, —$NR^9$(CO)O—, and —$NR^9$(CO)$NR^{10}$—,
  where $R^9$ is independently selected from: hydrogen, $C_{1-10}$ alkyl, $C_{3-6}$ cycloalkyl, $C_{1-6}$ alkyl-$C_{3-6}$ cycloalkyl, $C_{2-10}$ alkenyl, $C_{2-10}$ alkynyl, benzyl or phenyl, which is unsubstituted or substituted with 1–3 substituents where the substituents are independently selected from: halo, $C_{1-3}$ alkyl, $C_{1-3}$ alkoxy and trifluoromethyl,
  and where $R^{10}$ is independently selected from: hydrogen, $C_{1-6}$ alkyl, benzyl, or phenyl, which is unsubstituted or substituted with 1–3 substituents where the substituents are independently selected from: halo, $C_{1-3}$ alkyl, $C_{1-3}$ alkoxy and trifluoromethyl,
  or where $R^9$ and $R^{10}$ may be joined together to form a 5–8 membered ring which is unsubstituted.

In the present invention it is more preferred that X is:
—Y—($CO_4$ alkyl)—,
  where the alkyl is unsubstituted,
  where Y is selected from: —O(CO)$NR^9$—, —$NR^9$(CO)O—, and —$NR^9$(CO)$NR^{10}$—,
  where $R^9$ is independently selected from: hydrogen, $C_{1-10}$ alkyl, $C_{2-10}$ alkenyl, and $C_{1-6}$ alkyl-$C_{3-6}$ cycloalkyl,
  where $R^{10}$ is independently selected from: hydrogen and $C_{1-6}$ alkyl,
  or where $R^9$ and $R^{10}$ may be joined together to form a 5–8 membered ring which is unsubstituted.

In the present invention it is even more preferred that X is selected from:
  —O(CO)$NR^9$—, —O(CO)$NR^9CH_2$—, —$NR^9$(CO)O—, —$NR^9$(CO)$OCH_2$—, —$NR^9$(CO)$NR^{10}$—, and —$NR^9$(CO)$NR^{10}CH_2$—,
  where $R^9$ is independently selected from: hydrogen, $C_{1-10}$ alkyl, $C_{2-10}$ alkenyl, and $C_{1-6}$ alkyl-$C_{3-6}$ cycloalkyl,
  where $R^{10}$ is independently selected from: hydrogen and $C_{1-6}$ alkyl,
  or where $R^9$ and $R^{10}$ may be joined together to form a 5–8 membered ring which is unsubstituted.

In an aspect of the preceding embodiment, in the present invention it is even more preferred that X is selected from:
  —O(CO)$NR^9$—, —$NR^9$(CO)O—, and —$NR^9$(CO)$NR^{10}$—,
  where $R^9$ is independently selected from: hydrogen, $C_{1-10}$ alkyl, $C_{2-10}$ alkenyl, and $C_{1-6}$ alkyl-$C_{3-6}$ cycloalkyl,
  where $R^{10}$ is independently selected from: hydrogen and $C_{1-6}$ alkyl,
  or where $R^9$ and $R^{10}$ may be joined together to form a 5–8 membered ring which is unsubstituted.

In the present invention it is still more preferred that X is selected from:
  —$NR^9$(CO)O—, —$NR^9$(CO)$OCH_2$—, —$NR^9$(CO)NH—, and —$NR^9$(CO)$NHCH_2$—,
  where $R^9$ is independently selected from: methyl, ethyl, n-propyl, allyl, and —$CH_2$-cyclopropyl.

In an aspect of the preceding embodiment, in the present invention it is still more preferred that X is selected from:
  —$NR^9$(CO)O—, and —$NR^9$(CO)NH—,
  where $R^9$ is independently selected from: methyl, ethyl, n-propyl, allyl, and —$CH_2$-cyclopropyl.

In the present invention it is preferred that $R^8$ is hydrogen or phenyl, which is unsubstituted or substituted with 1–7 substituents where the substituents are independently selected from:
  (a) halo,
  (b) cyano,
  (c) hydroxy,
  (d) $C_{1-6}$ alkyl, which is unsubstituted or substituted with 1–5 of $R^{13}$ where $R^{13}$ is independently selected from: halo, cyano, hydroxy, $C_{1-6}$ alkoxy, —$CO_2H$, phenyl, —$CO_2(C_{1-6}$ alkyl), trifluoromethyl, and —$NR^9R^{10}$, wherein $R^9$ and $R^{10}$ are independently selected from: hydrogen, $C_{1-6}$ alkyl, $C_{5-6}$ cycloalkyl, benzyl or phenyl, which is unsubstituted or substituted with 1–3 substituents where the substituents are independently selected from: halo, $C_{1-3}$ alkyl, $C_{1-3}$ alkoxy and trifluoromethyl;

(e) —O—$C_{1-6}$ alkyl, which is unsubstituted or substituted with 1–5 of $R^{13}$, (f) —$CF_3$, (g) —$CHF_2$, (h) —$CH_2F$, (i) —$NO_2$, (j) phenyl, (k) —$CO_2R^9$, (l) tetrazolyl, (m) —$NR^9R^{10}$, (n) —$NR^9$—$COR^{10}$, (o) —$NR^9$—$CO_2R^{10}$, (p) —CO—$NR^9R^{10}$, (q) —OCO—$NR^9R^{10}$, (r) —$NR^9CO$—$NR^9R^{10}$, (s) —$S(O)_m$—$R^9$, wherein m is an integer selected from 0, 1 and 2, (t) —$S(O)_2$—$NR^9R^{10}$, (u) —$NR^9S(O)_2$—$R^{10}$, and (v) —$NR^9S(O)_2$—$NR^9R^{10}$.

In the present invention it is more preferred that $R^8$ is phenyl which is unsubstituted or substituted with 1–5 substituents where the substituents are independently selected from:

(a) halo, (b) cyano, (c) —$NO_2$, (d) —$CF_3$, (e) —$CHF_2$, (f) —$CH_2F$, (g) tetrazolyl, (h) $C_{1-6}$ alkyl, which is unsubstituted or substituted with phenyl, and (i) —O—$C_{1-6}$ alkyl.

In the present invention it is even more preferred that $R^8$ is phenyl, which is unsubstituted or substituted with 1–3 substituents where the substituents are independently selected from:

(a) fluoro, (b) chloro, (c) cyano, (d) —$NO_2$, (e) $C_{1-6}$ alkyl, which is unsubstituted or substituted with phenyl, and (f) —$CF_3$.

In the present invention it is still more preferred that $R^8$ is selected from: phenyl, 4-chlorophenyl, 2-fluorophenyl, 3-fluorophenyl, 4-fluorophenyl, 2,4-difluorophenyl, 3,4-difluorophenyl, 3,5-difluorophenyl, 4-methylphenyl, 3-nitrophenyl, 4-nitrophenyl, and 4-trifluoromethylphenyl.

In the present invention it is preferred that n is an integer selected from 1, 2 and 3.

In the present invention it is more preferred that n is an integer which is 1.

In the present invention it is preferred that x is an integer which is 1 and y is an integer which is 1.

It is to be understood that embodiments of the present invention include, but are not limited to, compounds of formula I wherein $R^1$, $R^2$, $R^3$, $R^4$, $R^5$, $R^7$, $R^8$, X, n, x, and y are defined in accordance with one of the embodiments or aspects thereof as set forth above. Any and all possible combinations of preferred, more preferred, even more preferred, highly preferred, more highly preferred, and most preferred definitions of these variables in formulas I are within the scope of the present invention.

The compounds of the instant invention have at least two asymmetric centers at the ring junction of the substitutents bearing the piperidine and $R^3$. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The relative configurations of the more preferred compounds of this invention are of the trans orientation, i.e. as depicted:

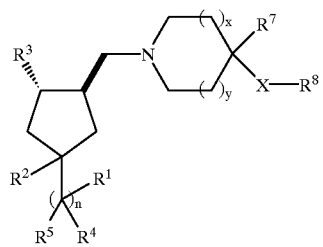

or

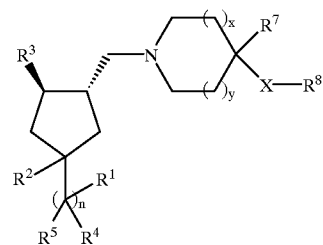

The relative configurations of the even more preferred compounds of this invention with respect to the configuration at the 1-position of the cyclopentane ring is 1,3-trans of the orientation as depicted:

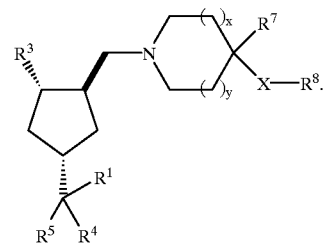

The relative configurations of the most preferred compounds of this invention with respect to the configuration at the 1-position of the cyclopentane ring is 1,3-trans and with the (S)-stereochemistry at the 1,1'-position of the orientation as depicted:

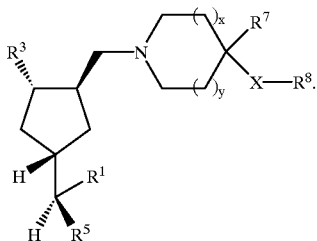

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

As appreciated by those of skill in the art, halo or halogen as used herein are intended to include chloro, fluoro, bromo and iodo. Similarly, $C_{1-8}$, as in $C_{1-8}$ alkyl is defined to identify the group as having 1, 2, 3, 4, 5, 6, 7 or 8 carbons in a linear or branched arrangement, such that $C_{1-8}$ alkyl specifically includes methyl, ethyl, propyl, butyl, pentyl, hexyl, heptyl and octyl. Likewise, $C_0$, as in $C_0$ alkyl is defined to identify the presence of a direct covalent bond.

The term "heterocycle" (which may alternatively be referred to as "heterocyclic") refers to a 4- to 8-membered monocyclic ring, a 7- to 11-membered bicyclic system, or a 10 to 15-membered tricyclic ring system, any ring of which is saturated or unsaturated (partially or totally), and which consists of carbon atoms and one or more heteroatoms (e.g., from 1 to 4 heteroatoms) selected from N, O and S, and wherein the nitrogen and sulfur heteroatoms may optionally be oxidized, the nitrogen heteroatom may optionally be quaternized, and a ring carbon may optionally be oxidized (i.e., is substituted with oxo). The heterocyclic ring may be attached at any heteroatom or carbon atom, provided that attachment results in the creation of a stable structure. A preferred heterocycle is a 4- to 8-membered monocyclic ring or a 7- to 11-membered bicyclic system, as defined and described above.

The term "heterocycle" as used herein is intended to include the following groups: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof.

The term "heterocycle" as used herein is also intended to include, but is not limited to, the following groups: methylenedioxyphenyl, imidazopyridyl, imidazopyrimidinyl, imidazopyridazinyl, imidazopyrazinyl, imidazotriazinyl, imidazothiopheyl, pyrazolopyddyl, pyrazolopyrimidinyl, pyrazolopyridazinyl, pyrazolopyrazinyl, pyrazolotriazinyl, pyrazolothiophenyl, triazolopyridyl, triazolopyrimidinyl, triazolopyridazinyl, triazolopyrazinyl, triazolothiophenyl, tetrahydroimidazopyridinyl, tetrahydropyrazolopyridinyl, tetrahydrotriazopyridinyl, tetrahydrotriazolopyridazinyl, and tetrahydroindazolyl.

The term "heterocycle" as used herein is also intended to include, but is not limited to, the following groups: tetrahydroimidazopyrimidyl, tetrahydroimidazopyrazinyl, tetrahydroimidazopyridazinyl, tetrahydrotriazolopyrimidyl, tetrahydrotriazolopyrazinyl, tetrahydropyrazolopyrimidyl, tetrahydropyrazolopyrazinyl, imidazothiazolyl, and imidazothiadiazolyl.

The term "heterocycle" as used herein is also intended to include, but is not limited to, oxopyridinyl (e.g., 2-oxopyridinyl), oxopiperidinyl, and oxopyrazolyl.

The terms "thiophenyl" and "thienyl" have the same meaning herein and are used interchangeably. Similarly, the following pairs of terms are used interchangeably: "indazolyl" and "benzopyrazolyl"; "pyridinyl" and "pyridyl".

In the expression ". . . which is unsubstituted or substituted with . . . ", "which" is intended to refer back to all preceding chemical groups in the particular definition in which the expression appears, unless a contrary meaning is expressed or is implied by the context. Furthermore, the term "substituted" in the expression includes mono- and poly-substitution by a named substituent to the extent such single and multiple substitution is chemically allowed in any of the named chemical groups. Thus, for example, the expression "is independently selected from: hydrogen, $C_{1-6}$ alkyl, $C_{5-6}$ cycloalkyl, benzyl or phenyl, which is unsubstituted or substituted with 1–3 substituents . . . ", encompasses hydrogen, $C_{1-6}$ alkyl, $C_{5-6}$ cycloalkyl, benzyl, phenyl, mono- and di- and tri-substituted $C_{1-6}$ alkyl, mono- and di- and tri-substituted $C_{5-6}$ cycloalkyl, mono- and di- and tri-substituted benzyl and mono- and di- and tri-substituted phenyl.

Exemplifying the invention is the use of the compounds disclosed in the Examples and herein.

Specific compounds within the present invention include a compound which is selected from the group consisting of:

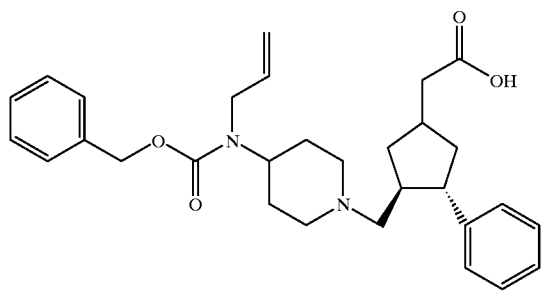

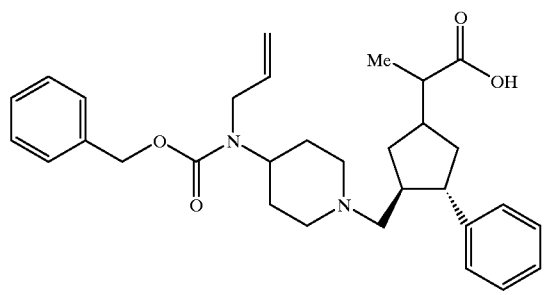
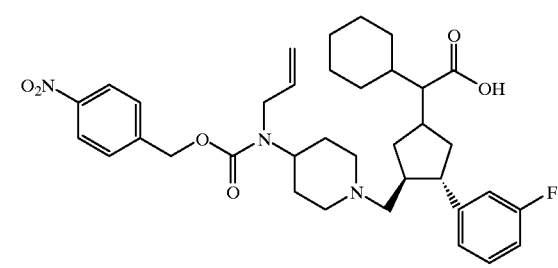
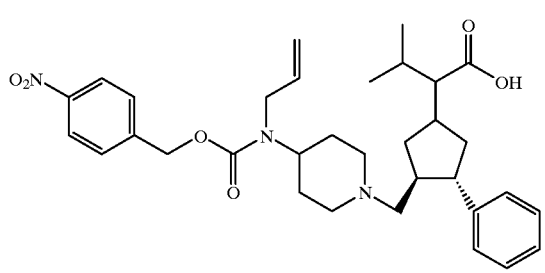
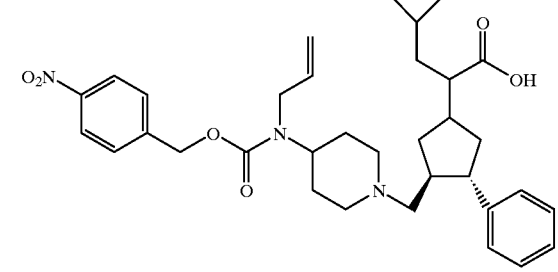
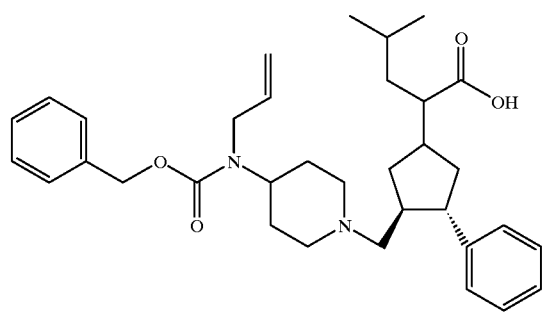
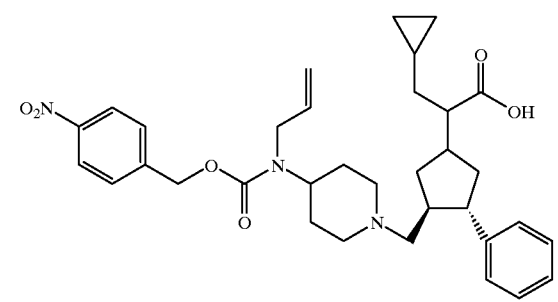
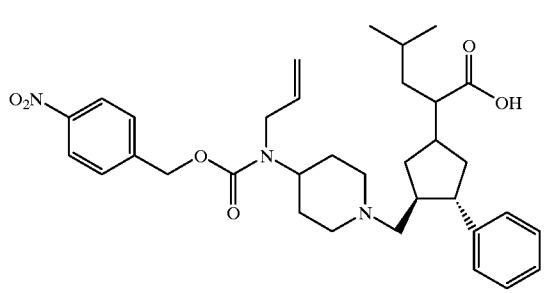
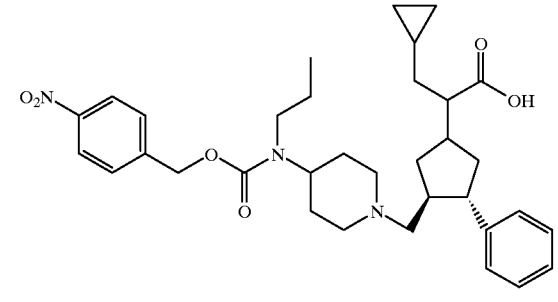
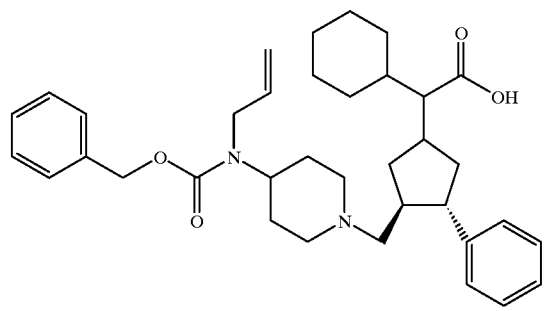

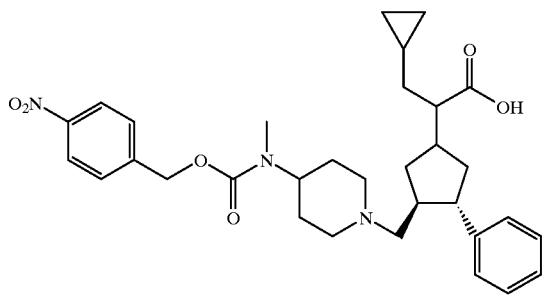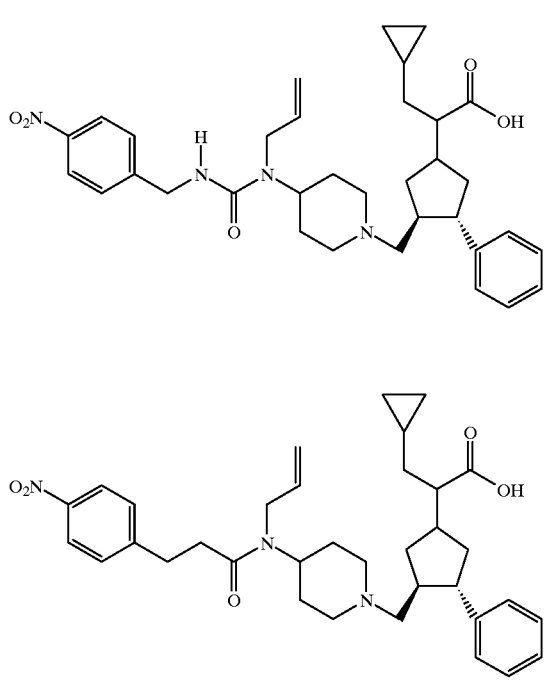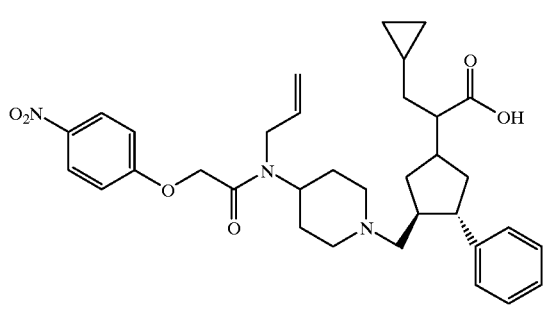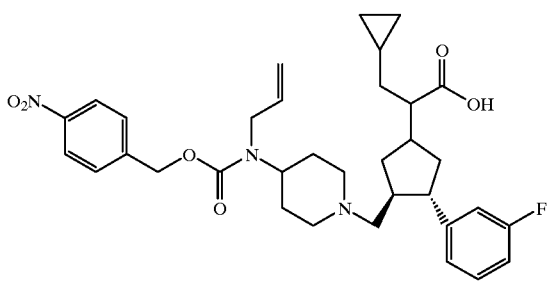

and pharmaceutically acceptable salts thereof and individual diastereomers thereof.

The subject compounds are useful in a method of modulating chemokine receptor activity in a patient in need of such modulation comprising the administration of an effective amount of the compound.

The present invention is directed to the use of the foregoing compounds as modulators of chemokine receptor activity. In particular, these compounds are useful as modulators of the chemokine receptors, including CCR-5 and/or CCR-3.

The utility of the compounds in accordance with the present invention as modulators of chemokine receptor activity may be demonstrated by methodology known in the art, such as the assay for chemokine binding as disclosed by Van Riper, et al., *J. Exp. Med.*, 177, 851–856 (1993) which may be readily adapted for measurement of CCR-5 binding, and the assay for CCR-3 binding as disclosed by Daugherty, et al., *J. Exp. Med.*, 183, 2349–2354 (1996). Cell lines for expressing the receptor of interest include those naturally expressing the receptor, such as EOL-3 or THP-1, or a cell engineered to express a recombinant receptor, such as CHO, RBL-2H3, HEK-293. For example, a CCR3 transfected AML14.3D10 cell line has been placed on restricted deposit with American Type Culture Collection in Rockville, Md. as ATCC No. CRL-12079, on Apr. 5, 1996. The utility of the compounds in accordance with the present invention as inhibitors of the spread of HIV infection in cells may be demonstrated by methodology known in the art, such as the HIV quantitation assay disclosed by Nunberg, et al., *J. Virology*, 65 (9), 4887–4892 (1991).

In particular, the compounds of the following examples had activity in binding to the CCR-5 or the CCR-3 receptor in the aforementioned assays, generally with an $IC_{50}$ of less than about 1 μM. Such a result is indicative of the intrinsic activity of the compounds in use as modulators of chemokine receptor activity.

Mammalian chemokine receptors provide a target for interfering with or promoting eosinophil and/or lymphocyte function in a mammal, such as a human. Compounds which inhibit or promote chemokine receptor function, are particularly useful for modulating eosinophil and/or lymphocyte function for therapeutic purposes. Accordingly, the present invention is directed to compounds which are useful in the prevention and/or treatment of a wide variety of inflammatory and immunoregulatory disorders and diseases, allergic diseases, atopic conditions including allergic rhinitis, dermatitis, conjunctivitis, and asthma, as well as autoimmune pathologies such as rheumatoid arthritis and atherosclerosis.

For example, an instant compound which inhibits one or more functions of a mammalian chemokine receptor (e.g., a human chemokine receptor) may be administered to inhibit (i.e., reduce or prevent) inflammation. As a result, one or more inflammatory processes, such as leukocyte emigration, chemotaxis, exocytosis (e.g., of enzymes, histamine) or inflammatory mediator release, is inhibited. For example, eosinophilic infiltration to inflammatory sites (e.g., in asthma) can be inhibited according to the present method.

Similarly, an instant compound which promotes one or more functions of a mammalian chemokine receptor (e.g., a human chemokine) is administered to stimulate (induce or enhance) an inflammatory response, such as leukocyte emigration, chemotaxis, exocytosis (e.g., of enzymes, histamine) or inflammatory mediator release, resulting in the beneficial stimulation of inflammatory processes. For example, eosinophils can be recruited to combat parasitic infections.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

Diseases and conditions associated with inflammation and infection can be treated using the method of the present invention. In a preferred embodiment, the disease or condition is one in which the actions of eosinophils and/or lymphocytes are to be inhibited or promoted, in order to modulate the inflammatory response.

Diseases or conditions of humans or other species which can be treated with inhibitors of chemokine receptor function, include, but are not limited to: inflammatory or allergic diseases and conditions, including respiratory allergic diseases such as asthma, particularly bronchial asthma, allergic rhinitis, hypersensitivity lung diseases, hypersensitivity pneumonitis, eosinophilic pneumonias (e.g., Loeffler's syndrome, chronic eosinophilic pneumonia), delayed-type hypersensitivity, interstitial lung diseases (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis); systemic anaphylaxis or hypersensitivity responses, drug allergies (e.g., to penicillin, cephalosporins), insect sting allergies; autoimmune diseases, such as rheumatoid arthritis, psoriatic arthritis, multiple sclerosis, systemic lupus erythematosus, myasthenia gravis, juvenile onset diabetes; glomerulonephritis, autoimmune thyroiditis, Behcet's disease; graft rejection (e.g., in transplantation), including allograft rejection or graft-versus-host disease; inflammatory bowel diseases, such as Crohn's disease and ulcerative colitis; spondyloarthropathies; scleroderma; psoriasis (including T-cell mediated psoriasis) and inflammatory dermatoses such an dermatitis, eczema, atopic dermatitis, allergic contact dermatitis, urticaria; vasculitis (e.g., necrotizing, cutaneous, and hypersensitivity vasculitis); eosinphilic myositis, eosinophilic fasciitis; cancers with leukocyte infiltration of the skin or organs. Other diseases or conditions in which undesirable inflammatory responses are to be inhibited can be treated, including, but not limited to, reperfusion injury, atherosclerosis, certain hematologic malignancies, cytokine-induced toxicity (e.g., septic shock, endotoxic shock), polymyositis, dermatomyositis.

Diseases or conditions of humans or other species which can be treated with promoters of chemokine receptor function, include, but are not limited to: immunosuppression, such as that in individuals with immunodeficiency syndromes such as AIDS, individuals undergoing radiation therapy, chemotherapy, therapy for autoimmune disease or other drug therapy (e.g., corticosteroid therapy), which causes immunosuppression; immunosuppression due congenital deficiency in receptor function or other causes; and infectious diseases, such as parasitic diseases, including, but not limited to helminth infections, such as nematodes (round worms); (Trichuriasis, Enterobiasis, Ascariasis, Hookworm, Strongyloidiasis, Trichinosis, filariasis); trematodes (flukes) (Schistosomiasis, Clonorchiasis), cestodes (tape worms) (Echinococcosis, Taeniasis saginata, Cysticercosis); visceral worms, visceral larva migrans (e.g., Toxocara), eosinophilic gastroenteritis (e.g., Anisaki spp., Phocanema ssp.), cutaneous larva migrans (*Ancylostona braziliense, Ancylostoma caninum*).

The compounds of the present invention are accordingly useful in the prevention and treatment of a wide variety of inflammatory and immunoregulatory disorders and diseases, allergic conditions, atopic conditions, as well as autoimmune pathologies.

In another aspect, the instant invention may be used to evaluate putative specific agonists or antagonists of chemokine receptors, including CCR-5 and/or CCR-3. Accordingly, the present invention is directed to the use of these compounds in the preparation and execution of screening assays for compounds which modulate the activity of chemokine receptors. For example, the compounds of this invention are useful for isolating receptor mutants, which are excellent screening tools for more potent compounds. Furthermore, the compounds of this invention are useful in establishing or determining the binding site of other compounds to chemokine receptors, e.g., by competitive inhibition. The compounds of the instant invention are also useful for the evaluation of putative specific modulators of the chemokine receptors, including CCR-5 and/or CCR-3. As appreciated in the art, thorough evaluation of specific agonists and antagonists of the above chemokine receptors has been hampered by the lack of availability of non-peptidyl (metabolically resistant) compounds with high binding affinity for these receptors. Thus the compounds of this invention are commercial products to be sold for these purposes.

The present invention is further directed to a method for the manufacture of a medicament for modulating chemokine receptor activity in humans and animals comprising combining a compound of the present invention with a pharmaceutical carrier or diluent.

The present invention is further directed to the use of these compounds in the prevention or treatment of infection by a retrovirus, in particular, the human immunodeficiency virus (HIV) and the treatment of, and delaying of the onset of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compounds of this invention are useful in treating infection by HIV after suspected past exposure to HIV by, e.g., blood transfusion, organ transplant, exchange of body fluids, bites, accidental needle stick, or exposure to patient blood during surgery.

In a preferred aspect of the present invention, a subject compound may be used in a method of inhibiting the binding of a chemokine to a chemokine receptor, such as CCR-5 or CCR-3, of a target cell, which comprises contacting the target cell with an amount of the compound which is effective at inhibiting the binding of the chemokine to the chemokine receptor.

The subject treated in the methods above is a mammal, preferably a human being, male or female, in whom modulation of chemokine receptor activity is desired. "Modulation" as used herein is intended to encompass antagonism, agonism, partial antagonism, inverse agonism and/or partial agonism. In a preferred aspect of the present invention, modulation refers to antagonism of chemokine receptor activity. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment.

Combined therapy to modulate chemokine receptor activity and thereby prevent and treat inflammatory and immunoregulatory disorders and diseases, including asthma and allergic diseases, as well as autoimmune pathologies such as rheumatoid arthritis and atherosclerosis, and those pathologies noted above is illustrated by the combination of the compounds of this invention and other compounds which are known for such utilities.

For example, in the treatment or prevention of inflammation, the present compounds may be used in conjunction with an antiinflammatory or analgesic agent such as an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the instant compounds may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or nonsedating antihistamine. Likewise, compounds of the present invention may be used in combination with other drugs that are used in the treatment/prevention/suppression or amelioration of the diseases or conditions for which compounds of the pressent invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention. Examples of other active ingredients that may be combined with a compound of the present invention, either administered separately or in the same pharmaceutical compositions, include, but are not limited to: (a) VLA-4 antagonists such as those described in U.S. Pat. No. 5,510,332, WO95/15973, WO96/01644, WO96/06108, WO96/20216, WO96/22966, WO96/31206, WO96/40781, WO97/03094, WO97/02289, WO98/42656, WO98/53814, WO98/53817, WO98/53818, WO98/54207, and WO98/58902; (b) steroids such as beclomethasone, methylprednisolone, betamethasone, prednisone, dexamethasone, and hydrocortisone; (c) immunosuppressants such as cyclosporin, tacrolimus, rapamycin and other FK-506 type immunosuppressants; (d) antihistamines (H1-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (e) non-steroidal anti-asthmatics such as β2-agonists (terbutaline, metaproterenol, fenoterol, isoetharine, albuterol, bitolterol, and pirbuterol), theophylline, cromolyn sodium, atropine, ipratropium bromide, leukotriene antagonists (zafirlukast, montelukast, pranlukast, iralukast, pobilukast, SKB-106,203), leukotriene biosynthesis inhibitors (zileuton, BAY-1005); (f) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CXCR-4, CCR-1, CCR-2, CCR-3 and CCR-5; (j) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-diabetic agents such as insulin, sulfonylureas, biguanides (metformin), α-glucosidase inhibitors (acarbose) and glitazones (troglitazone and pioglitazone); (l) preparations of interferon beta (interferon beta-1α, interferon beta-1β); (m) other compounds such as 5-aminosalicylic acid and prodrugs thereof, antimetabolites such as azathioprine and 6-mercaptopurine, and cytotoxic cancer chemotherapeutic agents. The weight ratio of the compound of the compound of the present invention to the second active ingredient may be varied and will depend upon the effective dose of each ingredient. Generally, an effective dose of each will be used. Thus, for example, when a compound of the present invention is combined with an NSAID the weight ratio of the compound of the present invention to the NSAID will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

The present invention is further directed to combinations of the present compounds with one or more agents useful in the prevention or treatment of AIDS. For example, the compounds of this invention may be effectively administered, whether at periods of pre-exposure and/or post-exposure, in combination with effective amounts of the AIDS antivirals, immunomodulators, anti-infectives, or vaccines known to those of ordinary skill in the art.

ANTIVIRALS

| Drug Name | Manufacturer | Indication |
| --- | --- | --- |
| 097 | Hoechst/Bayer | HIV infection, AIDS, ARC (non-nucleoside reverse transcriptase inhibitor) |
| 141 W94 | Glaxo Wellcome | HIV infection, AIDS, ARC (protease inhibitor) |
| 1592U89 | Glaxo Wellcome | HIV infection, AIDS, ARC |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which neutralizes pH labile alpha aberrant Interferon | Advanced Biotherapy Concepts (Rockville, MD) | AIDS, ARC |
| AR177 | Aronex Pharm | HIV infection, AIDS, ARC |
| beta-fluoro-ddA | Nat'l Cancer Institute | AIDS-associated diseases |
| (–) 6-Chloro-4(S)-cyclopropylethynyl-4(S)-trifluoro-methyl-1,4-dihydro-2H-3,1-benzoxazin-2-one | Merck | HIV infection, AIDS, ARC (non-nucleoside reverse transcriptase inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus immune globin | MedImmune | CMV retinitis |
| Cytovene Ganciclovir | Syntex | sight threatening CMV peripheral CMV retinitis |
| Delaviridine | Pharmacia-Upjohn | HIV infection, AIDS, ARC (protease inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC, combination with AZT/d4T |
| DMP-450 | A VID (Camden, NJ) | HIV infection, AIDS, ARC (protease inhibitor) |
| EL10 | Elan Corp, PLC (Gainesville, GA) | HIV infection |
| Efavirenz (DMP 266) (–) 6-Chloro-4(S)-cyclopropylethynyl-4(S)-trifluoro-methyl-1,4-dihydro-2H-3,1-benzoxazin-2-one, | DuPont (SUSTIVA ®), Merck (STOCRIN ®) | HIV infection, AIDS, ARC (non-nucleoside RT inhibitor) |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| GW 141 | Glaxo Welcome | HIV infection, AIDS, ARC (protease inhibitor) |
| GW 1592 | Glaxo Welcome | HIV infection, AIDS, ARC (reverse transcriptase inhibitor) |

-continued

| Drug Name | Manufacturer | Indication |
| --- | --- | --- |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| Compound A | Merck | HIV infection, AIDS, ARC, asymptomatic HIV positive |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (protease inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxythymidine | Bristol-Myers Squibb | HIV infection, AIDS, ARC |
| T-20 | Trimeris | HIV infection, AIDS, ARC |
| Valaciclovir | Glaxo Wellcome | genital HSV & CMV infections |
| Virazole Ribavirin | Viratek/ICN (Costa Mesa, CA) | asymptomatic HIV positive, LAS, ARC |
| Amprenivir VX478 | Vertex | HIV infection, AIDS, ARC |
| Zalcitabine | Hoffman-La Roche | HIV infection, AIDS, ARC, with AZT |
| Zidovudine; AZT | Glaxo Wellcome | HIV infection, AIDS, ARC, Kaposi's sarcoma, in combination with other therapies |
| ABT-378 | Abbott | HIV infection, AIDS, ARC (protease inhibitor) |
| JE2147/AG1776 | Agouron | HIV infection, AIDS, ARC (protease inhibitor) |
| T-20 T-1249 | Trimeris | HIV infection, AIDS, ARC (fusion inhibitor) |
| BMS 232632 | Bristol-Myers-Squibb | HIV infection, AIDS, ARC (protease inhibitor) |

IMMUNO-MODULATORS

| Drug Name | Manufacturer | Indication |
| --- | --- | --- |
| AS-101 | Wyeth-Ayerst | AIDS |
| Bropirimine | Pharmacia Upjohn | advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoeschst-Roussel Immunex | AIDS |
| Granulocyte Macrophage Colony Stimulating Factor | Schering-Plough | AIDS, combination w/AZT |
| HIV Core Particle Immunostimulant | Rorer | seropositive HIV |
| IL-2 Interleukin-2 | Cetus | AIDS, in combination w/AZT |
| IL-2 Interleukin-2 | Hoffman-La Roche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 | Smith Kline | HIV infection |

-continued

| Drug Name | Manufacturer | Indication |
| --- | --- | --- |
| Thymopentin | Immunobiology Research Institute | HIV infection |
| Tumor Necrosis Factor; TNF | Genentech | ARC, in combination w/gamma Interferon |
| etanercept | Immunex Corp (Enbrel ®) | rheumatoid arthritis |
| infliximab | Centocor (Remicade ®) | rheumatoid arthritis and Crohn's disease |

ANTI-INFECTIVES

| Drug Name | Manufacturer | Indication |
| --- | --- | --- |
| Clindamycin with Primaquine | Pharmacia Upjohn | PCP |
| Fluconazole | Pfizer | cryptococcal meningitis, candidiasis |
| Pastille Nystatin Pastille | Squibb Corp. | prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | antibacterial |
| Trimethoprim/sulfa | | antibacterial |
| Piritrexim | Burroughs Wellcome | PCP treatment |
| Pentamidine isethionate for inhalation | Fisons Corporation | PCP prophylaxis |
| Spiramycin | Rhone-Poulenc | cryptosporidial diarrhea |
| Intraconazole-R51211 | Janssen Pharm. | histoplasmosis; cryptococcal meningitis |
| Trimetrexate | Warner-Lambert | PCP |

OTHER

| Drug Name | Manufacturer | Indication |
| --- | --- | --- |
| Daunorubicin | NeXstar, Sequus | Karposi's sarcoma |
| Recombinant Human Erythropoietin | Ortho Pharm. Corp. | severe anemia assoc. with AZT therapy |
| Recombinant Human Growth Hormone | Serono | AIDS-related wasting, cachexia |
| Leukotriene B4 Receptor Antagonist | — | HIV infection |
| Megestrol Acetate | Bristol-Myers Squibb | treatment of anorexia assoc. w/AIDS |
| Soluble CD4 Protein and Derivatives | — | HIV infection |
| Testosterone | Alza, Smith Kline | AIDS-related wasting |
| Total Enteral Nutrition | Norwich Eaton Pharmaceuticals | diarrhea and malabsorption related to ADS |

It will be understood that the scope of combinations of the compounds of this invention with AIDS antivirals, immunomodulators, anti-infectives or vaccines is not limited to the list in the above Table, but includes in principle any combination with any pharmaceutical composition useful for the treatment of AIDS.

Preferred combinations are simultaneous or alternating treatments with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. Preferred agents for combination therapy include: Zidovudine, Lamivudine, Stavudine, Efavirenz, Ritonavir, Nelfinavir, Abacavir, Indinavir, 141-W94 (4-amino-N-((2 syn,3S)-2-hydroxy-4-phenyl-3-((S)-tetrahydrofuran-3-yloxycarbonylamino)-butyl)-N-isobutyl-benzenesulfonamide), N-(2(R)-hydroxy-1(S)-indanyl)-2(R)-phenylmethyl-4-(S)-hydroxy-5-(1-(4-(2-benzo[b]furanylmethyl)-2(S)-N'(t-butylcarbox-amido)-piperazinyl))-pentaneamide, and Delavirdine. A preferred inhibitor of HIV protease is indinavir, which is the sulfate salt of N-(2(R)-hydroxy-1(S)-indanyl)-2(R)-phenylmethyl-4-(S)-hydroxy-5-(1-(4-(3-pyridyl-methyl)-2(S)-N'-(t-butylcarbo-xamido)-piperazinyl))-pentane-amide ethanolate, and is synthesized according to U.S. Pat. No. 5,413,999. Indinavir is generally administered at a dosage of 800 mg three times a day. Other preferred inhibitors of HIV protease include nelfinavir and ritonavir. Preferred non-nucleoside inhibitors of HIV reverse transcriptase include (−) 6-chloro-4(S)-cyclopropylethynyl-4(S)-trifluoromethyl-1,4-dihydro-2H-3,1-benzoxazin-2-one, which may be prepared by methods disclosed in EP 0,582,455. The preparation of ddC, ddI and AZT are also described in EPO 0,484,071. These combinations may have unexpected effects on limiting the spread and degree of infection of HIV. Preferred combinations with the compounds of the present invention include the following: (1) Zidovudine and Lamivudine; (2) Stavudine and Lamivudine; (3) Efavirenz; (4) Ritoavir; (5) Nelfinavir; (6) Abacavir; (7) Indinavir; (8) 141-W94; and (9) Delavirdine. Preferred combinations with the compounds of the present invention further include the following (1) indinavir, with efavirenz or (−) 6-chloro-4(S)-cyclopropylethynyl-4(S)-trifluoromethyl-1,4-dihydro-2H-3,1-benzoxazin-2-one, and, optionally, AZT and/or 3TC and/or ddI and/or ddC; (2) indinavir, and any of AZT and/or ddI and/or ddC.

Compound A in the foregoing Table is N-(2(R)-hydroxy-1(S)-indanyl)-2(R)-phenylmethyl-4(S)-hydroxy-5-(1-(4-(2-benzo[b]furanylmethyl)-2(S)-N'-(t-butylcarboxamido)-piperazinyl))pentaneamide, preferably administered as the sulfate salt. Compound A can be prepared as described in U.S. Pat. No. 5,646,148.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are commercially available, are made by known procedures or are prepared as illustrated.

SCHEME 1

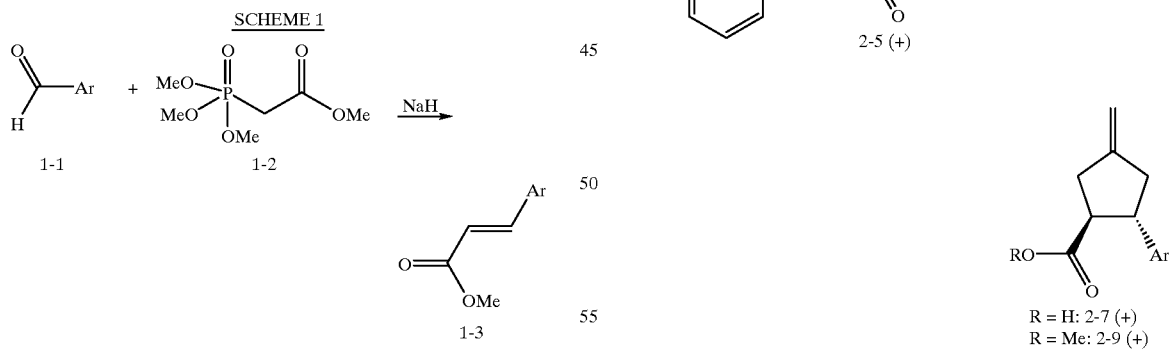

The preparation of cinnamate esters such as 1-3 as intermediates that can be used for the synthesis of compounds within the scope of the instant invention is detailed in Scheme 1. Cinnamate esters of structure 1-3 can be obtained commercially or can be synthesized by reacting a suitable aromatic aldehyde 1-1 with a phosphonoacetate such as 1-2 in the presence of sodium hydride or other bases such as sodium, lithium or potassium hexamethyldisilazide, potassium t-butoxide, and the like. The aldehyde 1-1 can be obtained commercially or can be prepared in a variety of ways from commercial materials (see March J. "Advanced Organic Chemistry", 4th ed., John Wiley & Sons, New York, pp. 1270–1271 (1992)).

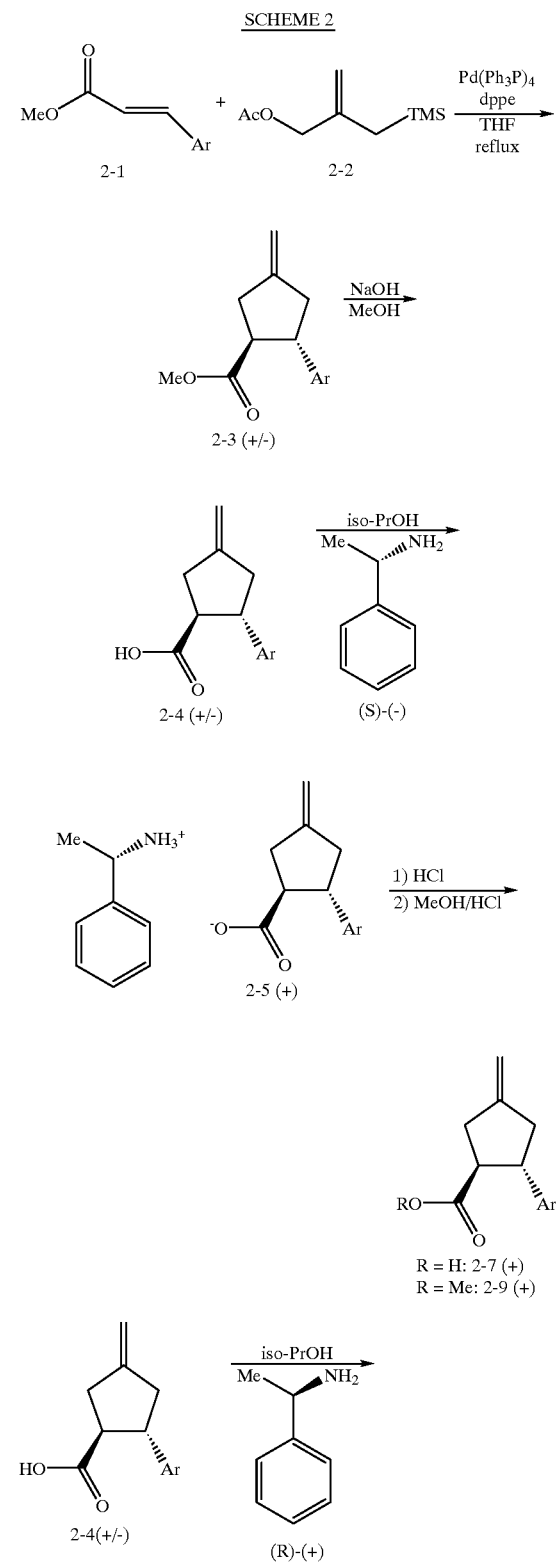

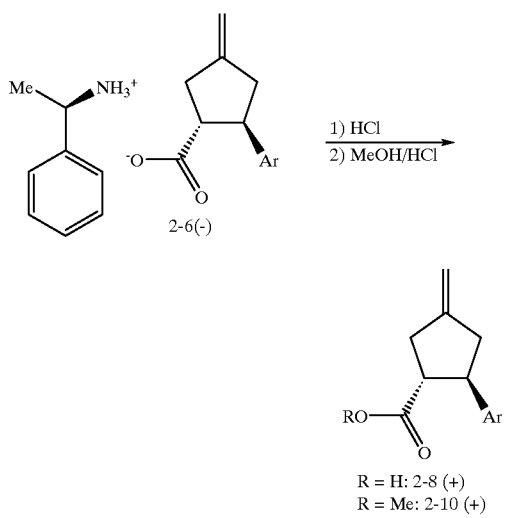

A preparation of cyclopentane intermediates having a C-4 aryl substituent within the scope of the instant invention is detailed in Scheme 2 and can be used to prepare non-racemic cyclopentane derivatives when the resolution steps are done. Treatment of a trans-cinnamic ester such as 2-1 (see Scheme 1) with 2-((trimethylsilyl)methyl)-2-propen-1-yl acetate (2-2) in the presence of a catalytic amount of tetrakis (triphenylphosphine) palladium (0) and 1,2-bis (diphenylphosphino)ethane in THF at reflux afforded the exo-methylene cyclopentane 2-3. Hydrolysis of the ester can be done several ways, such as with aqueous sodium or lithium hydroxide in methanol or THF, to obtain the racemic acid 2-4. Resolution of the enantiomers can be accomplished by fractional crystallization from isopropanol, or other suitable solvents, of the salts with either (R)-(+)- or (S)-(−)-α-methylbenzyl amine to give the salts 2-5 and 2-6. The non-racemic acids 2-7 and 2-8 are recovered by acidification and extraction. Reesterification to 2-9 and 2-10 can be done in a variety of ways, such as with trimethylsilyldiazomethane or acid catalyzed esterification in methanol.

SCHEME 2A

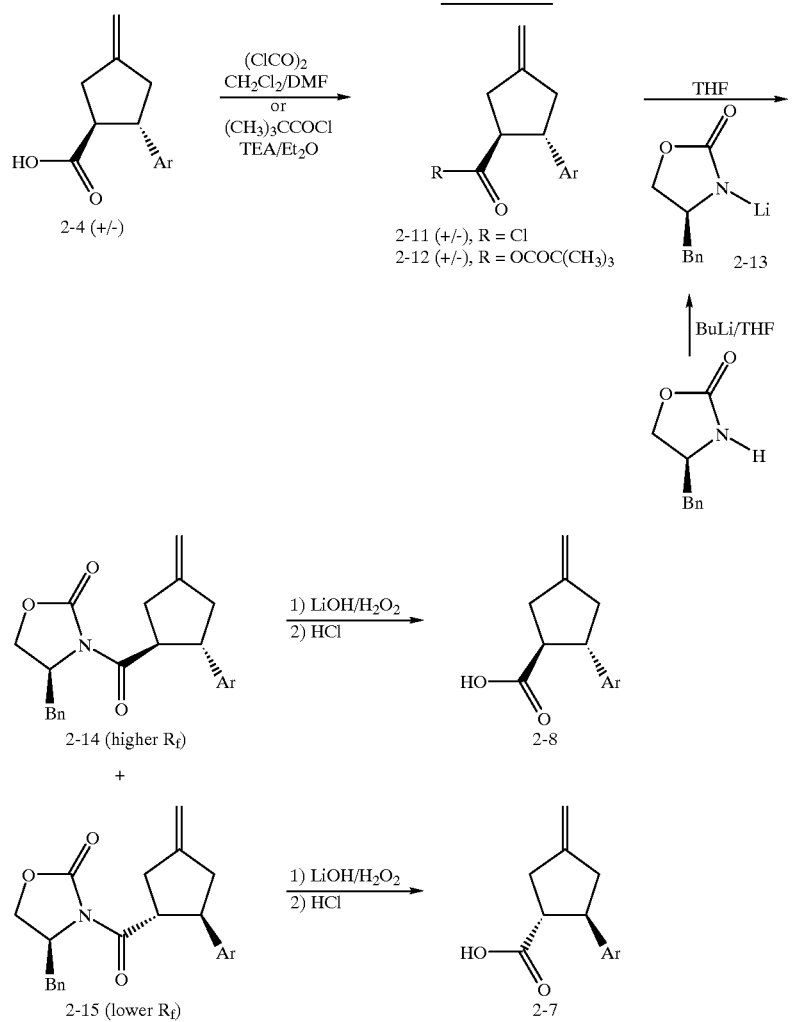

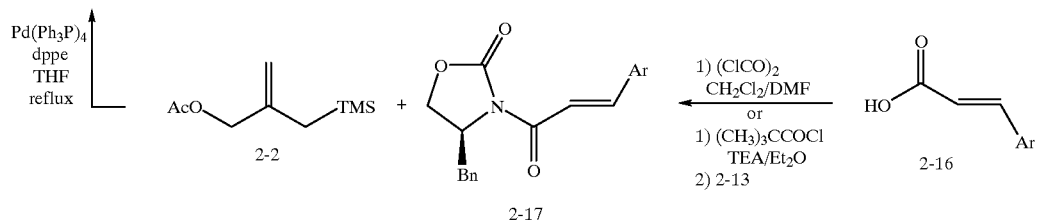

An alternative preparation of non-racemic cyclopentane intermediates having a C4 aryl substituent within the scope of the instant invention is detailed in Scheme 2A. Conversion of the cyclopentane acid 2-4 to the acid chloride 2-11 under standard conditions, such as with oxalyl chloride in methylene chloride with a catalytic amount of DMF, or to the mixed anhydride 2-12, prepared in situ with trimethylacetyl chloride in ether with TEA as base, followed by reaction with the performed lithium salt of (S)-(−)-4-benzyl-2-oxazolidinone 2-13, afforded the two non-racemic diastereomeric products 2-14 and 2-15, which are then separable by chromatography. Hydrolysis of each diastereomer under standard conditions, such as with lithium hydroxide and hydrogen peroxide, affords the two non-racemic acids 2-7 and 2-8. Alternatively, in order to obtain an enhanced amount of the desired diastereomer 2-14 before separation, similar conversion of the starting trans-cinnamic acid 2-16 (Scheme 1) to the chiral trans-cinnamate 2-17 followed by the ring formation reaction with 2-((trimethylsilyl)methyl)-2-propen-1-yl acetate (2-2) as detailed in Scheme 2A affords a 60:40 product mixture of 2-14:2-15.

(from Scheme 2), for example, with lithium borohydride, diisobutylaluminum hydride, lithium aluminum hydride, or sodium bis(2-methoxyethoxy)aluminum hydride in a suitable solvent, such as ether or THF, provides the primary alcohol 3-2. Alternatively, reduction of the acid 3-1 (R=H) (either racemic or non-racemic) (from Scheme 2 or 2B), for example with lithium aluminum hydride in THF, will also afford the alcohol 3-2. In cases where the Ar moiety is not amenable to salt resolution as detailed in Scheme 2, an alternative resolution can often be achieved using chiral HPLC methods to separate the enantiomers of 3-2. Ozonolysis of the exo-methylene can be done by treating a solution of 3-2 in a suitable solvent, such as methanol or methylene chloride, at reduced temperature, preferably at −70° C., followed by a reductive work-up with excess dimethyl sulfide at −70° C. to room temperature to afford the ketone 3-3. If required for further functionalization of the ketone, the alcohol can be protected with a t-butyldimethylsilyl group by reaction of 3-3 in a suitable solvent, such as methylene chloride or THF, with t-butyldimethylsilyl chloride in the presence of a hindered

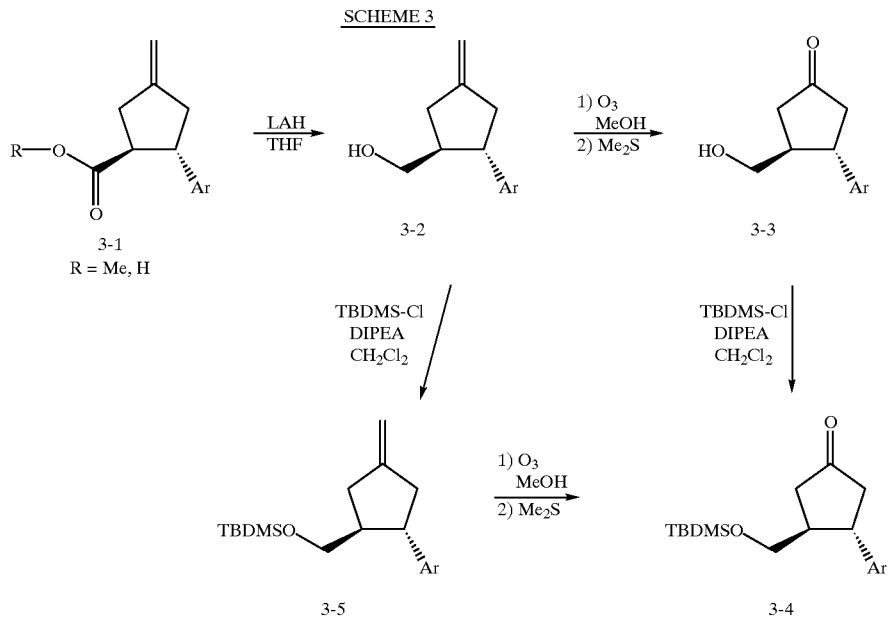

The preparation of further cyclopentane intermediates having a C-4 aryl substituent within the scope of the instant invention is detailed in Scheme 3 and can be used to prepare racemic and non-racemic cyclopentane derivatives. Reduction of ester 3-1 (R=Me) (either racemic or non-racemic)

base, such as TEA or DIPEA. Alternatively, the exo-methylene-alcohol 3-2 can be protected with the t-butyldimethylsilyl group as above to give 3-5 prior to the ozonolysis to afford the same alcohol protected intermediate 3-4.

SCHEME 4

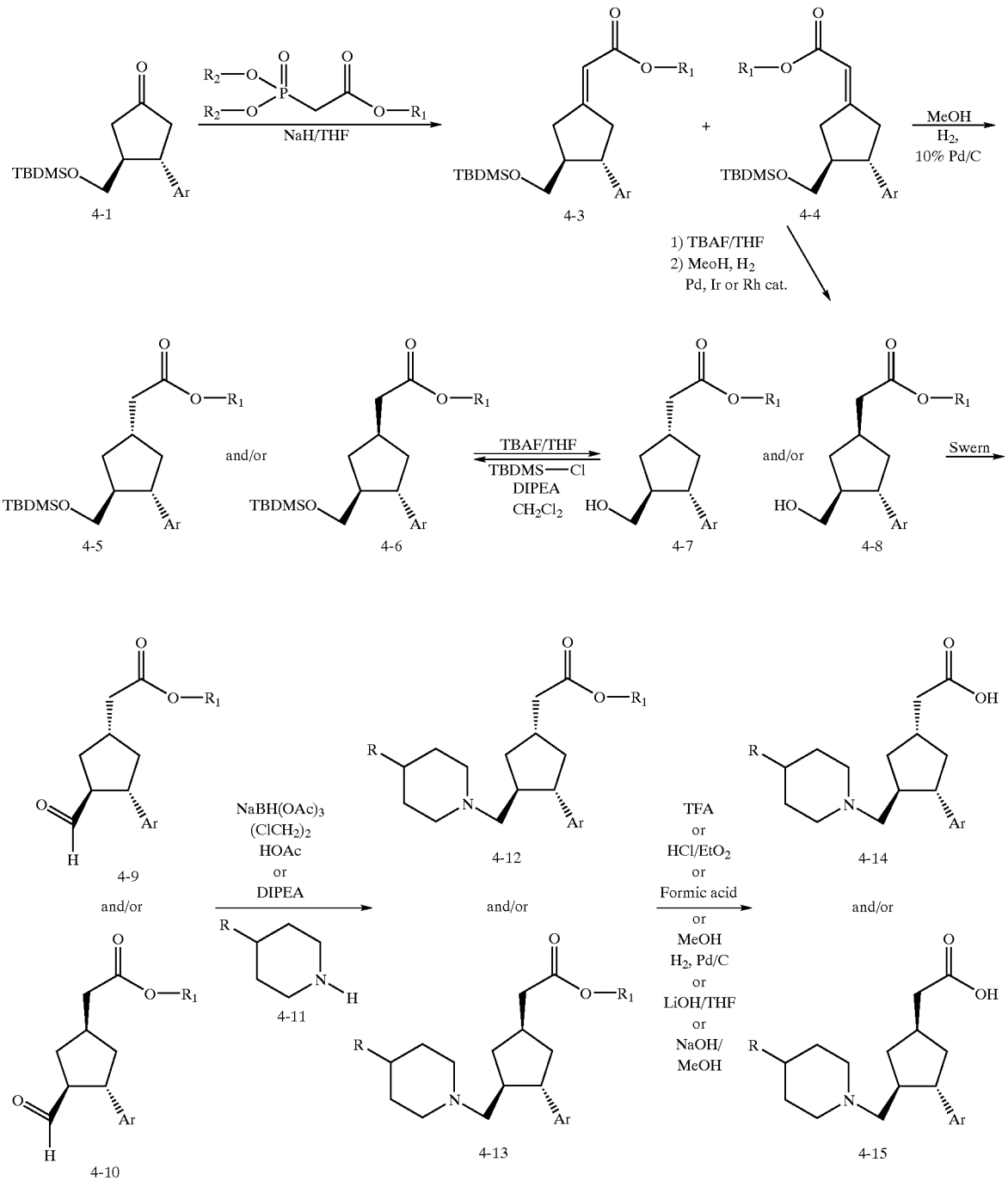

A route for the preparation of some 1,3,4-trisubstituted cyclopentanes within the scope of the instant invention is given in Scheme 4. Reaction of ketone 4-1 (from Scheme 3) with a dialkylphosphonoacetic acid ester such as 4-2 ($R_1$=Et, t-Bu, Bn, PMB; $R_2$=Me, Et) (Horner-Wadsworth-Emmons modified ylid reaction) in a suitable solvent, such as THF, dimethylsulfoxide or DMF, in the presence of a strong base, such as sodium hydride or lithium hexamethyldisilazide, at 0 to 70° C., preferably at rt, affords a mixture of double bond products 4-3 and 4-4. Removal of the TBDMS (see below) group allows for the chromatographic separation of these isomers if desired. Normally, these were hydrogenated under standard conditions, such as in methanol at atmospheric to 60 psi of hydrogen in the presence of a palladium catalyst, such as 10% palladium on carbon or 20% palladium hydroxide on carbon (Pearlman's catalyst) to the cyclopentane acetic acid derivatives as a mixture of the C-1 isomers 4-5 and 4-6, with 4-6 usually being the predominant isomeric product, the ratio depending on conditions and the catalyst used. Since the TBDMS group is prone to cleavage under these conditions to give 4-7 and 4-8, the hydroxy group can be reprotected using standard conditions with TBDMS-Cl (see Scheme 3). Alternatively, the TBDMS group can be completely removed using either acidic alcohol, such as HCl in methanol, or using TBAF in THF, both at 0° C. to rt to afford 4-7 and 4-8, which can be separated by chromatography. Alternatively, the TBDMS group can be removed prior to the hydrogenation under acidic conditions or with TBAF (see above). Hydrogenation of the intermediate alcohol under standard conditions as above or with a hydroxy directed catalyst, such as (bicyclo[2.2.1]hepta-2,5-diene)[1,4-bis(diphenylphosphino)butane]rhodium(I) tetrafluoroborate or (1,5-cyclooctadiene)(pyridine)(tricyclohexylphosphine)iridium (I) hexafluorophosphate, in methylene chloride or THF, can afford predominantly the other isomeric product 4-7. Oxidation of 4-7 and/or 4-8 to the aldehyde(s) 4-9 and/or 4-10 can be carried out under numerous conditions, such as with DMSO and oxalyl chloride at low temperature, followed by triethylamine (Swern oxidation), with the Dess-Martin periodinane, with N-methylmorpholine in the presence of a catalytic amount of TPAP, or with various chromium trioxide-based reagents (see March J. "Advanced Organic Chemistry", 4th ed., John Wiley & Sons, New York, pp. 1167–1171 (1992)). Reductive alkylation of a cyclic amine, such as piperidine 4-11 (see Schemes 12 to 29), using for example sodium triacetoxyborohydride or sodium cyanoborohydride in a suitable solvent such as methylene chloride, 1,2-dichloroethane, THF, acetonitrile or methanol, with 4-9 and/or 4-10 then provides a 3-(4-(substituted-piperidin-1-yl)methyl)cyclopentane derivative 4-12 and/or 4-13 which also may be separable by chromatography. When $R_1$ is t-Bu or PMB, final deprotection of the acetic acid ester to give 4-14 and/or 4-15 can be done using acidic conditions, such as HCl in ether, formic acid or TFA. When $R_1$ is an alkyl ester, standard basic hydrolysis can be used, such as sodium or lithium hydroxide in aq. ethanol, methanol or THF. When $R_1$ is Bn or PMB, standard hydrogenation can be used for the deprotection. These acid derivatives are within the scope of the instant invention and can be chemokine receptor modulators. The choice of $R_1$ is made depending on the availability of 4-2 or the stability of the piperidine R moiety and can be changed during the above sequence by suitable removal and re-esterification, such as hydrolysis of an ethyl ester (4-5 to 4-8, $R_1$=Et) and replacement with a PMB ester (4-5 to 4-8, $R_1$=PMB), using for example PMB-Cl in DMF with TEA as base, after the hydrogenation to 4-5 and 4-6 or 4-7 and 4-8.

SCHEME 5

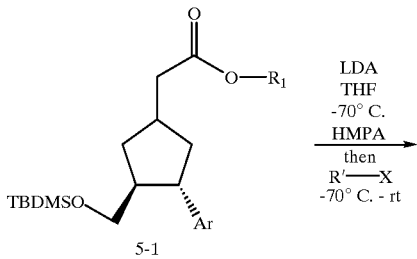

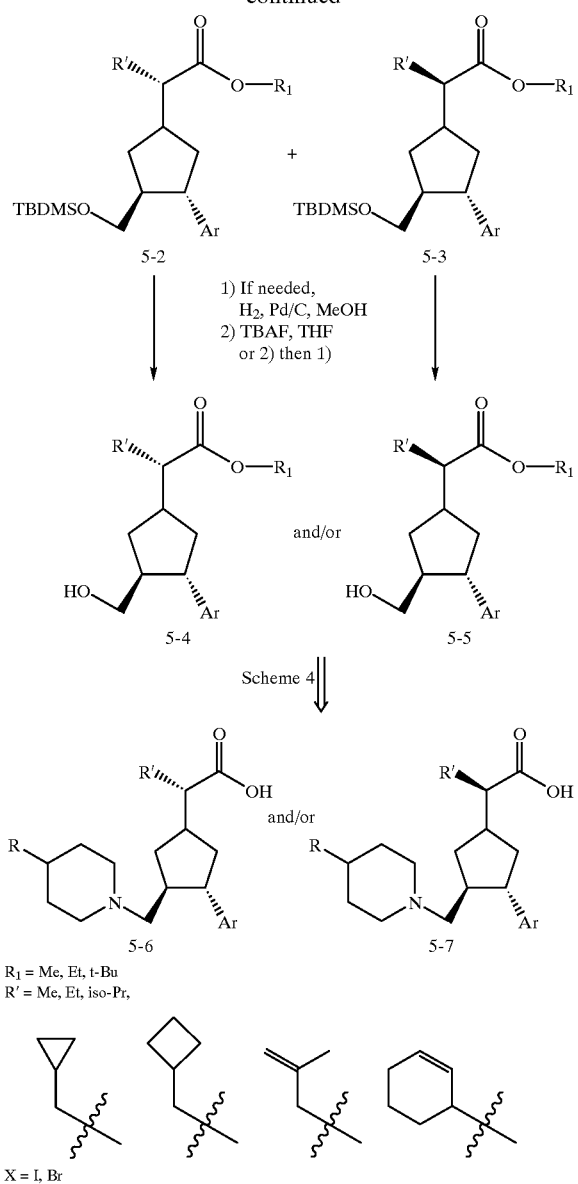

$R_1$ = Me, Et, t-Bu
$R'$ = Me, Et, iso-Pr,

X = I, Br

An alternative route for the preparation of some 1,3,4-trisubstituted cyclopentanes within the scope of the instant invention is given in Scheme 5. Alkylation of the acetic acid moiety of 5-1 (from Scheme 4, either as racemic or non-racemic and either as a single C-1 isomer or as a mixture) can be done under a variety of conditions with an appropriate alkylating agent, such as an alkyl or allyl halide or sulfonate, in the presence of a strong base, such as sodium hydride in DMF or KHMDS or LDA in THF at low temperature in the presence or absence of an anion stabilizer, such as HMPA, to give the 2 isomeric 2-alkyl acetic acid derivatives 5-2 and 5-3. Removal of the TBDMS group with TBAF (see Scheme 4) affords the alcohols 5-4 and 5-5 which may be separable by chromatographic methods. Oxidation to the aldehyde(s), reductive alkylation of a 4-substituted piperidine (see Schemes 12–29) and final removal of the acetic acid ester as described for Scheme 4 then affords the final product(s) 5-6 and/or 5-7. When an allyl derivative is used in the above alkylation, it can itself be a chemokine receptor modulator within the scope of the present invention or the double bond can be hydrogenated at the stage of 5-2 and 5-3 or 5-4 and 5-5 or at a point later in the sequence depending on the stability of the R and $R_1$ groups to various conditions.

SCHEME 6

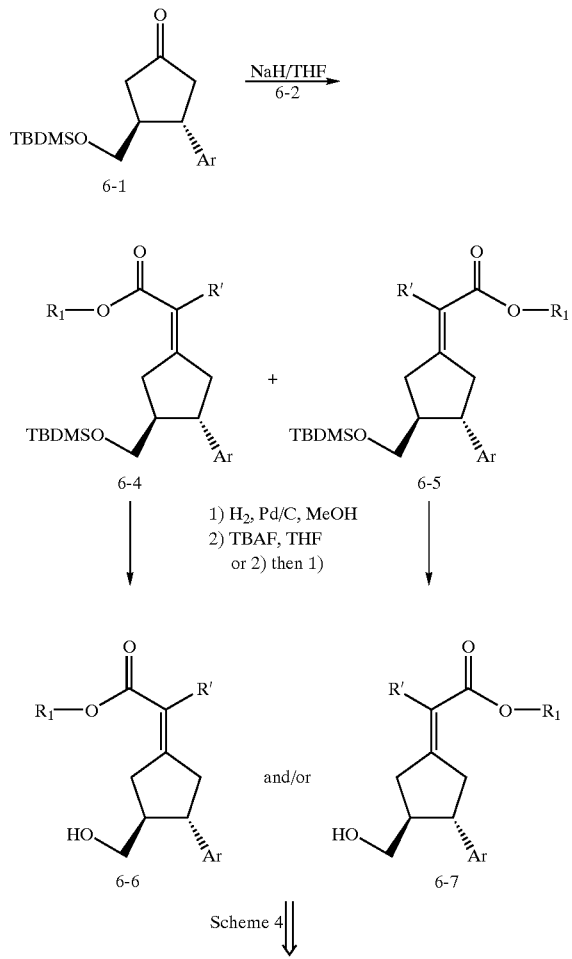

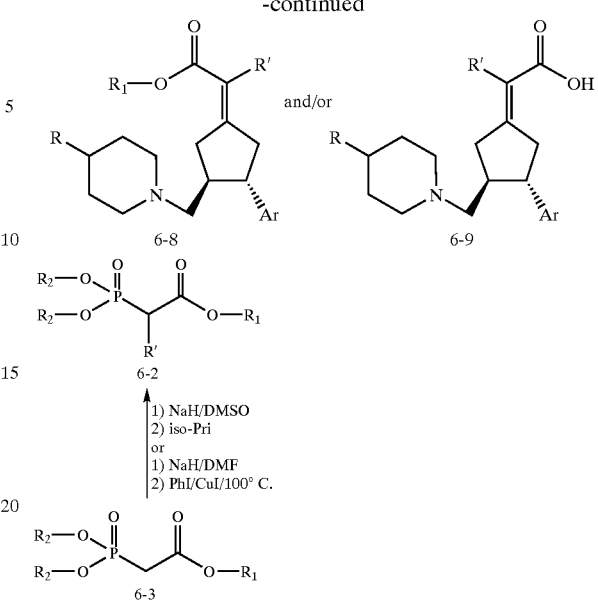

An alternative route for the preparation of some 1,3,4-trisubstituted cyclopentanes within the scope of the instant invention is given in Scheme 6. The ketone 6-1 (from Scheme 3) can be reacted with a 2-alkylsubstituted dialkylphosphonoacetic acid ester, such as 6-2 in which R' is Me, Et, cyclohexyl, iso-propyl, iso-butyl, cyclopropylmethyl, cyclobutylmethyl, etc. and fluoro, to afford 6-4 and 6-5 which may be separable by chromatographic methods. When the desired dialkylphosphonoacetic acid ester is not commercially available, it can be prepared by alkylation of 6-3 under standard conditions, such as with an alkyl or allyl halide using a strong base, such as sodium hydride or LHMDS, in a suitable solvent, such as DMF, THF or DMSO. Alternatively, 6-3 can be alkylated using sodium hydride as a base in DMF in the presence of CuI at 100° C. The intermediate(s) 6-4 and/or 6-5 can be used as a mixture or may be separated by chromatography into a single double bond isomer at this point or after de-silylation to 6-6 and 6-7. These are then converted to the final product(s) 6-8 and/or 6-9 as described in Scheme 4. When R' in 6-2 contains a double bond, it can be selectively hydrogenated to the corresponding saturated compound, under standard conditions with 10% Pd/C in methanol, as 6-4 to 6-7 or further on in the sequence depending on the compatibility of R, R' and $R_1$.

SCHEME 7

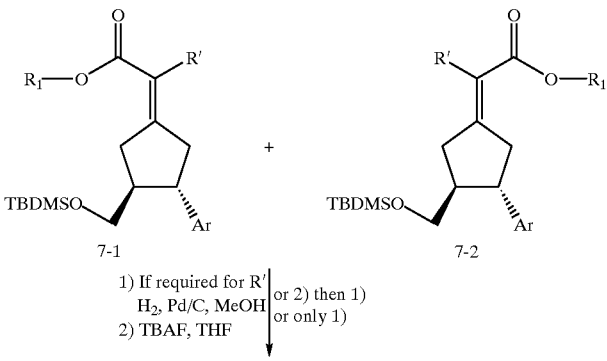

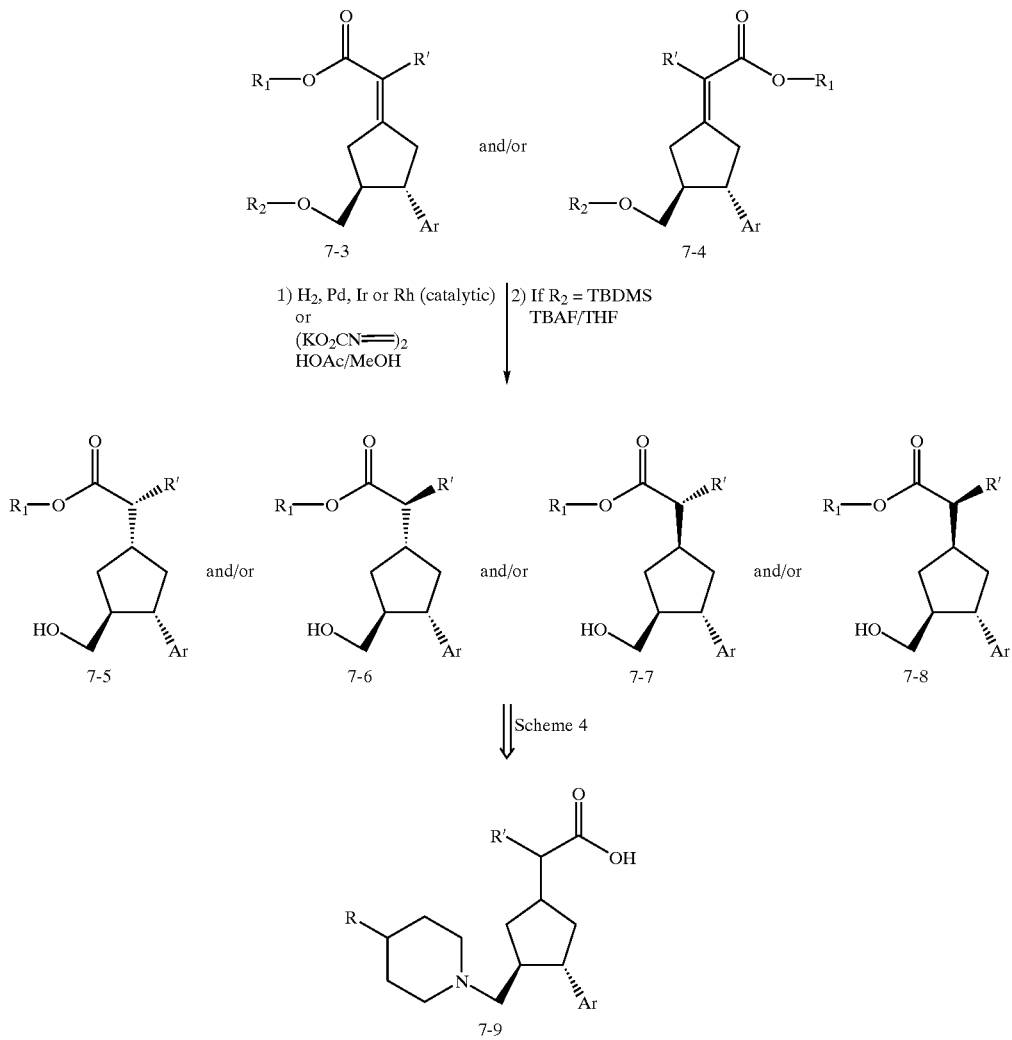

An alternative route for the preparation of some 1,3,4-trisubstituted cyclopentanes within the scope of the instant invention is given in Scheme 7. The TBDMS ethers 7-1 and/or 7-2 (from Scheme 6, either separate or as a mixture) can be desilylated with TBAF (see Scheme 4) to afford the alcohols 7-3 and/or 7-4. When R' contains unsaturation, this can be selectively hydrogenated either prior to or following the desilylation, depending on the best point of separation and the stability of the TBDMS group. The C-1 exo-methylene unsaturation can be hydrogenated either catalytically under standard conditions with Pd ($R_2$=TBDMS) or alcohol directed conditions with Ir or Rh ($R_2$=H) (see Scheme 4) or with chemical reduction, such as with potassium azodicarboxylate in the presence of acetic acid in methanol, to afford the 4 possible stereoisomers 7-5 to 7-8. These isomers may be separable at this step or later in the sequence. The choice of catalyst and whether the reduction is done on the TBDMS ether or alcohol can alter the ratio of C-1 epimeric products obtained as described in Scheme 4 and can be used to preferentially obtain the desired isomer(s). These are then converted to the final product(s) 7-9 as described in Scheme 4. When R' contains a double bond, it can be selectively hydrogenated as above in a separate reaction or simultaneously with the reduction of the C-1 exo-methylene to the corresponding saturated compounds 7-5 to 7-8.

SCHEME 8

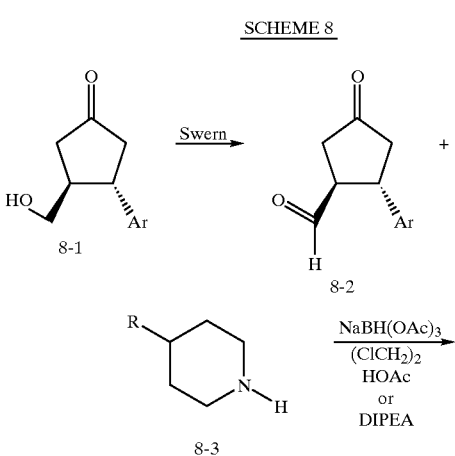

SCHEME 9

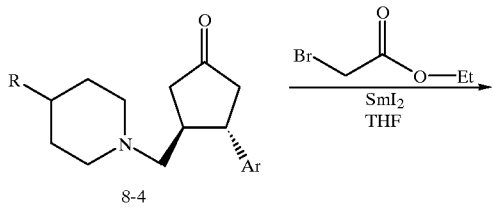

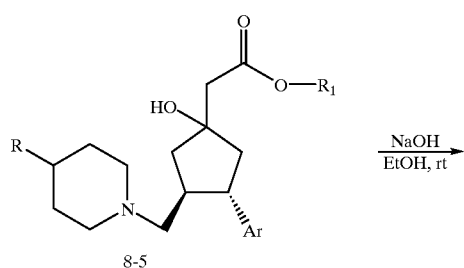

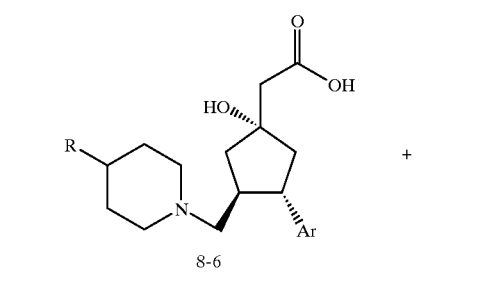

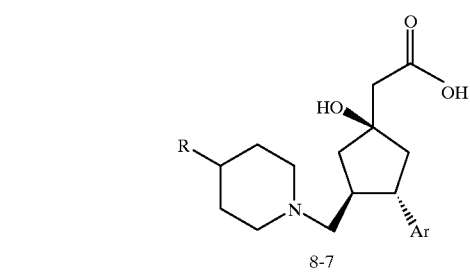

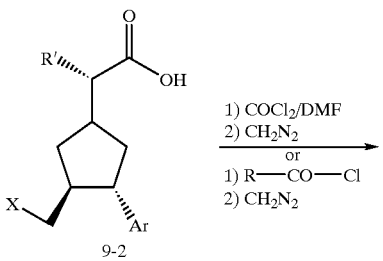

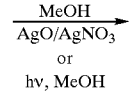

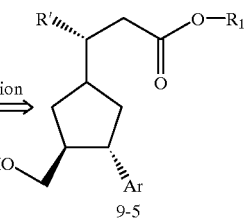

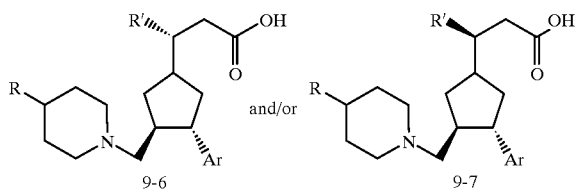

An alternative route for the preparation of some 1,3,4-trisubstituted cyclopentanes within the scope of the instant invention is given in Scheme 8. The alcohol 8-1 (from Scheme 3) can be oxidized to the aldehyde 8-2 under a variety of methods (see Scheme 4), such as Swern conditions. Selective reductive alkylation of a 4-substituted piperidine 8-3 with the aldehyde of 8-2 using for example sodium triacetoxyborohydride or sodium cyanoborohydride in a suitable solvent, such as methylene chloride, methanol or 1,2-dichloroethane, affords the ketone product 8-4. Addition of acetate to the ketone, such as in the free radical addition of ethyl bromoacetate in the presence of SmI$_2$ in THF, gives a mixture of the C-1 alcohols 8-5. Careful hydrolysis of the ethyl ester afforded the separable acids 8-6 and 8-7 which are within the scope of the present invention and which can be chemokine receptor modifiers.

An alternative route for the preparation of some 1,3,4-trisubstituted cyclopentanes within the scope of the instant invention is given in Scheme 9 in which the C-1 acetic acid moiety can be homolygated. The ester 9-1 (from Scheme 5 or 7, X=OTBDMS or other suitably protected alcohol group) can be hydrolyzed under standard conditions, such as sodium hydroxide in aq. methanol, to the acid 9-2. A standard Arndt-Eistert reaction can be used to homolygate the acetic acid to a propionic acid. Thus, the acid can be activated as an acid chloride, for example with oxalyl chloride in the presence of a catalytic amount of DMF in methylene chloride, or as a mixed anhydride with iso-butyl chloroformate or pivaloyl chloride in methylene chloride. Subsequent reaction with diazomethane in an inert solvent, such as ether or methylene chloride, affords the diazoketone 9-3 which can be decomposed in methanol in the presence of silver oxide and/or silver nitrate or with irradiation in methanol to give the methyl ester 9-4. If required for conversion to the desired final product, hydrolysis of the methyl ester and reesterification can give a more compatible ester as detailed in the above schemes. Subsequent removal of the silyl ether (or other suitable alcohol protecting group) leads to the alcohol 9-5 which can be converted to the final product(s) 9-6 and/or 9-7 as detailed in Scheme 4. Alternatively, if the piperidine 4-R group in the final product is compatible with the above homolygations, X in 9-1 can be the already functionalized piperidine moiety as obtained in Schemes 4, 5 and 7 above.

invention in which the C-1 acetic acid moiety can be homolygated is given in Scheme 10. The homolygation can be achieved through reduction of either the ester 10-1 or acid 10-2 (from Scheme 5 or 7, X=OTBDMS or other suitably protected alcohol group) with an appropriate reducing agent, such as LAH in TEF, to give the alcohol 10-3. Activation of the alcohol as its mesylate and/or the bromide or iodide 10-4 followed by displacement with sodium cyanide would afford the nitrile 10-5. Hydrolysis to the acid, esterification and removal of the C-3 hydroxymethyl protecting group would led to the hydroxymethyl intermediate 10-6 which can be converted to the final product(s) 10-7 and/or 10-8 as detailed in Scheme 4. Alternatively, if the 4-R group in the final product piperidine is compatible with the above homolygations, X in 10-2 can be the already functionalized piperidine moiety as obtained in Schemes 4, 5 and 7 above.

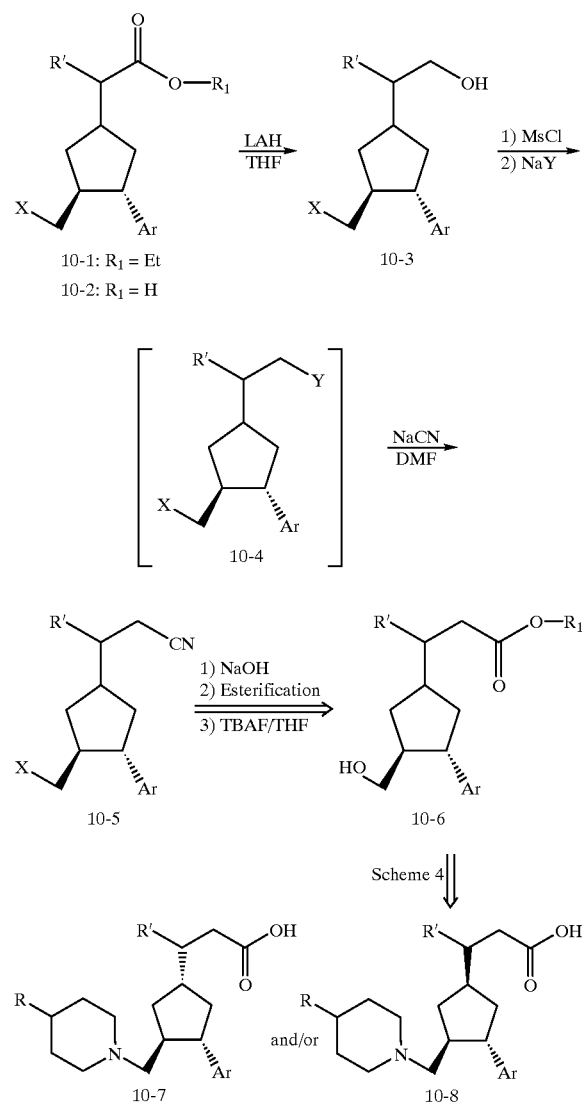

SCHEME 10

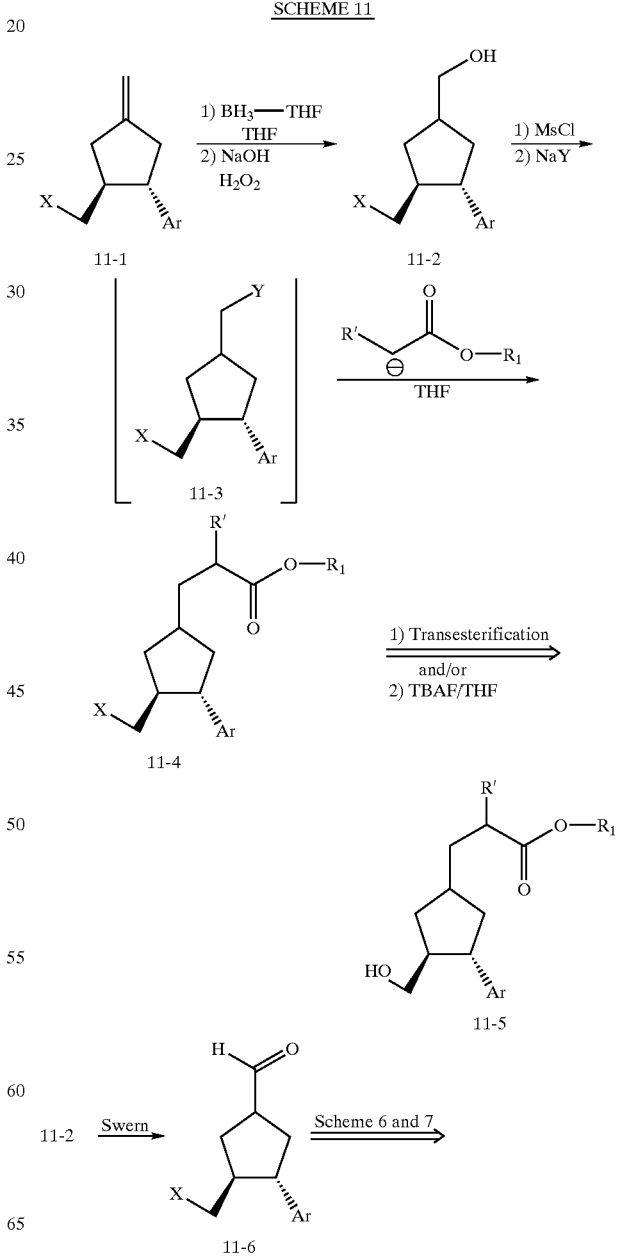

SCHEME 11

An alternative route for the preparation of some 1,3,4-trisubstituted cyclopentanes within the scope of the instant

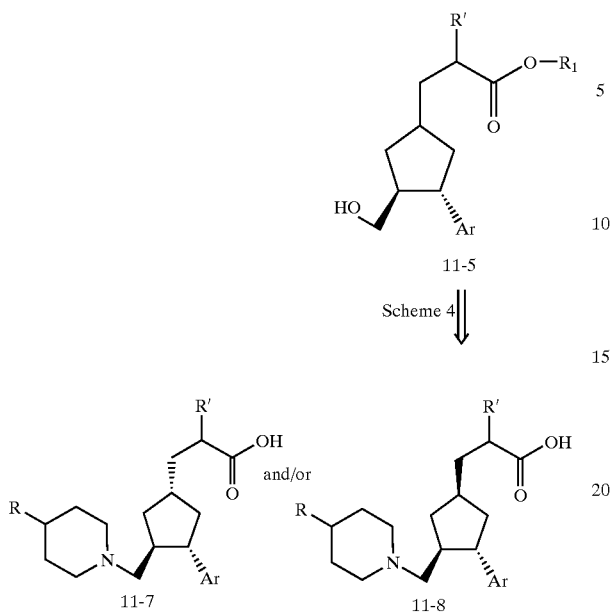

11-5

Scheme 4 ⇓

11-7    and/or    11-8

An alternative route for the preparation of some 1,3,4-trisubstituted cyclopentanes within the scope of the instant invention in which the C-1 acetic acid moiety can be homolygated is given in Scheme 11. Standard hydroboration of 11-1 (Scheme 3, X=OTBDMS or other suitably protected alcohol group), such as with borane-THF complex in THF followed by an oxidative work-up with NaOH and hydrogen peroxide or trimethylamine-N-oxide, affords the alcohol 11-2. Activation of alcohol 11-2 as the mesylate and/or bromo or iodo 11-3 and displacement with an acetate anion gives the ester 11-4 in which the R' is now on the β carbon from the cyclopentane ring. Transesterification, if necessary, followed by deprotection at C-3 leads to 11-5. Alternatively, oxidation of 11-2, such as with the Swern method, gives the aldehyde 11-6 which can be elaborated to 11-5 as shown in Schemes 4-7. The hydroxymethyl intermediate 11-5 can be converted to the final product(s) 11-7 and/or 11-8 as detailed in Scheme 4. Alternatively, if the piperidine 4-R group in the final product is compatible with the above homolygations, X in 10-2 can be the already functionalized piperidine moiety as obtained in Schemes 4, 5 and 7 above.

SCHEME 12

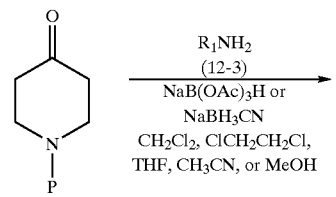

12-1 P = Boc
12-2 P = Bn

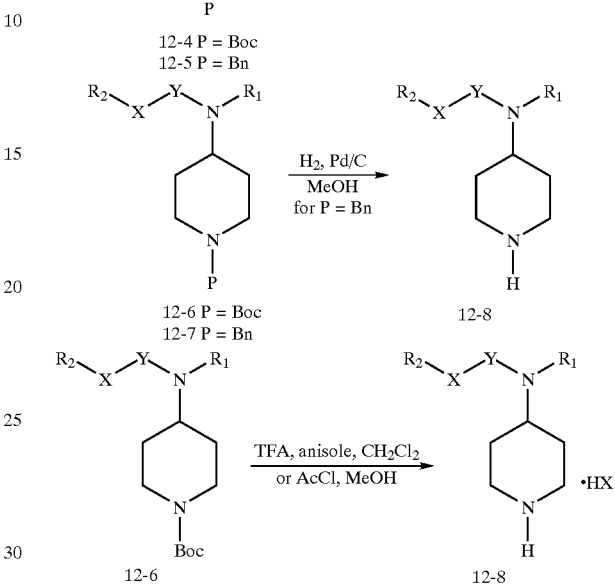

12-4 P = Boc
12-5 P = Bn 12-6 P = Boc
12-7 P = Bn 12-6

12-8

X = C(R$_3$)H, O, NH
Y = CO, SO$_2$

Synthetic routes for the preparation of piperidines bearing a 4-substituent containing an amide, carbamate, urea or sulfonamide functional group are given in Scheme 12. Reductive alkylation of commercially available 12-1 or 12-2 with primary amine 12-3 in the presence of sodium triacetoxyborohydride or sodium cyanoborohydride in a suitable solvent (for example, methylene chloride, 1,2-dichloroethane, THF, acetonitrile, or methanol) provides amines 12-4 or 12-5. Acylation is then carried out with an acyl chloride (or a carboxylic acid plus an activating agent, such as EDC, DCC, or BOP-Cl) to provide 12-6 or 12-7 as an amide. Alternatively, acylation with a chloroformate provides 12-6 or 12-7 as a carbamate. Treatment of 12-4 or 12-5 with an isocyanate affords 12-6 or 12-7 as a urea. Treatment of 12-4 or 12-5 with a sulfonyl chloride affords 12-6 or 12-7 as a sulfonamide. For each of these reactions, an amine base is employed, such as triethylamine, DIEA, pyridine, or 2,6-lutidine. In the case of the benzyl-protected derivative 12-7, hydrogenolysis under standard conditions (for example, hydrogen in the presence of palladium on carbon in methanol or ethanol) provided desired intermediate 12-8. For the N-Boc compound 12-6, exposure to suitable anhydrous acidic conditions (for example, trifluoroacetic acid and anisole in methylene chloride at temperatures from 0–25 degrees C. or HCl in methanol at 0–25 degrees C.) affords the salt of 12-8. This compound is then utilized as the cyclic secondary amine component as shown above in Schemes 4, 5, 6, 7, 8, 9, 10 and 11. Alternatively, if no functionality is present in the alkyl cyclopentane framework that would be adversely effected by the above mentioned chemistry, then 4-piperidone may be attached directly to the alkyl cyclopentane framework described above, and the chemistry described in this paragraph can be carried out equating the alkyl cyclopentane segment to the group 'P' given in Scheme 12, structures 1 through 7.

SCHEME 13

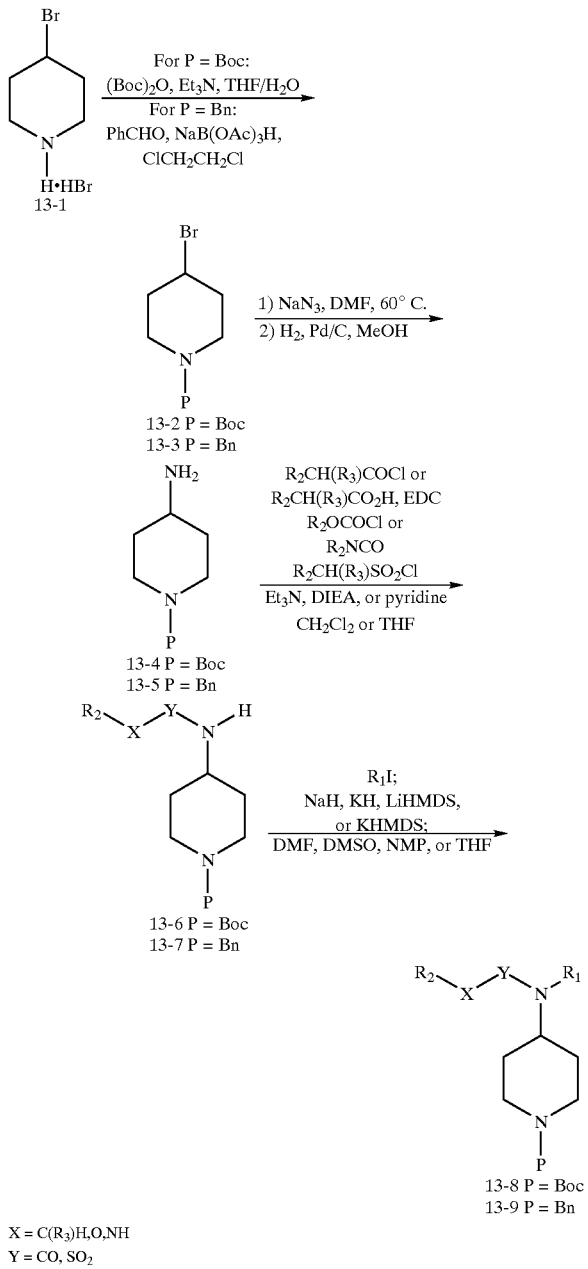

X = C(R₃)H,O,NH
Y = CO, SO₂

Alternate synthetic routes for the preparation of piperidines bearing a 4-substituent containing an amide, carbamate, urea or sulfonamide functional group are given in Scheme 13. Protection of 4-bromopiperidine can be carried out with several protecting groups for nitrogen. For example, using standard conditions, protection with a Boc group gives 13-2, whereas reductive alkylation with benzaldehyde yields the N-benzyl derivative 13-3. Displacement of the bromide with sodium azide in warm to hot DMF provides the 4-azidopiperidine derivative, and reduction of the azide with hydrogen in the presence of a palladium catalyst (for the Boc protected intermediate) or with triphenylphosphine followed by hydrolysis (for N-benzyl protected intermediate) provides the aminopiperidine 13-4 or 13-5. Acylation is then carried out with an acyl chloride (or a carboxylic acid plus an activating agent, such as EDC, DCC, or BOP-Cl) to provide 13-6 or 13-7 as an amide. Alternatively, acylation with a chloroformate provides 13-6 or 13-7 as a carbamate. Treatment of 13-4 or 13-5 with an isocyanate affords 13-6 or 13-7 as a urea. Treatment of 13-4 or 13-5 with a sulfonyl chloride affords 13-6 or 13-7 as a sulfonamide. For each of these reactions, an amine base is employed, such as triethylamine, DIEA, pyridine, or 2,6-lutidine. When X=C(R₃)HCO, OCO, or SO₂ compounds 13-6 and 13-7 may optionally be alkylated by treatment with a base such as sodium hydride, potassium hydride, LiHMDS, KHMDS or NaHMDS followed by treatment with an alkyl iodide, allyl halide, or propargyl halide. Solvents such as DMF, DMSO, N-methylpyrrolidine or TIF are suitable. These procedures provide carbamate, urea, amide or sulfonamide 13-8 and 13-9. Removal of the protecting groups is then carried out as shown in Scheme 12 above, and the resulting 1-unsubstituted piperidines are then utilized as noted in the descriptions for Schemes 4, 5, 6, 7, 8, 9, 10 and 11.

In some cases the order of carrying out the foregoing reaction schemes may be varied to facilitate the reaction or to avoid unwanted reaction products. The following examples are provided for the purpose of further illustration only and are not intended to be limitations on the disclosed invention.

GENERAL

Concentration of solutions was carried out on a rotary evaporator under reduced pressure. Flash chromatography was carried out on silica gel (230–400 mesh). NMR spectra were obtained in CDCl₃ solution unless otherwise noted. Coupling constants (J) are in hertz (Hz). Abbreviations: diethyl ether (ether), triethylamine (TEA), N,N-diisopropylethylamine (DIEA) saturated aqueous (sat'd), room temperature (rt), hour(s) (h), minute(s) (min).

HPLC CONDITIONS

HPLC A. Retention time using the following conditions: Column: YMC ODS A, 5 μ, 4.6×50 mm; Gradient Eluant: 10:90 to 90:10 v/v CH₃CN/H₂O+0.5% TFA over 4.5 min, hold 30 sec; Detection: PDA, 210–400 nm; Flow Rate: 2.5 mL/min.

HPLC B. Retention time using the following conditions: Column: Analytical Sales & Services Advantage HL C18 5 μ 4.6×100 mm column; Gradient Eluant: 10:90 to 90:10 v/v CH₃CN/H₂O+0.5% TFA over 10 min, hold 2 min; Detection: PDA, 200–400 nm; Flow Rate: 2.25 mL/min.

The following are representative examples of the procedures used for the preparation of the piperidines used in the Examples.

PROCEDURE 1

4-(N-(t-Butoxycarbonyl)-N-(ethyl)amino)piperidine
Step A: (1-Benzyloxycarbonylpiperidin-4-yl)isocyanate To a solution of 9.72 g (34.8 mmol) of 1-benzyloxycarbonyl-4-carboxypiperidine in 100 mL of methylene chloride was added 2 drops of DMF and then slowly 3.34 mL (38.3 mmol) of oxalyl chloride. The reaction was stirred at rt for 1 h (gas evolution had stopped) and the volatiles were removed in vacuo followed by evaporation of a portion of toluene.

The above residue was taken up in 100 mL of acetone and slowly added to a solution of 5.66 g (87 mmol) of sodium azide in 25 mL of water and 25 mL of acetone while stirred in an ice bath. The reaction was stirred at 0° C. for 1.5 h and then diluted with ice water and extracted twice with 2×150 mL of toluene. The organic layers were each washed with a portion of brine, dried over sodium sulfate, combined and concentrated to about 100 mL in vacuo with a minimum of heating. The remaining solution was slowly heated to 85° C. for 1.5 h and then concentrated to dryness in vacuo to afford about 9.5 g of crude title product which can be used directly in subsequent reactions.

Step B: 1-Benzyloxycarbonyl-4-(t-butoxycarbonylamino) piperidine

A solution of 3.2 g (12.3 mmol) of (1-benzyloxycarbonylpiperidin-4-yl)isocyanate from Step A in 25 mL of DMF was slowly added to a suspension of $CuCl_3$ in 25 mL of DMF and 12 mL of t-butanol. The reaction was stirred for 24 h and then diluted with water and extracted twice with 1:1 ether:ethyl acetate. The organic layers were each washed with a portion of water and brine, dried over sodium sulfate, combined and concentrated. The residue was purified by FCC eluting with 20% ethyl acetate/hexanes to afford 685 mg of title compound.

$^1$H NMR (400 MHz, $CDCl_3$): δ 1.26 (m, 2 H), 1.42 (s, 9 H), 1.90 (br d, J=12 Hz, 2 H), 2.90 (br t, 2 H), 3.58 (m, 1H), 4.08 (m, 2 H), 4.42 (br s, 1 H), 5.09 (s, 2 H), 7.33 (m,5 H).

Step C: 1-Benzyloxycarbonyl-4-(N-(t-butoxycarbonyl-N-(ethyl)amino)piperidine

To a solution of 476 mg (1.42 mmol) of 1-benzyloxycarbonyl-4-(t-butoxycarbonylamino)piperidine from Step B and 0.24 mL (2.8 mmol) of ethyl iodide in 10 mL of DMF was added 85 mg (2.1 mmol) of 60% sodium hydride in mineral oil. The reaction was stirred for 16 h and was then poured into water and extracted three times with ether. The organic layers were each washed with a portion of water and brine, dried over sodium sulfate, combined and concentrated. The residue was purified by FC eluting with 15% ethyl acetate/hexanes to afford 409 mg of title compound.

$^1$H NMR (400 MHz, $CDCl_3$): δ 1.06 (t, J=7 Hz, 3 H), 1.44 (s, 9 H), 1.5–1.7 (2 m, 4 H), 2.78 (m, 2 H), 3.1 (m, 2 H), 4.10 (m, 1 H), 4.25 (m, 2 H), 5.10 (s, 2 H), 7.33 (m, 5 H).

Step D: 4-(N-(t-Butoxycarbonyl)-N-(ethyl)amino) piperidine

A solution of 400 mg (1.1 mmol) of 1-benzyloxycarbonyl-4-(N-(-t-butoxycarbonyl-N-(ethyl)amino)piperidine from Step C in 4 mL of methanol was hydrogenated with 40 mg of 10% Pd/C under a hydrogen balloon for 16 h. The reaction was filtered and concentrated in vacuo to give the title compound which was used directly in the above reductive alkylations.

PROCEDURE 2

4-(N-Methoxycarbonyl-N-(ethyl)amino)piperidine

Step A: 1-Benzyloxycarbonyl-4-(methoxycarbonylamino)piperidine

To a solution of 1.0 g (3.9 mmol) of (1-benzyloxycarbonylpiperidin-4-yl)isocyanate from Procedure 1, Step A in 10 mL of methanol was added 5 mg (cat) of DMAP. The reaction was stirred under nitrogen at rt for 24 h and then poured into water containing 2 mL of 2N hydrochloric acid and was extracted twice with ethyl acetate. The organic layers were each washed with a portion of brine, dried over sodium sulfate, combined and concentrated to give 1.4 g of the crude title compound which can be used directly in subsequent reactions.

$^1$H NMR (400 MHz, $CDCl_3$): δ 1.32 (m, 2 H), 1.92 (br d, J=10 Hz, 4 H), 2.91 (v br t, 2 H), 3.66 (br s, 3 H+1 H), 4.10 (m, 2 H), 4.58 (br s, 1 H), 5.09 (s, 2 H), 7.33 (m, 5 H).

Step B: 1-Benzyloxycarbonyl-4-(N-methoxycarbonyl(N-ethyl)amino)piperidine

To 82 mg (0.28 mmol) of 1-benzyloxycarbonyl-4-(methoxycarbonylamino)piperidine from Step A and 0.045 mL (0.56 mmol) of ethyl iodide in 4 mL of DMF under nitrogen was added 22 mg (0.56 mmol) of 60% sodium hydride in mineral oil. The reaction was stirred at rt for 1 h and was then poured into water containing 1 mL of 2N hydrochloric acid and extracted twice with ether. The organic layers were each washed with a portion of brine, dried over sodium sulfate, combined and concentrated. The residue was purified by FC eluting with 50% ethyl acetate/hexanes to afford 87 mg of title compound.

$^1$H NMR (400 MHz, $CDCl_3$): δ 1.07 (t, J=7 Hz, 3 H), 1.5–1.8 (m, 4 H), 2.79 (m, 2 H), 3.15 (m, 2 H), 3.68 (s, 3 H), 4.10 (m, 1 H), 4.26 (m, 2 H), 5.10 (s, 2 H), 7.34 (m, 5 H).

Step C: 4-(N-Methoxycarbonyl-N-(ethyl)amino)piperidine

Using essentially the same procedure as in Procedure 1, Step D, 85 mg (0.27 mmol) of 1-benzyloxycarbonyl-4-(N-(methoxycarbonyl)-N-(ethyl)amino)piperidine from Step B was hydrogenated to afford 37 mg of the title compound.

PROCEDURE 3

4-(Dimethylaminocarbonylamino)piperidine

Step A: 1-Benzyloxycarbonyl-4-(dimethylaminocarbonylamino)piperidine

To 0.83 g (3.2 mmol) of (1-benzyloxycarbonylpiperidin-4-yl)isocyanate from Procedure 1, Step A in 10 mL was added 16 mL (32 mmol) of 2 M dimethylamine in THF. The reaction was stirred under nitrogen at rt for 24 h and then poured into water containing 20 mL of 2N hydrochloric acid and was extracted twice with ethyl acetate. The organic layers were each washed with a portion of brine, dried over sodium sulfate, combined and concentrated to give 0.95 g of the crude title compound which can be used directly in subsequent reactions.

$^1$H NMR (400 MHz, $CDCl_3$): δ 1.25 (m, 2 H), 1.95 (br d, J=10 Hz, 2 H), 2.86 (br s, 6 H+2 H), 3.79 (m, 1 H), 4.0–4.25 (m, 3 H), 5.09 (s, 2 H), 7.35 (m, 5 H).

Step B: 4-(Dimethylaminocarbonylamino)piperidine

Using essentially the same procedure as in Procedure 1, Step D, 1.4 g (4.6 mrol) of 1-benzyloxycarbonyl-4-(dimethylaminocarbonylamino)piperidine from Step A was hydrogenated to afford 690 mg of the title compound.

PROCEDURE 4

4-(N-(Benzyloxycarbonyl)-N-(prop-1-yl)amino) piperidine

Step A: 4-Azido-1-t-butoxycarbonylpiperidine

To a solution of 45.3 g (172 mmol) of 4-bromo-1-t-butoxycarbonylpiperidine in 750 mL of DMF was added 22.3 g (343 mmol) of sodium azide and 2.5 g (17 mmol) of sodium iodide. The reaction was stirred at rt for 24 h and then at 60° C. for 4 h. The mixture was poured into water containing 20 mL of sodium bicarbonate and extracted twice with 1:1 ether:hexanes. The organic layers were each washed with a portion of water and brine, dried over sodium sulfate, combined and concentrated. The residue was purified by FC eluting with 5–10% ethyl acetate/hexanes to afford 39 g of title compound having a trace of elimination byproduct.

$^1$H NMR (400 MHz, $CDCl_3$): δ 1.43 (s, 9 H), 1.52 (m, 2 H), 1.85 (m, 2 H), 3.07 (m, 2 H), 3.55 (m, 1 H), 3.78 (m, 2 H).

Step B: 4-Amino-1-t-butoxycarbonylpiperidine

A solution of 4.05 g (17.9 mmol) of 4-azido-1-t-butoxycarbonylpiperidine from Step A in 50 mL of methanol was hydrogenated with 350 mg of 10% Pd/C under a hydrogen balloon for 16 h when the reaction was complete by TLC (10% ethyl acetate/hexanes). The catalyst was filtered off and the volatiles removed in vacuo to give 3.5 g of title compound which was used directly in subsequent reactions.

Step C: 4-Benzyloxycarbonylamino-1-t-butoxycarbonylpiperidine

To a solution of 1.2 g (6.0 mmol) 4-amino-1-t-butoxycarbonylpiperidine from Step B in 40 mL of methylene chloride was added 3.15 mL (18 mmol) of DIPEA and 1.03 mL (7.2 mmol) of benzyl chloroformate while cooled in an ice bath. After 0.5 h the reaction was quenched with aqueous sodium carbonate and extracted three times with methylene chloride. The organic layers were each washed with a portion of brine, dried over sodium sulfate, combined and concentrated. The residue was purified by FC eluting with 25% ethyl acetate/hexanes to afford 1.94 g of title compound.

$^1$H NMR (400 MHz, CDCl$_3$): δ 1.26 (m, 2 H), 1.42 (s, 9 H), 1.90 (br d, J=12 Hz, 2 H), 2.90 (br t, 2 H), 3.58 (m, 1 H), 4.08 (m, 2 H), 4.42 (br s, 1 H), 5.09 (s, 2 H), 7.33 (m, 5 H).

Step D: 4-(N-(Benzyloxycarbonyl)-N-((prop-1-yl)amino)-1-t-butoxycarbonylpiperidine To 110 mg (0.32 mmol) 4-benzyloxycarbonylamino-1-t-butoxycarbonylpiperidine from Step C and 0.16 mL (1.6 mmol) of n-propyl iodide in 2 mL of DMF under nitrogen was added 26 mg (0.65 mmol) of 60% sodium hydride in mineral oil. The reaction was stirred at rt for 16 h and was then poured into water and extracted twice with ether. The organic layers were each washed with a portion of brine, dried over sodium sulfate, combined and concentrated. The residue was purified by FC eluting with 20% ethyl acetate/hexanes to afford 90 mg of title compound.

Step E: 4-(N-(Benzyloxycarbonyl)-N-(prop-1-yl)amino)piperidine di-hydrochloride salt To a solution of 2.4 mmol of HCl in 2 mL of methanol (prepared by the addition of 0.17 mL of acetyl chloride at 0° C. and stirring for 10 min) was added 90 mg of 4-(N-(benzyloxycarbonyl)-N-(prop-1-yl)amino)-1-t-butoxycarbonylpiperidine. The mixture was stirred at rt for 16 h at which time the reaction was complete by TLC (20% ethyl acetate/hexanes) and was evaporated to dryness in vacuo to afford 75 mg of the title compound as the di-hydrochloride salt and which was used in the above reductive alkylations.

PROCEDURE 5

4-(N-(Benzyloxycarbonyl)-N-(allyl)amino) piperidine hydrochloride

Step A: 4-(N-(Benzyloxycarbonyl)-N-(allyl)amino)-1-(tert-butoxycarbonyl)piperidine Sodium hydride (47 mg of 60% oil dispersion, 1.2 mmol) was added to a solution of 4-(benzyloxycarbonylamino)-1-(tert-butoxycarbonyl)piperidine (200 mg, 0.598 mmol) from Procedure 4, Step C and allyl bromide (0.251 mL, 351 mg, 2.9 mmol) in 2.0 mL of DMF, and the reaction was stirred overnight at rt. The reaction mixture was poured into 20 mL of water and extracted with 3×20 mL of ethyl ether. The combined organic layers were washed with 30 mL of brine, dried over sodium sulfate, and evaporated. The crude product was purified by FC on silica gel, eluting with 20% ethyl acetate in hexane, to give 246 mg of the title compound as a viscous oil.

$^1$H NMR (400 MHz, CD$_3$OD): δ 7.38–7.26 (m, 5 H), 5.81 (ddt, 1 H, J=17, 10, and 5 Hz), 5.18–5.05 (m, 4 H), 4.12 (bd, 2 H, J=12 Hz), 3.98 (bs, 1 H), 3.86 (bd, 2 H, J=5 Hz), 2.75 (bs, 2 H), 1.74–1.63 (m, 4 H). MS (ESI): m/z=275 (M-99, 100%).

Step B: 4-(N-(Benzyloxycarbonyl)-N-(allyl)amino) piperidine hydrochloride

Acetyl chloride (0.467 mL, 516 mg, 6.57 mmol) was added to 2.0 mL of methanol at 0° C. and the mixture was stirred for 10 min to give a solution of HCl. 4-(N-(Benzyloxycarbonyl)allylamino)-1-(tert-butoxycarbonyl) piperidine (123 mg, 0.33 mmol) was then added and the resulting solution was stirred for 1 h at 0° C. and 1 h at rt. The solution was evaporated to give the title compound as a crystalline solid in quantitative yield.

$^1$H NMR (400 MHz, CD$_3$OD): δ 7.39–7.28 (m, 5 H), 5.84 (ddt, 1 H, J=17, 10, 5 Hz), 5.21–5.10 (m, 4 H), 4.10–3.98 (m, 1 H), 3.90 (d, 2 H, J=5 Hz), 3.43 (bd, 2 H, J=13 Hz), 3.04 (bt, 2H, J=13 Hz), 2.18–2.02 (m, 2H), 1.93 (d, 2H, J=13 Hz). MS (CI): m/z=275 (M+1, 100%).

PROCEDURE 6

4-(N-(4-Nitrobenzyloxycarbonyl)-N-(allyl)amino) piperidine hydrochloride

Step A: 1-(tert-Butoxycarbonyl)-4-(N-(4-nitrobenzyloxycarbonyl)-N-(allyl)amino)piperidine Allylamine (0.45 mL, 0.34 g, 6.0 mmol), acetic acid (0.300 mL, 315 mg, 5.24 mmol), and 3 Å molecular sieves (2.00 g) were added to a solution of 1-(tert-butoxycarbonyl)-4-piperidone (1.00 g, 5.01 mmol) in 14 mL of 1,2-dichloroethane. After stirring 0.5 h at rt, sodium triacetoxyborohydride (1.62 g, 7.6 mmol) was added in two portions 5 min apart. After an additional 3 h, the mixture was partitioned between 30 mL of ethyl acetate and 20 mL of saturated aqueous sodium bicarbonate. The aqueous layer was extracted with 30 mL of ethyl acetate and the organic layers were washed in succession with 20 mL of brine, combined, dried over sodium sulfate, and evaporated to give 1.20 g of crude 4-(allylamino)-1-(tert-butoxycarbonyl) piperidine as a yellow syrup.

A portion of the crude 4-(allylamino)-1-(tert-butoxycarbonyl)piperidine (400 mg, 1.66 mmol) was dissolved in 10 mL of dichloromethane and treated with N,N-diisopropylethylamine (0.700 mL, 519 mg, 4.0 mmol) and 4-nitrobenzyl chloroformate (392 mg, 1.82 mmol). After stirring 3 h at rt, the mixture was diluted with 30 mL of ethyl acetate and washed with 15 mL each of 2 N aqueous HCl, saturated aqueous sodium bicarbonate, and brine. The organic layer was dried over sodium sulfate, and evaporated. The residue was purified by FC on silica gel, eluting with 30% ethyl acetate in hexane, to give 572 mg of the title compound as a colorless syrup.

$^1$H NMR (400 MHz, CDCl$_3$): δ 8.22 (d, 2 H, J=8 Hz), 7.50 (d, 2 H, J=8 Hz), 5.80 (ddt, 1 H, J=17, 10, 5 Hz), 5.23 (s, 2 H), 5.18–5.09 (m, 2 H), 4.27–4.08 (m, 3 H), 3.89–3.79 (m, 2 H), 2.79–2.66 (m, 2 H), 1.74–1.52 (m, 4 H), 1.46 (s, 9 H). MS (ESI): m/z=420 (M+1, 27%), 437 (M+1+NH$_3$, 100%).

Step B: 4-(N-(4-Nitrobenzyloxycarbonyl)-N-(allyl)amino) piperidine hydrochloride The title compound was prepared according to the procedure of Procedure 4, Step E, replacing 4-(N-(benzyloxycarbonyl)-N-(ethyl)amino)-1-(tert-butoxycarbonyl)piperidine with 1-(tert-butoxycarbonyl)-4-(N-(4-nitrobenzyloxycarbonyl)-N-(allyl)amino)piperidine.

$^1$H NMR (400 MHz, CD$_3$OD): δ 8.24 (d, 2 H, J=8 Hz), 7.60 (d, 2 H, J=8 Hz), 5.87 (ddt, 1 H, J=17, 10, 5 Hz), 5.27 (s, 2 H), 5.23–5.13 (m, 2 H), 4.14–3.94 (m, 1 H), 3.94 (d, 2 H, J=5 Hz), 3.45 (d, 2 H, J=13 Hz), 3.06 (t, 2 H, J=13 Hz), 2.20–2.03 (m, 2 H), 2.02–1.90 (m, 2 H). MS (ESI): m/z=320 (M+1, 93%).

PROCEDURE 7

The following substituted piperidines were prepared following the procedures described in Procedure 2 but substituting the appropriate alcohol and/or alkylating agent in Step A and B.

4-(N-(Methoxycarbonyl)-N-(hex-1-yl)amino)piperidine 4-(N-(Methoxycarbonyl)-N-(3,5,5-trimethylhex-1-yl)amino)piperidine 4-(N-(Ethoxycarbonyl)-N-(cyclohexylmethyl)amino)piperidine

PROCEDURE 8

The following substituted piperidines were prepared following the procedures described in Procedure 4 but substituting the appropriate alkyl bromide or iodide for n-propyl iodide in Step D.

4-(N-(Benzyloxycarbonyl)-N-(methyl)amino)piperidine hydrochloride 4-(N-(Benzyloxycarbonyl)-N-(2-methylprop-1-yl)amino)piperidine hydrochloride 4-(N-(Benzyloxycarbonyl)-N-(ethyl)amino)piperidine hydrochloride 4-(N-(Benzyloxycarbonyl)-N-(prop-2-yl)amino)piperidine hydrochloride 4-(N-(Benzyloxycarbonyl)-N-(cyclopropylmethyl)amino)piperidine hydrochloride 4-(N-(Benzyloxycarbonyl)-N-(1-methylprop-1-yl)amino)piperidine hydrochloride

PROCEDURE 9

The following substituted piperidines were prepared following the procedures described in Procedure 6 but substituting the appropriate alkyl amine and acylating agent in Step A.

4-(N-(4-Nitrobenzyloxycarbonyl)-N-(propargyl)amino)piperidine hydrochloride 4-(N-(3-Nitrobenzyloxycarbonyl)-N-(propargyl)amino)piperidine hydrochloride 4-(N-(2-Nitrobenzyloxycarbonyl)-N-(propargyl)amino)piperidine hydrochloride 4-(N-(4-Nitrobenzylaminocarbonyl)-N-(allyl)amino)piperidine hydrochloride 4-(N-(3-Nitrobenzylaminocarbonyl)-N-(allyl)amino)piperidine hydrochloride 4-(N-(2-Nitrobenzylaminocarbonyl)-N-(allyl)amino)piperidine hydrochloride 4-(N-(4-Nitrobenzylcarbonyl)-N-(allyl)amino)piperidine hydrochloride 4-(N-(3-Nitrobenzylcarbonyl)-N-(allyl)amino)piperidine hydrochloride 4-(N-(Benzyloxycarbonyl)-N-(prop-1-yl)amino)piperidine hydrochloride 4-(N-(Phenylcarbonyl)-N-(prop-1-yl)amino)piperidine hydrochloride 4-(N-(Benzylcarbonyl)-N-(prop-1-yl)amino)piperidine hydrochloride 4-(N-(Cyclohexyloxycarbonyl)-N-(prop-1-yl)amino)piperidine hydrochloride 4-(N-(2-Phenyleth-1-yloxycarbonyl)-N-(prop-1-yl)amino)piperidine hydrochloride 4-(N-(3-Phenylprop-1-yloxycarbonyl)-N-(prop-1-yl)amino)piperidine hydrochloride 4-(N-(4-Phenylbenzyloxycarbonyl)-N-(prop-1-yl)amino)piperidine hydrochloride 4-(N-(2-Naphthylmethyloxycarbonyl)-N-(prop-1-yl)amino)piperidine hydrochloride 4-(N-(1-Naphthylmethyloxycarbonyl)-N-(prop-1-yl)amino)piperidine hydrochloride 4-(N-(4-Methylbenzyloxycarbonyl)-N-(prop-1-yl)amino)piperidine hydrochloride 4-(N-(4-Trifluoromethylbenzyloxycarbonyl)-N-(prop-1-yl)amino)piperidine hydrochloride 4-(N-(Butyloxycarbonyl)-N-(prop-1-yl)amino)piperidine hydrochloride 4-(N-(Benzylaminocarbonyl)-N-(prop-1-yl)amino)piperidine hydrochloride 4-(N-(4-Fluorobenzyloxycarbonyl)-N-(prop-1-yl)amino)piperidine hydrochloride 4-(N-(3-Fluorobenzyloxycarbonyl)-N-(prop-1-yl)amino)piperidine hydrochloride 4-(N-(2-Fluorobenzyloxycarbonyl)-N-(prop-1-yl)amino)piperidine hydrochloride 4-(N-(4-Chlorobenzyloxycarbonyl)-N-(prop-1-yl)amino)piperidine hydrochloride 4-(N-(3-Chlorobenzyloxycarbonyl)-N-(prop-1-yl)amino)piperidine hydrochloride 4-(N-(2-Chlorobenzyloxycarbonyl)-N-(prop-1-yl)amino)piperidine hydrochloride 4-(N-(3,4-Difluorobenzyloxycarbonyl)-N-(prop-1-yl)amino)piperidine hydrochloride 4-(N-(2,4-Difluorobenzyloxycarbonyl)-N-(prop-1-yl)amino)piperidine hydrochloride 4-(N-(3,5-Difluorobenzyloxycarbonyl)-N-(prop-1-yl)amino)piperidine hydrochloride 4-(N-(2,6-Difluorobenzyloxycarbonyl)-N-(prop-1-yl)amino)piperidine hydrochloride 4-(N-(3,4,5-Trifluorobenzyloxycarbonyl)-N-(prop-1-yl)amino)piperidine hydrochloride 4-(N-(3,4-Dichlorobenzyloxycarbonyl)-N-(prop-1-yl)amino)piperidine hydrochloride 4-(N-(4-Cyanobenzyloxycarbonyl)-N-(prop-1-yl)amino)piperidine hydrochloride 4-(N-(4-Cyano-3-fluorobenzyloxycarbonyl)-N-(prop-1-yl)amino)piperidine hydrochloride

PROCEDURE 10

The following set of 70 substituted piperidines were prepared as their di-TFA salts following the procedures described in Procedure 6 but substituting the appropriate alkyl amine and acylating agent in Step A and using TFA at rt in Step B.

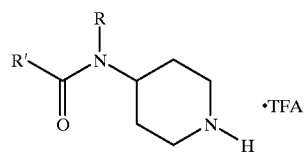

R=
Methyl
Ethyl
n-Propyl
n-Butyl
Allyl
Cyclopropylmethyl
2-Methylcycloprop-1-yl
R'=
Benzyloxy
4-Nitrobenzyloxy
2-Phenyleth-1-yloxy
2-(4-Nitrophenyl)eth-1-yloxy
Benzylamino
4-Nitrobenzylamino
2-Phenyleth-1-yl
2-(4-Nitrophenyl)eth-1-yl
Phenoxymethyl
4-Nitrophenoxymethyl

EXAMPLE 1

(1-(RS and/or SR)-3-(SR)-((4-(N-(Benzyloxycarbonyl)-N-(allyl)amino)piperidin-1-yl)methyl)-4-(SR)-phenylcyclopent-1-yl)acetic acid hydrochloride salt and (1-(SR and/or RS)-3-(SR)-((4-(N-(benzyloxycarbonyl)-N-(allyl)amino)piperidin-1-yl)methyl)-4-(SR)-phenylcyclopent-1-yl)acetic acid hydrochloride salt Step A: Methyl (+−)-trans-4-methylene-2-phenylcyclopentanoate A mixture of methyl trans-cinnamate (5.0 g, 31 mmol), tetrakis(triphenylphosphine) palladium(0) (2.6 g, 2.3 mmol), 1,2-bis(diphenylphosphino)ethane (0.70 g, 1.8 mmol) and 2-((trimethylsilyl)methyl)prop-2-en-1-yl acetate (6.90 g, 37 mmol) in THF (60 mL) under argon was heated to reflux for 4 h. An additional aliquot of 2-((trimethylsilyl)methyl)prop-2-en-1-yl acetate (3.40 g) was added and the reaction was continued for another 16 h. The volatiles were then removed in vacuo and the residue was purified by FC (10% ethyl acetate in hexanes) to afford the title compound (6.2 g).

$^1$H NMR, (CDCl$_3$) δ: 2.52 (m, 1 H), 2.68 (m, 1 H), 2.75–2.9 (m, 2 H), 2.95 (ddd, 1 H), 3.45 (ddd, 1 H), 3.57 (s, 3 H), 4.92 (m, 2 H), 7.15–7.3 (m, 5 H).

Step B: (+−)-trans-1-Hydroxymethyl-4-methylene-2-phenylcyclopentane

Method A:

To a solution of methyl (+−)-trans-4-methylene-2-phenylcyclopentanoate (5.0 g, 23 mmol) from Step A in THF (30 mL) under nitrogen was added dropwise over 10 min 1M lithium aluminum hydride (LAH) in THF (23 mL). After 2 h at rt, the excess LAH was quenched by dropwise addition of ethyl acetate and the reaction was then poured into dilute aq. HCl. The mixture was extracted twice with ether and the organic layers were washed with brine, dried over sodium sulfate, combined and concentrated. The residue was purified by FC (20–30% ethyl acetate in hexanes) to afford the title product (4.5 g) as a white solid.

$^1$H NMR (CDCl$_3$) δ: 2.22 (m, 1 H), 2.33 (tq, 1 H), 2.48 (tq, 1 H), 2.62 (br ddq, 1 H), 2.76 (br ddq, 1 H), 2.91 (ddd, 1 H), 3.55 (dABq, 2 H), 4.87 (m, 2 H), 7.15–7.3 (m, 5 H).

Method B:

Step B1: (+−)-trans-4-Methylene-2-phenylcyclopentanoic acid

To a solution of methyl (+−)-trans-4-methylene-2-phenylcyclopentanoate prepared as in Step A (28.4 g, 131 mmol) in methanol (400 mL) was added 5N sodium hydroxide (131 mL, 656 mmol). The reaction was heated at 65° C. for 1 h then cooled and concentrated. The residue was diluted with water, acidified with 2M hydrochloric acid and extracted twice with methylene chloride. The organic layers were each washed with brine, dried over sodium sulfate, combined and concentrated in vacuo to give the crude title acid (27.2 g) which was used directly in Step B.

Step B2: (+−)-trans-1-Hydroxymethyl-4-methylene-2-phenylcyclopentane

To a solution of (+−)-trans-4-methylene-2-phenylcyclopentanoic acid (26 g, 129 mmol) from Step B1 in THF (600 mL) under nitrogen at −10° C. was added dropwise over 15 min 1M lithium aluminum hydride (LAH) in THF (193 mL, 193 mmol). After 16 h at rt, the excess LAH was quenched by dropwise addition of acetone and the reaction was then poured into dilute aq. HCl. The mixture was extracted twice with ether and the organic layers were washed with brine, dried over sodium sulfate, combined and concentrated. The residue was purified by FC (20% ethyl acetate in hexanes) to afford the title product (23.8 g) which was the same as in Method A.

Step C: (+−)-trans-3-Hydroxymethyl-4-phenylcyclopentan-1-one

Into a solution of (+−)-trans-1-hydroxymethyl-4-methylene-2-phenylcyclopentane from Step B (22.7 g, 121 mmol) in methanol (200 mL) cooled in a dry ice/acetone bath was bubbled ozone until the blue color persisted. The excess ozone was removed with a stream of nitrogen and then dimethylsulfide (20 mL) was added. After 10 min, the bath was removed and the reaction was allowed to warm to rt over 16 h. The volatiles were removed in vacuo and the residue was purified by FC (15–30% ethyl acetate in hexanes) to give the title compound (22.1 g).

$^1$H NMR (CDCl$_3$) δ: 2.2–2.5 (m, 4 H), 2.71 (dd, 1 H), 3.28 (m, 1 H), 3.65 (dABq, 2 H), 7.2–7.4 (m, 5 H).

Step D: (+−)-trans-3-t-Butyldimethylsilyloxymethyl-4-phenylcyclopentan-1-one

Method A:

To a solution of (+−)-trans-3-hydroxymethyl-4-phenylcyclopentan-1-one from Step C (5.0 g, 24 mmol) in methylene chloride (100 mL) was added t-butyldimethylsilyl chloride (11.5 g, 48 mmol) and DIPEA (8.6 mL, 48 mmol). The reaction was stirred at rt for 16 h, poured into dilute aq. HCl and extracted twice with ether. The organic layers were washed with brine, dried over sodium sulfate, combined and concentrated. The residue was purified by FC (5% ethyl acetate in hexanes) to afford the title compound (6.5 g) as a oil.

$^1$H NMR (CDCl$_3$) δ: −0.01 and −0.03 (2 s, 6 H), 0.86 (s, 9 H), 2.2–2.5 (m, 4 H), 2.71 (dd, 1 H), 3.28 (m, 1 H), 3.55 (dABq, 2 H), 7.23 (m, 3 H), 7.34 (m, 2 H).

Method B:

Step B1: (+−)-trans-1-t-Butyldimethylsilyloxymethyl-4-methylene-2-phenylcyclopentane To a solution of (+−)-trans-1-hydroxymethyl-4-methylene-2-phenylcyclopentane from Step B (2.5 g, 13.3 mmol) in methylene chloride (50 mL) was added t-butyldimethylsilyl chloride (3.0 g, 20 mmol) and DIPEA (4.7 mL, 27 mmol). The reaction was stirred at rt for 16 h, poured into dilute aq. HCl and extracted twice with ether. The organic layers were washed with brine, dried over sodium sulfate, combined and concentrated. The residue was purified by FC (5% ethyl acetate in hexanes) to afford the title product (4.2 g) as a oil.

$^1$H NMR (CDCl$_3$) δ: −0.04 and −0.05 (2 s, 6 H), 0.85 (s, 9 H), 2.22 (m, 1 H), 2.33 (tq, 1 H), 2.48 (tq, 1 H), 2.62 (br ddq, 1 H), 2.76 (br ddq, 1 H), 2.91 (ddd, 1 H), 3.45 (dABq, 2 H), 4.87 (m, 2 H), 7.15–7.3 (m, 5 H).

Step B2: (+−)-trans-1-t-Butyldimethylsilyloxymethyl-4-oxo-2-phenylcyclopentane

Into a solution of (+−)-trans-1-t-butyldimethylsilyloxymethyl-4-methylene-2-phenylcyclopentane from Step B1 (2.2 g, 7.3 mmol) in methanol (100 mL) cooled in a dry ice/acetone bath was bubbled ozone until the blue color persisted. The excess ozone was removed with a stream of nitrogen and then dimethylsulfide (5 mL) was added. After 10 min, the bath was removed and the reaction was allowed to warm to rt over 2 h. The volatiles were removed in vacuo and the residue was purified by FC (15–30% ethyl acetate in hexanes) to give the title compound (1.9 g) which was the same as in Method A.

Step E: Ethyl (E and Z)-3-(SR)-t-butyldimethylsilyloxymethyl-4-(SR)phenylcyclopentylideneacetate To a solution of 60% sodium hydride in mineral oil (0.091g, 2.3 mmol) in THF (1 mL) was added triethyl phosphonoacetate (0.564 mL, 0.637 g, 2.8 mmol). The reaction was stirred at rt for 30 min. To this solution was added a solution of (+−)-trans-3-t-butyldimethylsilyloxymethyl-4-phenylcyclopentan-1-one from Step D (0.173 g, 0.57 mmol) in THF (1 mL). The reaction was stirred at rt for 2 days, diluted with chloroform, poured into water and extracted three times with chloroform. The organic layers were combined, washed with brine, dried over sodium sulfate, filtered and concentrated in vacuo. The residue was purified by FC (10% ethyl acetate in hexanes) to afford the title compound as a 1:1 mixture of E:Z double bond isomers (0.193 g) as an oil.

$^1$H NMR (CDCl$_3$): δ −0.01(s, 3 H), −0.03 (s, 3 H), 0.86 (s, 9 H), 1.23 and 1.27 (2 t, 3 H), 2.15–2.26 (m, 1 H), 2.50–2.65 (m, 0.5 H), 2.65–2.74 (m, 1.5 H), 2.77–2.95 (m, 1 H), 2.95–3.05 (m, 1 H), 3.17–3.26 (m, 0.5 H), 3.38–3.46 (m, 1.5 H), 3.54–3.61 (m, 1 H), 4.13 and 4.17 (2 q, 2 H), 5.50–5.82 (m, 1 H), 7.15–7.24 (m, 3 H), 7.25–7.32 (m, 2 H).

Step F: Ethyl (1-(RS and SR)-3-(SR)-hydroxymethyl-4-(SR)-phenylcyclopent-1-yl)acetate A solution of ethyl (E and Z)-3-(SR)-t-butyldimethylsilyloxymethyl-4-(SR)phenylcyclopentylideneacetate from Step E (190 mg) in methanol (5 mnL) was hydrogenated with 20% palladium hydroxide on carbon (0.040 g) at 45 psi for 12 h. The catalyst was filtered off and the volatiles removed in vacuo to give 0.128 g of residue. The residue was purified by FC (20% ethyl acetate in hexanes) to afford the title compound as a 3:1 mixture of epimers at the cyclopentyl C-1 (0.099 g).

$^1$H NMR (CDCl$_3$): δ 1.10–1.25 (m, 0.5 H), 1.23 (t, 3 H), 1.60–1.71 (m, 0.5 H), 1.74–1.88 (m, 1 H), 1.97–2.07 (m, 1 H), 2.13–2.30 (m, 2 H), 2.33–2.43 (m, 2.5 H), 2.55–2.67 (m, 0.5 H), 3.18–3.28 (m, 0.5 H), 3.84 (dd, 0.5 H), 3.42–3.52 (m, 1 H), 3.56–3.65 (m, 1 H), 4.10 (q, 2 H), 7.13–7.31 (m, 5 H).

Step G: Ethyl (1-(RS and SR)-3-(SR)-formyl-4-(SR)-phenylcyclopent-1-yl)acetate

To a solution of oxalyl chloride (0.091 mL, 0.133 g, 1.05 mmol) in methylene chloride (1.5 mL) at −70° C. was added dropwise DMSO (0.149 mL, 0.164 g, 2.09 mmol). After 10 min, a solution of ethyl (1-(RS and SR)-3-(SR)-hydroxymethyl-4-(SR)-phenylcyclopent-1-yl)acetate from Step F (0.055 g, 0.209 mmol) in methylene chloride (0.5 mnL) was added dropwise. The reaction was stirred at −70° C. for 1 h and then TEA (0.438 mL, 0.318 g, 3.14 mmol) was added. The reaction mixture was allowed to warm to rt for 10 min and then diluted with methylene chloride, poured into water, and extracted three times with methylene chloride. The organic layers were combined, washed with brine, dried over sodium sulfate, filtered and concentrated in vacuo. The crude title compound (0.047 g) was used directly in Step H.

Step H: Ethyl (1-(RS and SR)-3-(SR)-((4-(N-(benzyloxycarbonyl)-N-(allyl)amino)piperidin-1-yl)methyl)-4-(SR)-phenylcyclopent-1-yl)acetate To a solution of ethyl (1-(RS and SR)-3-(SR)-formyl-4-(SR)-phenylcyclopent-1-yl)acetate from Step G (0.047 g, 0.18 mmol) in 1,2-dichloroethane (2 mL) was added 4-(N-(benzylaminocarbonyl)-N-(prop-1-yl)amino)piperidine hydrochloride (0.084 g, 0.27 mmol) and DIPEA (0.047 mL, 0.35 g, 0.27 mmol). After 10 min, sodium triacetoxyborohydride (0.077 g, 0.36 mmol) was added and the reaction mixture was stirred at rt for 15 min. The reaction mixture was diluted with methylene chloride, poured into aqueous sodium bicarbonate and extracted three times with methylene chloride. The organic layers were combined, washed with brine, dried over sodium sulfate, filtered and concentrated in vacuo. The residue was purified by FC (20% ethyl acetate in hexanes) to afford the title compound as a mixture of epimers at the cyclopentyl C-1 (0.069 g).

MS (ESI, AcCN/TFA-NH$_4$Formate): m/z 519 (M +1).

Step I: (1-(RS and/or SR)-3-(SR)-((4-(N-(Benzyloxycarbonyl)-N-(allyl)amino)piperidin-1-yl)methyl)-4-(SR)-phenylcyclopent-1-yl)acetic acid and (1-(SR and/or RS)-3-(SR)-( (4-(N-(benzyloxycarbonyl)-N-(allyl)amino)piperidin-1-yl)methyl)-4-(SR)-phenylcyclopent-1-yl)acetic acid To a solution of ethyl (1-(RS and SR)-3-(SR)-((4-(N-(benzyloxycarbonyl)-N-(allyl)amino)piperidin-1-yl)methyl)-4-(SR)-phenylcyclopent-1-yl)acetate from Step H (0.029 g, 0.055 nmmol) in THF (0.5 mL) was added 1.3M sodium hydroxide solution (0.131 mL, 0.166 mmol). After 30 min no reaction had occurred, thus 1.0M lithium hydroxide solution (0.166 mL, 0.166 mmol) was added and the reaction mixture was stirred for 12 h. The reaction mixture was acidified using 2N hydrochloric acid until the pH=2, diluted with methylene chloride, poured into water and extracted three times with methylene chloride. The organic layers were combined, washed with brine, dried over sodium sulfate, filtered and concentrated in vacuo. The residue was purified by Prep TLC eluting with 93:5:1:1 methylene chloride/methanol/ammonium hydroxide/water to give partial separation into two fractions of the two diastereomeric racemic title products, higher R$_f$(0.0022 g) and a mixture of higher and lower R$_f$ (0.0094 g). The stereochemistries for each were not assigned.

Step J: (1-(RS or SR)-3-(SR)-((4-(N-(Benzyloxycarbonyl)-N-(allyl)amino)piperidin-1-yl)methyl)-4-(SR)-phenylcyclopent-1-yl)acetic acid hydrochloride salt and (1-(SR or RS)-3-(SR)-((4-(N-(benzyloxycarbonyl)-N-(allyl)amino)piperidin-1-yl)methyl)-4-(SR)-phenylcyclopent-1-yl)acetic acid hydrochloride salt The individual products from Step I were each taken up in 1:1 methylene chloride:ether (0.5 mL) and 1N hydrochloric acid in diethyl ether was added (0.013 mL, 0.013 mmol) to the higher R$_f$ sample and (0.057 mL, 0.057 mmol) to the mixture sample. The volatiles were removed under a stream of nitrogen to give the title racemic compounds as white solids.

(higher R$_f$): MS (ESI, AcCN/TFA-NH$_4$Formate): m/z 491 (M +1); (mixture): MS (ESI, AcCN/TFA-NH$_4$Formate): m/z 491 (M+1).

EXAMPLE 2

2-(RS or SR)-(1-(RS and/or SR)-3-(SR)-((4-(N-(Benzyloxycarbonyl)-N-(allyl)amino)piperidin-1-yl)methyl)-4-(SR)-phenylcyclopent-1-yl)-propionic acid hydrochloride salt and 2-(SR or RS)-(1-(RS and/or SR)-3-(SR)-((4-(N-(benzyloxycarbonyl)-N-(allyl)amino)piperidin-1-yl)methyl)-4-(SR)-phenylcyclopent-1-yl)-propionic acid hydrochloride salt Step A: Ethyl (1-(RS and SR)-3-(SR)-t-butyldimethylsilyloxymethyl-4-(SR)-phenylcyclopent-1-yl)acetate To a solution of ethyl (1-(RS and SR)-3-(SR)-hydroxymethyl-4-(SR)-phenylcyclopent-1-yl)acetate from Example 1, Step F (0.057 g, 0.22 mmol) in methylene chloride (5 mL) was added DIPEA (0.113 mL, 0.084 g, 0.65 mmol) and t-butyldimethylsilyl chloride (0.036 g, 0.24 mmol). The reaction was stirred at rt for 12 h. TLC analysis indicated that the reaction was not complete. Additional DIPEA (0.226 mL, 0.17 g, 1.3 mmol) and t-butyldimethylsilyl chloride (0.072 g, 0.480) was added. The reaction was stirred at rt for another 48 h, poured into aqueous sodium bicarbonate, and extracted three times with methylene chloride. The organic layers were combined, washed with brine, dried over sodium sulfate, filtered and concentrated. The residue was purified by FC (5% ethyl acetate in hexanes) to afford the title product (0.074 g) as a oil.

MS (EI, 80% MeOH/CH$_2$Cl$_2$): m/z 319 (M-57 (t-butyl)).

Step B: Ethyl 2-(RS and SR)-(1-(RS and SR)-3-(SR)-t-butyldimethylsilyloxymethyl-4-(SR)-phenylcyclopent-1-yl)propionate To a solution of THF (1 mL) at −78° C. was added diisopropylamine (0.032 mL, 0.023 g, 0.23 mmol) and 2.5 M n-butyllithium solution in hexanes (0.091 mL, 0.23 mmol) and the reaction mixture was stirred for 5 min. To this solution was added a solution of ethyl (1-(RS and SR)-3-(SR)-t-butyldimethylsilyloxymethyl-4-(SR)-phenylcyclopent-1-yl) acetate from Step A (0.057 g, 0.16 mmol) in THF (1 mL) and the reaction mixture was stirred at −78° C. for 45 min. To this solution was then added iodomethane (0.030 mL, 0.069 g, 0.49 mmol). The reaction mixture was stirred for 2.5 h as it was allowed to warm to rt and was then diluted with diethyl ether, poured into water, extracted three times with diethyl ether. The organic layers were combined, washed with brine, dried over sodium sulfate, filtered and concentrated to afford the crude title compound (0.070 g). The residue was purified by FC (3% ethyl acetate in hexanes) to afford the title product (0.046 g) as an oil.

MS (EI, 80% MeOH/CH$_2$Cl$_2$): m/z 333 (M-57 (t-butyl)).

Step C: Ethyl 2-(RS and SR)-(1-(RS and SR)-3-(SR)-hydroxymethyl-4(SR)-phenylcyclopent-1-yl)propionate To a solution of ethyl 2-(RS and SR)-(1-(RS and SR)-3-(SR)-t-butyldimethylsilyloxymethyl-4-(SR)-phenylcyclopent-1-yl)propionate from Step B (0.039 g, 0.100 mmol) in THF (1 mL) was added a 1.0 M solution of tetrabutylammonium fluoride in THF (0.151 mL, 0.151 mmol) and the reaction mixture was stirred at rt for 1 h. Additional tetrabutylammonium fluoride solution (0.100 mL, 0.100 mmol) was added and the reaction mixture was stirred for an additional 2 h when TLC analysis indicated that the reaction was complete. The reaction mixture was diluted with ethyl acetate, poured into 5% aqueous hydrogen chloride solution, extracted three times with ethyl acetate, combined organic layers, washed with brine, dried over sodium sulfate and concentrated. The residue was purified by FC (20% ethyl acetate in hexanes) to afford the title product (0.022 g).

$^1$H NMR (CDCl$_3$): δ 1.20, 1.26, 1.28 and 1.29 (4 t, 3 H), 1.20 (m, 3.5 H), 1.71–1.86 (m, 0.5 H), 1.88–1.99 (m, 1.5 H), 2.08–2.18 (m, 0.5 H), 2.19–2.29 (m, 2 H), 2.32–2.47 (m, 2 H), 2.73–2.80 (m, 0.5 H), 2.82–2.88 (m, 0.5 H), 3.50–3.60 (m, 1 H), 3.63–3.71 (m, 1 H), 4.13–4.19 (m, 2 H), 7.20–7.33 (m, 5 H).

Step D: 2-(RS or SR)-(1-(RS and/or SR)-3-(SR)-((4-(N-(Benzyloxycarbonyl)-N-(allyl)amino)piperidin-1-yl)methyl)-4-(SR)-phenylcyclopent-1-yl)propionic acid hydrochloride salt and 2-(RS or SR)-(1-(SR and/or RS)-3-(SR)-((4-(N-(benzyloxycarbonyl)-N-(allyl)amino)piperidin-1-yl)methyl)-4-(SR)-phenylcyclopent-1-yl)propionic acid hydrochloride salt Using essentially the same procedures as in Example 1, Steps G–J, the synthesis of the title compounds was achieved. Following Step I, partial separation of the four possible racemic diastereomers into three fractions was achieved by Prep TLC eluting with 93:5:1:1 methylene chloride/methanol/ammonium hydroxide/water, but the stereochemistries for each isomer were not assigned.

MS (ESI, AcCN/TFA-NH$_4$Formate): m/z 506 (M+1) (for each isomer(s)).

EXAMPLE 3

2-(RS or SR)-(1-(RS and SR)-3-(SR)-((4-(N-(Benzyloxycarbonyl)-N-(allyl)amino)piperidin-1-yl)methyl)-4-(SR)-phenylcyclopent-1-yl)-4-methylpentanoic acid hydrochloride salt Step A: Ethyl 2-(RS and SR)-(1-(RS and SR)-3-(SR)-t-butyldimethylsilyloxymethyl-4-(SR)-phenylcyclopent-1-yl)-4-methylpent-4-enoate To THF (5 mL) at −78° C. was added 1.5 M lithium diisopropylamide mono(tetrahydrofuran) solution in cyclohexane (0.662 mL, 0.99 mmol). To this solution was then added a solution of ethyl (1-(RS and SR)-3-(SR)-t-butyldimethylsilyloxymethyl-4-(SR)-phenylcyclopent-1-yl) acetate from Example 2, Step A (0.280 g, 0.76 mmol) in THF (1 mL) and the reaction mixture was stirred at −78° C. for 1 h. To this solution was then added 3-bromo-2-methylprop-1-ene (0.235 mL, 0.309 g, 2.3 mmol). The reaction mixture was stirred for 1.5 h as it was allowed to warm to rt and was then diluted with diethyl ether, poured into water and extracted three times with diethyl ether. The organic layers were combined, washed with brine, dried over sodium sulfate, filtered and concentrated. The residue was purified by FC (3% ethyl acetate in hexanes) to afford the title product (0.256 g) as an oil.

$^1$H NMR (CDCl$_3$): δ −0.02, −0.03, −0.03 and −0.04 (4 s, 6 H), 0.86 and 0.84 (2 s, 9 H), 1.20 and 1.24 (2 t, 3 H), 1.12–1.26 (m, 0.5 H), 1.29–1.46 (m, 0.5 H), 1.53–1.70 (m, 0.5 H), 1.73 and 1.71 (2 s, 3 H), 1.84–2.09 (m, 2.5 H), 2.12–2.26 (m, 3 H), 2.32–2.52 (m, 3 H), 2.72–2.81 (m, 0.5 H), 2.83–2.89 (m, 0.5 H), 3.38–3.43 (m, 1 H), 3.51–3.57 (m, 1 H), 4.06 and 4.12 (2 q, 2 H), 4.69–4.72 (m, 1 H), 7.13–7.19 (m, 3 H), 7.21–7.28 (m, 2 H).

Step B: Ethyl 2-(RS or SR)-(1-(RS and SR)-3-(SR)-hydroxymethyl-4-(SR)-phenylcyclopent-1-yl)-4-methylpentanoate and ethyl 2-(SR or RS)-(1-(RS and SR)-3-(SR)-hydroxymethyl-4-(SR)-phenylcyclopent-1-yl)-4-methylpentanoate A solution of ethyl 2-(RS and SR)-(1-(RS and SR)-3-(SR)-t-butyldimethylsilyloxymethyl-4-(SR)-phenylcyclopent-1-yl)-4-methylpent-4-enoate from Step A (0.116 g, 0.269 mmol) in ethanol (5 mL) was hydrogenated with 20% palladium hydroxide on carbon (0.030 g) at 45 psi for 5.5 h. The catalyst was filtered off using excess ethanol and 2–3 drops of concentrated hydrogen chloride was added. After 12 h at rt, the volatiles were removed in vacuo to give 0.086 g of residue. The residue was purified by FC (5–20% ethyl acetate in hexanes) to afford separation at the 2-position of the substituted ethyl pentanoate derivative to afford the higher $R_f$ (0.035 g) and lower $R_f$ (0.028 g) racemic title compounds as a mixture of the two cyclopentyl C-1 diastereomers, but stereochemistries were not assigned.

(higher $R_f$): $^1$H NMR (CDCl$_3$): δ 0.89 and 0.87 (2 d, 6 H), 1.13–1.20 (m, 0.5 H), 1.21 (t, 3 H), 1.24–1.30 (m, 0.5 H), 1.43–1.55 (m, 1 H), 1.56–1.69 (m, 2 H), 1.80–1.91 (m, 1.5 H), 1.91–2.04 (m, 0.5 H), 2.11–2.23 (m, 2.5 H), 2.28–2.40 (m, 2.5 H), 2.62–2.71 (m, 0.5 H), 2.78 (dd, 0.5 H), 3.45–3.47 (m, 1 H), 3.59–3.63 (m, 1 H), 4.05–4.13 (m, 2 H), 7.14–7.18 (m, 3 H), 7.21–7.29 (m, 2 H).

(lower $R_f$): $^1$H NMR (CDCl$_3$): δ 0.86 (app t, 6 H), 1.18–1.30 (m, 1 H), 1.26 (t, 3 H), 1.41–1.50 (m, 1 H), 1.55–1.68 (m, 1.5 H), 1.72–1.76 (m, 0.5 H), 1.79–1.87 (m, 0.5 H), 1.93–2.04 (m, 1.5 H), 2.13–2.22 (m, 2.5 H), 2.23–2.37 (m, 2.5 H), 2.68–2.75 (m, 0.5 H), 2.77–2.84 (m, 0.5 H), 3.46–3.50 (m, 1 H), 3.55–3.62 (m, 1 H), 4.10 (q, 2 H), 7.14–7.22 (m, 3 H), 7.24–7.29 (m, 2 H).

Step C: 2-(RS or SR)-(1-(RS and SR)-3-(SR)-((4-(N-(Benzyloxycarbonyl)-N-(allyl)amino)piperidin-1-yl)methyl)-4-(SR)-phenylcyclopent-1-yl)-4-methylpentanoic acid hydrochloride salt Using essentially the same procedures as in Example 1, Steps G—J, the lower isomer from Step B was elaborated to afford 0.0046 g of the racemic title compound as a mixture of the two cyclopentane C-1 diastereomers.

HPLC/MS (ESI): m/z 547 (M+1).

EXAMPLE 4

2-(RS or SR)-(1-(RS or SR)-3-(SR)-((4-(N-(Benzyloxycarbonyl)-N-(allyl)amino)piperidin-1-yl)methyl)-4-(SR)-phenylcyclopent-1-yl)-4-methylpentanoic acid hydrochloride salt and 2-(RS or SR)-(1-(SR or RS)-3-(SR)-((4-(N-(benzyloxycarbonyl)-N-(allyl)amino)piperidin-1-yl)methyl)-4-(SR)-phenylcyclopent-1-yl)-4-methylpentanoic acid hydrochloride salt.

Using reverse phase HPLC (C-18, gradient of water/acetonitrile with 0.5% TFA), the product mixture from Example 3 was separated into the faster eluting (0.0008 g) and slower eluting (0.0021 g) racemic cyclopentyl C-1 diastereomers. The stereochemistries were not assigned.

HPLC/MS (ESI): m/z 547 (M+1) (for each isomer).

EXAMPLE 5

2-(SR or RS)-(1-(RS or SR)-3-(SR)-((4-(N-(Benzyloxycarbonyl)-N-(allyl)amino)piperidin-1-yl)methyl)-4-(SR)-phenylcyclopent-1-yl)-4-methylpentanoic acid hydrochloride salt and 2-(SR or RS)-(1-(SR or RS)-3-(SR)-((4-(N-(benzyloxycarbonyl)-N-(allyl)amino)piperidin-1-yl)methyl)-4-(SR)-phenylcyclopent-1-yl)-4-methylpentanoic acid hydrochloride salt Using essentially the same procedure as in Example 3, Step C, the higher isomer from Example 3, Step B was elaborated to afford the crude title compounds as a mixture of two cyclopentyl C-1 diastereomers. In this case, Prep TLC, eluting with 93:5:1:1 methylene chloridetmethanol/ammonium hydroxide/water, afforded separation of the two cyclopentyl C-1 racemic diastereomers giving the higher $R_f$ (0.0048 g) and lower $R_f$ (0.0019 g) title compounds. Stereochemistries were not assigned.

HPLC/MS (ESI): m/z 547 (M+1) (for each isomer).

EXAMPLE 6

2-(RS or SR)-(1-(RS and SR)-3-(SR)-((4-(N-(4-Nitrobenzyloxycarbonyl)-N-(allyl)amino)piperidin-1-yl)methyl)-4-(SR)-phenylcyclopent-1-yl) cyclohexylacetic acid hydrochloride salt Step A: (1-(RS and SR)-3-(SR)-t-Butyldimethylsilyloxymethyl-4-(SR)-phenylcyclopent-1-yl)acetic acid To a solution of ethyl (1-(RS and SR)-3-(SR)-t-butyldimethylsilyloxymethyl-4-(SR)-phenylcyclopent-1-yl) acetate from Example 2, Step A (2.66 g, 7.06 mmol) in MeOH (70 mL) was added 2.0N sodium hydroxide solution (18 mL, 36 mmol). The reaction mixture was heated at 60° C. for 2 h, allowed to cool to rt, acidified with 18% citric acid until the pH=4, diluted with methylene chloride, poured into water, and extracted three times with methylene chloride. The organic layers were combined, washed with brine, dried over sodium sulfate, filtered and concentrated. The residue was purified by FC (30% ethyl acetate in hexanes with 0.5% AcOH) to afford the title compound (2.15 g).

$^1$H NMR (CDCl$_3$): δ 0.00 (s, 6 H). 0.89 (s, 9 H), 1.21–1.33 (m, 0.5 H), 1.43–1.52 (m, 0.5 H), 1.55–1.68 (m, 0.5 H), 1.75–1.88 (m, 0.5 H), 1.91–2.31 (m, 3 H), 2.38–2.50 (m, 2.5 H), 2.55–2.68 (m, 0.5), 2.78–2.89 (m, 0.5 H), 2.90–2.99 (dd, 0.5 H), 3.45 (dd, 1 H), 3.52–3.60 (m, 1 H), 7.13–7.32 (m, 5 H).

Step B: 4-Methoxybenzyl (1-(RS and SR)-3-(SR)-t-butyldimethylsilyloxymethyl-4-(SR)-phenylcyclopent-1-yl) acetate To a solution of (1-(RS and SR)-3-(SR)-t-butyldimethylsilyloxymethyl-4-(SR)-phenylcyclopent-1-yl) acetic acid from Step A (4.5 g, 13 mmol) in DMF (120 mL) was added triethylamine (2.3 mL, 1.7 g, 17 mmol) and 4-methoxybenzyl chloride (2.1 mL, 2.4 g, 15 mmol). The reaction mixture was stirred at rt for 12 h. TLC analysis showed only 10% conversion to the desired product. Additional triethylamine (4.6 mL, 3.4 g, 34 mmol) and 4-methoxybenzyl chloride (4.2 mL, 4.8 g, 30 mmol) were added. The reaction mixture was stirred at rt for an additional 48 hours until TLC analysis indicated the reaction was complete. The reaction mixture was then diluted with diethyl ether, poured into saturated sodium bicarbonate, extracted three times with diethyl ether. The organic layers were combined, washed with brine, dried over sodium sulfate, filtered, and concentrated. The residue was purified by FC (3% ethyl acetate in hexane) to afford the title product (3.6 g).

$^1$H NMR (CDCl$_3$): δ −0.01 and 0.00 (2 s, 6 H), 0.88 (s, 9 H), 1.23–1.33 (m, 1 H), 1.42–1.49 (m, 0.5 H), 1.58–1.65 (m, 0.5 H), 1.77–1.83 (m, 0.5 H), 1.91–1.96 (m, 0.5 H), 2.03 (dt, 0.5 H), 2.10–2.27 (m, 1.5 H), 2.40–2.49 (m, 2.5 H), 2.58–2.66 (m, 0.5 H), 2.81–2.87 (m, 0.5 H), 2.91 (dd, 0.5 H), 3.44 (dd, 1 H), 3.54–3.58 (m, 1 H), 3.83 (s, 3 H), 5.08 (s, 2 H), 6.90 (d, 2 H), 7.17–7.28 (m, 3 H), 7.28–7.33 (m, 4 H).

Step C: 4-Methoxybenzyl 2-(RS and SR)-(1-(RS and SR)-3-(SR)-t-butyldimethylsilyloxymethyl-4-(SR)-phenylcyclopent-1-yl)cyclohex-2-en-1-ylacetate To THF (5 mL) at −78° C. was added 1.5M lithium diisopropylamide mono(tetrahydrofuran) solution in cyclohexane (0.423 mL, 0.64 mmol). To this solution was then added a solution of 4-methoxybenzyl (1-(RS and SR)-3-

(SR)-t-butyldimethylsilyloxymethyl-4-(SR)-phenylcyclopent-1-yl)acetate from Step B (0.229 g, 0.49 mmol) in THF (1.5 mL) and the reaction mixture was stirred at −78° C. for 1 h. To this solution was then added 3-bromocyclohexene (0.180 mL, 0.252 g, 1.6 mmol). The reaction mixture was stirred for 12 h as it was allowed to warm to rt and then diluted with diethyl ether, poured into saturated sodium bicarbonate and extracted three times with diethyl ether. The organic layers were combined, washed with brine, dried over sodium sulfate, filtered and concentrated. The residue was purified by FC (1–3% ethyl acetate in hexanes) to afford the title product (0.123 g) as an oil.

$^1$H NMR (CDCl$_3$): δ −0.07, −0.06, −0.05, −0.04 and −0.03 (5 s, 6 H), 0.82 and 0.84 (2 s, 9 H), 1.14–1.27 (m, 0.5 H), 1.28–1.42 (m, 1 H), 1.43–1.55 (m, 1 H), 1.66–1.83 (m, 3 H), 1.83–1.88 (m, 1 H), 1.90–2.03 (m, 3 H), 2.05–2.18 (m, 2 H), 2.28–2.38 (m, 0.5 H), 2.39–2.54 (m, 1.5 H), 2.55–2.70 (m, 0.5 H), 2.72–2.85 (m, 1 H), 3.33–3.42 (m, 1 H), 3.46–3.58 (m, 1 H), 3.77 and 3.79 (2 s, 3 H), 4.95–5.13 (m, 2 H), 5.58–5.72 (m, 2 H), 6.82–6.90 (m, 2 H), 7.10–7.18 (m, 3 H), 7.22–7.33 (m, 4 H).

Step D: 4-Methoxybenzyl 2-(RS and SR)-(1-(RS and SR)-3-(SR)-t-butyldimethylsilyloxymethyl-4-(SR)-phenylcyclopent-1-yl) cyclohexylacetate A solution of 4-methoxybenzyl 2-(RS and SR)-(1-(RS and SR)-3-(SR)-t-butyldimethylsilyloxymethyl-4-(SR)-phenylcyclopent-1-yl)cyclohex-2-en-1-ylacetate from Step C (0.130 g, 0.24 mmol) in methanol (3 mL) was hydrogenated with palladium on carbon (0.027 g) at 45 psi for 15 min. The catalyst was filtered off and the volatiles removed in vacuo to give 0.130 g of a residue which was taken on to Step E without purification.

Step E: 4-Methoxybenzyl 2-(RS or SR)-(1-(RS and SR)-3-(SR)-hydroxymethyl-4-(SR)-phenylcyclopent-1-yl) cyclohexylacetate and 4-methoxybenzyl 2-(SR or RS)-(1-(RS and SR)-3-(SR)-hydroxymethyl-4-(SR)-phenylcyclopent-1-yl)cyclohexylacetate To a solution of 4-methoxybenzyl 2-(RS and SR)-(1-(RS and SR)-3-(SR)-t-butyldimethylsilyloxymethyl-4-(SR)-phenylcyclopent-1-yl) cyclohexylacetate (0.130 g, 0.24 mmol) in THF (3 mL) was added a 1.0 M solution of tetrabutylammonium fluoride in THF (0.354 mnL, 0.354 mmol) and the reaction mixture was stirred at rt for 12 h. The reaction mixture was diluted with ethyl acetate, poured into 5% aqueous HCl solution, extracted three times with ethyl acetate, combined organic layers, washed with brine, dried over sodium sulfate and concentrated to afford 0.088 g. The residue was purified by FC (3% ethyl acetate in methylene chloride) to afford separation at the 2-position of the cyclohexylacetate to give the higher R$_f$ (0.030 g) and lower R$_f$ (0.031 g) racemic title compounds as a mixture of the two possible cyclopentyl C-1 diastereomers, but stereochemistries were not assigned.

(higher R$_f$): $^1$H NMR (CDCl$_3$): δ 0.93–1.28 (m, 4 H), 1.47 (br s, 3 H), 1.52–1.75 (m, 5.5 H), 1.78–1.94 (m, 1.5 H), 1.96–2.02 (m, 0.5 H), 2.08–2.19 (m, 1.5 H), 2.22–2.28 (m, 1 H), 2.35–2.43 (m, 0.5 H), 2.56–2.71 (m, 1.5 H), 3.39–3.45 (m, 1 H), 3.54–3.60 (m, 1 H), 3.76 and 3.77 (2 s, 3 H), 5.01 and 5.02 (2 s, 2 H), 6.85 (d, 2 H), 7.12–7.19 (m, 3 H), 7.22–7.31 (m, 4 H).

(lower R$_f$): $^1$H NMR (CDCl$_3$): δ 0.93–1.38 (m, 4 H), 1.47 (br s, 3 H), 1.52–1.72 (m, 5 H), 1.74–1.93 (m, 2 H), 1.95–2.03 (m, 0.5 H), 2.09–2.20 (m, 1.5 H), 2.22–2.28 (m, 1 H), 2.35–2.48 (m, 0.5 H), 2.53–2.60 (m, 0.5 H), 2.64–2.73 (m, 1 H), 3.39–3.45 (m, 1 H), 3.52–3.57 (m, 1 H), 3.79 (s, 3 H), 5.05 and 5.06 (2 s, 2 H), 6.87 (d, 2 H), 7.12–7.20 (m, 3 H), 7.23–7.31 (m, 4 H).

Step F: 4-Methoxybenzyl 2-(RS or SR)-(1-(RS and SR)-3-(SR)-formyl-4-(SR)-phenylcyclopent-1-yl) cyclohexylacetate To a solution of oxalyl chloride (0.037 mL, 0.054 g, 0.42 mmol) in methylene chloride (1 mL) at −70° C. was added dropwise DMSO (0.060 mL, 0.066 g, 0.85 mmol). After 10 min, a solution of 4-methoxybenzyl 2-(RS or SR)-(1-(RS and SR)-3-(SR)-hydroxymethyl-4-(SR)-phenylcyclopent-1-yl) cyclohexylacetate, the higher R$_f$ isomer from Step E, (0.030 g, 0.068 mmol) in methylene chloride (0.5 mL) was added dropwise. The reaction was stirred at −70° C. for 40 min and then triethylamine (0.177 mL, 0.128 g, 1.27 mmol) was added. The reaction mixture was allowed to warm to rt for 10 min and then diluted with methylene chloride, poured into water, and extracted three times with methylene chloride. The organic layers were combined, washed with brine, dried over sodium sulfate, filtered and concentrated in vacuo. The crude title compound was used directly in Step G.

Step G: 4-Methoxybenzyl 2-(RS or SR)-(1-(RS and SR)-3-(SR)-((4-(N-(4-nitrobenzyloxycarbonyl)-N-(allyl)amino)piperidin-1-yl)methyl)-4-(SR)-phenylcyclopent-1-yl) cyclohexylacetate To a solution of 4-methoxybenzyl 2-(RS or SR)-(1-(RS and SR)-3-(SR)-formyl-4-(SR)-phenylcyclopent-1-yl) cyclohexylacetate from Step F (0.018 g, 0.041 mmol) in 1,2-dichloroethane (1 mL) was added 4-(N-(4-nitrobenzyloxycarbonyl)-N-(allyl)amino)piperidine hydrochloride (0.022 g, 0.062 mmol) and DIPEA (0.011 mL, 0.008 g, 0.062 mmol). After 10 min, sodium triacetoxyborohydride (0.017 g, 0.082 mmol) was added. The reaction mixture was stirred at rt for 12 h, diluted with methylene chloride, poured into aqueous sodium bicarbonate and extracted three times with methylene chloride. The organic layers were combined, washed with brine, dried over sodium sulfate, filtered and concentrated in vacuo. The residue was purified by prep TLC eluting with 2% MeOH in methylene chloride to afford the title compound as a mixture of epimers at the cyclopentyl C-1 (0.031 g).

HPLC/MS (ESI): m/z 738 (M+1).

Step H: 2-(RS or SR)-(1-(RS and SR)-3-(SR)-((4-(N-(4-Nitrobenzyloxycarbonyl)-N-(allyl)amino)piperidin-1-yl) methyl)-4-(SR)-phenylcyclopent-1-yl)cyclohexylacetic acid A solution of 4-methoxybenzyl 2-(RS or SR)-(1-(RS and SR)-3-(SR)-((4-(N-(4-Nitrobenzyloxycarbonyl)-N-(allyl) amino)piperidin-1-yl)methyl)-4-(SR)-phenylcyclopent-1-yl)cyclohexylacetate from Step G (0.031 g, 0.042 mmol) was dissolved in 96% formic acid (1 mL) and stirred at rt for 12 h. The reaction mixture was neutralized using 2N NaOH, diluted with methylene chloride and extracted three times with methylene chloride. The organic layers were combined, washed with brine, dried over sodium sulfate and concentrated. The residue was purified by prep TLC eluting with 84:14:1:1 methylene chloride/methanol/ammonium hydroxide/water to afford the title compound (0.016 g).

Step I 2-(RS or SR)-(1-(RS and SR)-3-(SR)-((4-(N-(4-Nitrobenzyloxycarbonyl)-N-(allyl)amino)piperidin-1-yl) methyl)-4-(SR)-phenylcyclopent-1-yl)cyclohexylacetic acid hydrochloride salt 2-(RS or SR)-(1-(RS and SR)-3-(SR)-((4-(N-(4-Nitrobenzyloxycarbonyl)-N-(allyl)amino)piperidin-1-yl) methyl)-4-(SR)-phenylcyclopent-1-yl)cyclohexylacetic acid from Step H (0.016 g, 0.026 mmol) was taken up in 1:1 methylene chloride:ether (0.5 mL) and 1N hydrochloric acid in diethyl ether was added (0.078 mL, 0.078 mmol). The volatiles were removed under a stream of nitrogen to give the title racemic compound as a white solid.

HPLC/MS (ESI): m/z 618 (M+1).

EXAMPLE 7

2-(SR or RS)-(1-(RS and SR)-3-(SR)-((4-(N-(4-Nitrobenzyloxycarbonyl)-N-(allyl)amino)piperidin-1-yl)methyl)-4-((SR)-phenylcyclopent-1-yl) cyclohexylacetic acid hydrochloride salt Using essentially the same procedure as in Example 6, Steps F-I, the lower isomer from Example 6, Step E was elaborated to afford the title compound (0.017 g).

HPLC/MS (ESI): m/z 618 (M+1).

EXAMPLE 8

2-(R or S)-(1-(R and S)-3-(S)-((4-(N-(4-Nitrobenzyloxycarbonyl)-N-(allyl)amino)piperidin-1-yl)methyl)-4-(S)-phenylcyclopent-1-yl) cyclohexylacetic acid hydrochloride salt Step A: (+−)-trans-4-Methylene-2-phenylcyclopentanoic acid To a solution of methyl (+−)-trans-4-methylene-2-phenylcyclopentanoate prepared as in Example 1, Step A (28.4 g, 131 mmol) in methanol (400 mL) was added 5N sodium hydroxide (131 mL, 656 mmol). The reaction was heated at 65° C. for 1 h then cooled and concentrated. The residue was diluted with water, acidified with 2M hydrochloric acid and extracted twice with methylene chloride. The organic layers were each washed with brine, dried over sodium sulfate, combined and concentrated in vacuo to give the crude title acid (27.2 g) which was used directly in Step B.

Step B: (+)-trans-4-Methylene-2-phenylcyclopentanoic acid, (S)-(−)-α-methylbenzylamine salt and (−)-trans-4-methylene-2-phenylcyclopentanoic acid, (R)-(+)-α-methylbenzylamine salt The crude (+−)-trans-4-methylene-2-phenylcyclopentanoic acid from Step A (assumed 131 mmol) was taken up in 2-propanol (400 mL), warmed to 80° C. and treated with (S)-(−)-α-methylbenzylamine (8.45 mL, 66 mmol). The mixture was stirred while allowed to cool to rt over 16 h and was then cooled to −10° C. for 1 h. The salt was filtered, washed with a small amount of ether to remove 2-propanol and air dried to give 6.442 g of salt. This was recrystallized twice from 2-propanol to give the title salt (4.713 g), $[\alpha]_D$=+56 (MeOH, c=0.20).

The combined mother liquors from above were concentrated and the residue was taken up in water, acidified with 2M hydrochloric acid and extracted twice with methylene chloride. The organic layers were each washed with brine, dried over sodium sulfate, combined and concentrated in vacuo. The residue was taken up in 2-propanol (400 mL), warmed to 80° C. and treated with (R)-(+)-α-methylbenzylamine (9.1 mL, 70 mmol). The mixture was stirred while allowed to cool to rt over 16 h and was then cooled to −10° C. for 1 h. The salt was filtered, washed with a small amount of ether to remove 2-propanol and air dried to give 8.22 g of salt. This was recrystallized from 2-propanol to give the title salt (6.31 g), $[\alpha]_D$=−55 (MeOH, c=0.21).

Step C: (+)-trans-4-Methylene-2-phenylcyclopentanoic acid and (−)-trans-4-methylene-2-phenylcyclopentanoic acid Method A:

The (+) -trans-4-methylene-2-phenylcyclopentanoic acid, (S)-(−)-α-methylbenzylamine salt from Step B (4.7 g) was suspended in methylene chloride and water and acidified with 2M hydrochloric acid and extracted twice with methylene chloride. The organic layers were each washed with brine, dried over sodium sulfate, combined and concentrated in vacuo to give the title (+) acid (3.1 g), $[\alpha]_D$=+101 (MeOH, c=0.135).

Similarly, the (−)-trans-4-methylene-2-phenylcyclopentanoic acid, (R)-(+)-α-methylbenzylamine salt (6.3 g) was converted to the free (−)-title acid (4.23 g), $[\alpha]_D$=−103 (MeOH, c=0.23).

Method B:

Step B1: 1-(S)-(((S)-(−)-4-Benzyl-2-oxazolidin-1-yl)carbonyl)-3-methylene-2-(S)-phenylcyclopentane (higher $R_f$) and 1-(R)-(((S)-(−)-4-benzyl-2-oxazolidin-1-yl)carbonyl)-3-methylene-2-(R)-phenylcyclopentane (lower $R_f$)

A solution of (+−)-trans-4-methylene-2-phenylcyclopentanoic acid (47.5 g, 235 mmol) in ether (1 L) and TEA (36 mL, 260 mmol) was cooled to −10° C. Trimethylacetyl chloride (31.8 mL, 260 mmol) was then added slowly and after stirring at −10° C. for 10 min, the reaction was allowed to warm to 10° C. over 1 h. The reaction was then recooled to −60° C.

To the above solution at −60° C. was added via a canula a solution of (S)-(−)-4-benzyl-2-oxazolidinone (45.8 g, 260 mmol) in THF (500 mL) which had been treated at −50° C. with 2.5 M n-butyl lithium (103 mL, 257 mmol) and aged at −50° C. for 45 min. The reaction was allowed to warm to rt over 16 h. The reaction was diluted with ether (1 L) and quenched with sat'd aqueous ammonium chloride (1 L). The layers were separated and the aqueous layer was reextracted with a second portion of ether. The organic layers were each washed twice with 2N hydrochloric acid, twice with iN sodium hydroxide and brine, dried over sodium sulfate, combined and concentrated. The residue was purified by chromatography (20% ethyl acetate in hexanes) to give the two diastereomeric products, higher $R_f$ (18.4 g) and lower $R_f$ (17.7 g).

Step B2: (+)-trans-4-Methylene-2-phenylcyclopentanoic acid

A solution of 1-(S)-(((S)-(−)-4-benzyl-2-oxazolidin-1-yl)carbonyl)-3-methylene-2-(S)-phenylcyclopentane (higher $R_f$ product from Step B1) (20.9 g, 58 mmol) in a 3:1 mixture of THF:water (1 L) was cooled to 5° C. Hydrogen peroxide (30%, 39.5 mL, 350 mmol) and lithium hydroxide (4.85 g, 106 mmol) were added and the reaction was stirred for 3.5 h. The excess peroxide was quenched by dropwise addition of sodium sulfite (60 g) in water (1 L) over 1.5 h while maintaining the temperature below 5° C. After stirring for 2 additional hours, most of the THF was removed in vacuo and the aqueous layer was washed 3 times with methylene chloride. The aqueous layer was acidified to pH=2 with conc. HCl and reextracted twice with methylene chloride. The organic layers were washed with brine, dried and concentrated to give the (+) title product, $[\alpha]_D$=+100.5 (MeOH, c=0.207).

Step D: (+)-trans-1-Hydroxymethyl-4-methylene-2-phenylcyclopentane and (−)-trans-1-hydroxymethyl-4-methylene-2-phenylcyclopentane Method A:

A solution of (+)-trans-4-methylene-2-phenylcyclopentanoic acid from Step C (4.15 g, 20.5 mmol) in THF (100 mL) under nitrogen was cooled to −7° C. and 1M LAH in THF (31 mL, 31 mmol) was added dropwise over 15. The reaction was allowed to warm to rt over 16 h. The excess LAH was quenched by dropwise addition of acetone and the reaction was then poured into dilute aq. HCl. The mixture was extracted twice with ether and the organic layers were washed with brine, dried over sodium sulfate, combined and concentrated. The residue was purified by FC (20% ethyl acetate in hexanes) to afford the title (+) product (3.93 g), $[\alpha]_D$=+50 (MeOH, c=0.20).

Similarly, the (−)-trans-4-methylene-2-phenylcyclopentanoic acid from Step C (4.23 g) was converted to the title (−) alcohol (3.75 g), $[\alpha]_D$=−51 (MeOH, c=0.2).

Method B:

Prep-HPLC of (+−)-trans-4-methylene-2-phenylcyclopentanoic from Example 1, Step B using a Chiracel OD column (5–10% isopropanol in hexanes) affords good separation of the title (−) enantiomer as the first eluting band and the (+) enantiomer as the second eluting band.

Step E: (+)-trans-1-t-Butyldimethylsilyloxymethyl-4-methylene-2-phenylcyclopentane and (−)-trans-1-t-butyldimethylsilyloxymethyl-4-methylene-2-phenylcyclopentane To a solution of (+)-trans-1-hydroxymethyl-4-methylene-2-phenylcyclopentane from Step D (3.9 g, 21 mmol) in methylene chloride (50 mL) was added t-butyldimethylsilyl chloride (4.7 g, 31 mmol) and DIPEA (7.3 mL, 42 mmol). The reaction was stirred at rt for 16 h, poured into dilute aq. HCl and extracted twice with ether. The organic layers were washed with brine, dried over sodium sulfate, combined and concentrated. The residue was purified by FC (100% hexanes) to afford the title product (5.6 g) as a oil, $[\alpha]_D$=+42.3 (MeOH, c=0.18).

Similarly, (−)-trans-1-hydroxymethyl-4-methylene-2-phenylcyclopentane from Step D (3.75 g) was converted to the title (−) silylether (5.5 g), $[\alpha]_D$=−44.4 (MeOH, c=0.18).

Step F: (+)-trans-3-Hydroxymethyl-4-phenylcyclopentan-1-one and (−)-trans-3-hydroxymethyl-4-phenylcyclopentan-1-one Method A:

A solution of (+)-trans-1-t-butyldimethylsilyloxymethyl-4-methylene-2-phenylcyclopentane from Step E (4.6 g, 15 mmol) in methanol (100 mL) was cooled to −70° C. in a dry-ice acetone bath and ozone was bubbled through until a blue color persisted which was discharged with a stream of nitrogen. Dimethylsulfide (10 mL) was added and after 15 min, the reaction was allowed to warm to rt over 16 h. Since by TLC (20% ethyl acetate in hexanes) indicated that there was significant loss of the silyl as well as dimethylketal formation, the methanol was mostly remove in vacuo. The residue was diluted with water and treated with sulfuric acid (6 mL) and stirred for 2 h. The mixture was extracted twice with ethyl acetate and the organic layers were washed with brine (containing some sodium bicarbonate), dried over sodium sulfate, combined and concentrated. The residue was purified by FC (15–30% ethyl acetate in hexanes) to give the (+) title ketone/alcohol (2.87 g), $[\alpha]_D$=−96 (MeOH, c=0.2).

Similarly, (−)-trans-1-t-butyldimethylsilyloxymethyl-4-methylene-2-phenylcyclopentane from Step E (4.4 g) was converted to the title (−) ketone/alcohol (2.8 g), $[\alpha]_D$=+97 (MeOH, c=0.2).

Method B:

The title compounds can also be obtained directly from (+)-trans-1-hydroxymethyl-4-methylene-2-phenylcyclopentane and (−)-trans-1-hydroxymethyl-4-methylene-2-phenylcyclopentane by ozonolysis as above. Thus, (+)-trans-1-hydroxymethyl-4-methylene-2-phenylcyclopentane (3.7 g, 20 mmol) afforded (+)-trans-1-hydroxymethyl-4-oxo-2-phenylcyclopentane (3.5 g).

Step G: (+)-trans-1-t-Butyldimethylsilyloxymethyl-4-oxo-2-phenylcyclopentane and (−)-trans-1-t-butyldimethylsilyloxymethyl-4-oxo-2-phenylcyclopentane To a solution of (+)-trans-3-hydroxymethyl-4-phenylcyclopentan-1-one from Example 8, Step F (3.3 g, 16 mmol) in methylene chloride (100 mL) was added t-butyldimethylsilyl chloride (11 g, 49 mmol) and DIPEA (22 mL, 74 mmol). The reaction was stirred at rt for 16 h, poured into dilute aq. hydrochloric acid and extracted twice with ether. The organic layers were washed with brine, dried over sodium sulfate, a combined and concentrated. The residue was purified by FC (5% ethyl acetate in hexanes) to afford of (+)-trans-1-t-butyldimethylsilyloxymethyl-4-oxo-2-phenylcyclopentane (6.3 g) as a oil.

Similarly, (−)-trans-1-hydroxymethyl-4-methylene-2-phenylcyclopentane from Step F can be converted to the title (−) ketone/silyl ether.

Step H: Ethyl (1-(R and S)-3-(S)-t-butyldimethylsilyloxymethyl)-4-(S)-phenylcyclopent-1-yl) acetate and ethyl (1-(R and S)-3-(R)-t-butyldimethylsilyloxymethyl)-4-(R)-phenylcyclopent-1-yl) acetate Using essentially the same procedures as in Example 1, Steps E and F and Example 2, Step A, but substituting (+)-trans-1-t-butyldimethylsilyloxymethyl-4-oxo-2-phenylcyclopentane from Step G, the chiral 3-(S),4-(S) title compound can be prepared.

Similarly, (−)-trans-1-t-butoxydimethylsilyloxymethyl-4-oxo-2-phenylcyclopentane from Step G can be converted to the chiral 3-(R),4-(R) title acetate.

Step I: 2-(R or S)-(1-(R and S)-3-(S)-((4-(N-(4-Nitrobenzyloxycarbonyl)-N-(allyl)amino)piperidin-1-yl) methyl)-4-(S)-phenylcyclopent-1-yl)cyclohexylacetic acid hydrochloride salt Using essentially the same procedures as in Example 6, Steps A to I, but substituting ethyl (1-(R and S)-3-(S)-t-butyldimethylsilyloxymethyl)-4-(S)-phenylcyclopent-1-yl) acetate from Step H and using the higher $R_f$ epimer at the 2-position of the cyclohexylacetate as in Example 6, Step F, the chiral title compounds can also be prepared as a mixture of the two cyclopentyl C-1 epimers.

EXAMPLE 9

2-(S or R)-(1-(R and S)-3-(S)-((4-(N-(4-Nitrobenzyloxycarbonyl)-N-(allyl)amino)piperidin-1-yl)methyl)4-(S)-phenylcyclopent-1-yl) cyclohexylacetic acid hydrochloride salt Using essentially the same procedures as in Example 6, Steps A to I, but substituting ethyl (1-(R and S)-3-(S)-t-butyldimethylsilyloxymethyl)-4-(S)-phenylcyclopent-1-yl) acetate from Example 8, Step H and using the lower $R_f$ epimer at the 2-position of the cyclohexylacetate as in Example 7, the chiral title compounds can also be prepared as a mixture of the two cyclopentyl C-1 epimers.

EXAMPLE 10

2-(R or S)-(1-(R and S)-3-(R)-((4-(N-(4-Nitrobenzyloxycarbonyl)-N-(allyl)amino)piperidin-1-yl)methyl)-4-(R)-phenylcyclopent-1-yl) cyclohexylacetic acid hydrochloride salt Using essentially the same procedures as in Example 6, Steps A to I, but substituting ethyl (1-(R and S)-3-(R)-t-butyldimethylsilyloxymethyl)-4-(R)-phenylcyclopent-1-yl) acetate from Step H and using the higher $R_f$ epimer at the 2-position of the cyclohexylacetate as in Example 6, Step F, the chiral title compounds can also be prepared as a mixture of the two cyclopentyl C-1 epimers.

EXAMPLE 11

2-(S or R)-(1-(R and S)-3-(R)-((4-(N-(4-Nitrobenzyloxycarbonyl)-N-(allyl)amino)piperidin-1-yl)methyl)-4-(R)-phenylcyclopent-1-yl) cyclohexylacetic acid hydrochloride salt Using essentially the same procedures as in Example 6, Steps A to I, but substituting ethyl (1-(R and S)-3-(R)-t-butyldimethylsilyloxymethyl)-4-(R)-phenylcyclopent-1-yl) acetate from Example 8, Step H and using the lower $R_f$ epimer at the 2-position of the cyclohexylacetate as in Example 7, the chiral title compounds can also be prepared as a mixture of the two cyclopentyl C-1 epimers.

EXAMPLE 12

2-(R or S)-(1-(R or S)-3-(S)-((4-(N-(4-Nitrobenzyloxycarbonyl)-N-(allyl)amino)piperidin-1-yl)methyl)-4-(S)-phenylcyclopent-1-yl)-3-(cyclopropyl)propanoic acid hydrochloride salt and 2-(R or S)-(1-(S or R)-3-(S)-((4N-(4-nitrobenzyloxycarbonyl)-N-(allyl)amino)piperidin-1-yl)methyl)-4-(S)-phenylcyclopent-1-yl)-3-(cyclopropyl)propanoic acid hydrochloride salt Step A:

EXAMPLE 13

2-(S or R)-(1-(R or S)-3-(S)-((4-(N-(4-Nitrobenzyloxycarbonyl)-N-(allyl)amino)piperidin-1-yl)methyl)-4-(S)-phenylcyclopent-1-yl)-3-(cyclopropyl)propanoic acid hydrochloride salt and 2-(S or R)-(1-(S or R)-3-(S)-((4-(N-(4-nitrobenzyloxycarbonyl)-N-(allyl)amino)piperidin-1-yl)methyl)-4-(S)-phenylcyclopent-1-yl)-3-(cyclopropyl)propanoic acid hydrochloride salt Using essentially the same procedures as in Example 12, but substituting the lower $R_f$ epimer at the 2-position of the propanoate from Step B, the chiral title compounds can also be prepared as individual cyclopentyl C-1 epimers.

EXAMPLE 14

2-(R or S)-(1-(R or S)-3-(S)-((4-(N-(4-Nitrobenzyloxycarbonyl)-N-(allyl)amino)piperidin-1-yl)methyl)-4-(S)-phenylcyclopent-1-yl)-3-(cyclobutyl)propanoic acid hydrochloride salt and 2-(R or S)-(1-(S or R)-3-(S)-((4-(N-(4-nitrobenzyloxycarbonyl)-N-(allyl)amino)piperidin-1-yl)methyl)-4-(S)-phenylcyclopent-1-yl)-3-(cyclobutyl)propanoic acid hydrochloride salt Using essentially the same procedures as in Example 12, but substituting cyclobutylmethyl bromide in Step A, the chiral title compounds can be prepared as the individual cyclopentyl C-1 epimers.

EXAMPLE 15

2-(S or R)-(1-(R or S)-3-(S)-((4-(N-(4-Nitrobenzyloxycarbonyl)-N-(allyl)amino)piperidin-1-yl)methyl)-4-(S)-phenylcyclopent-1-yl)-3-(cyclobutyl)propanoic acid hydrochloride salt and 2-(S or R)-(1-(S or R)-3-(S)-((4-(N-(4-nitrobenzyloxycarbonyl)-N-(allyl)amino)piperidin-1-yl)methyl)-4-(S)-phenylcyclopent-1-yl)-3-(cyclobutyl)propanoic acid hydrochloride salt Using essentially the same procedures as in Example 12 and 14, but substituting the lower $R_f$ epimer at the 2-position of the propanoate from Step B, the chiral title compounds can also be prepared as individual cyclopentyl C-1 epimers.

EXAMPLE 16

2-(R or S)-(1-(R or S)-3-(S)-((4-(N-(4-Nitrobenzyloxycarbonyl)-N-(allyl)amino)piperidin-1-yl)methyl)-4-(S)-(3-fluorophenyl)cyclopent-1-yl)-3-(cyclopropyl)propanoic acid hydrochloride salt and 2-(R or S)-(1-(S or R)-3-(S)-((4-(N-(4-nitrobenzyloxycarbonyl)-N-(allyl)amino)piperidin-1-yl)methyl)-4-(S)-(3-fluorophenyl)cyclopent-1-yl)-3-(cyclopropyl)propanoic acid hydrochloride salt Step A: Methyl (+−)-trans-4-methylene-2-(3-fluorophenyl) cyclopentanoate A mixture of methyl trans-3-fluorocinnamate (41.25 g, 229 mmol), tetrakis(triphenylphosphine) palladium(0) (18.5 g, 16 mmol), 1,2-bis(diphenylphosphino)ethane (5.5 g, 13.7 mmol) and 2-((trimethylsilyl)methyl)-2-propen-1-yl acetate (42.66 g, 229 mmol) in THF (300 mL) under nitrogen was heated to reflux for 6 h and then stirred at rt for 16 h. The reaction was diluted with hexane and filtered to remove yellow precipitate. The volatiles were then removed in vacuo and the residue was purified by FC (3 to 5% ethyl acetate in hexanes) to afford the title compound (45 g).

$^1$H NMR (CDCl$_3$) δ: 2.52 (m, 1 H), 2.68 (m, 1 H), 2.8–2.9 (m, 2 H), 2.95 (ddd, 1 H), 3.45 (ddd, 1 H), 3.63 (s, 3 H), 4.96 (m, 2 H), 6.9–7.0 (m, 2 H), 7.03 (d, 1 H), 7.2–7.3 (m, 1 H).

Step B: (+−)-trans-4-Methylene-2-(3-fluorophenyl) cyclopentanoic acid

To a solution of methyl (+−)-trans-4-methylene-2-(3-fluoro)phenylcyclopentanoate prepared as in Example 33, Step A (47 g, 200 mmol) in methanol (500 mL) was added 5N sodium hydroxide (200 mL, 1000 mmol). The reaction was stirred at rt for 60 h then concentrated in vacuo. The residue was taken up in water, acidified with 2M hydrochloric acid and extracted twice with methylene chloride. The organic layers were each washed with brine, dried over sodium sulfate, combined and concentrated in vacuo to give the crude title acid (40.8 g) which was used directly in Step C.

Step C: (+)-trans-1-Hydroxymethyl-4-methylene-2-(3-fluorophenyl)cyclopentane and (−)-trans-1-hydroxymethyl-4-methylene-2-(3-fluorophenyl)cyclopentane A solution of (+−)-trans-4-methylene-2-(3-fluorophenyl) cyclopentanoate (5.2 g, 23.6 mmol) from Step B in THF (100 mL) was cooled to 0° C. under nitrogen and 1M lithium aluminum hydride (LAH) in THF (35.4 mL) was added dropwise over 10 min. The reaction was stirred at rt for 16 h, the excess LAH was quenched by dropwise addition of acetone and the reaction was then poured into dilute aq. hydrochloric acid. The mixture was extracted twice with ether and the organic layers were washed with brine, dried over sodium sulfate, combined and concentrated. The residue was purified by FC (25% ethyl acetate in hexanes) to afford the racemic title product (4.1 g) as a an oil. Chiral Prep HPLC on a 2 cm×25 cm Chiracel OD column eluting with 5% isopropanol in hexanes (25 injections) afforded the (−)-enantiomer, [α]$_D$=−45.5 (MeOH, c=0.9), as the first eluting peak (R$_t$=17.5 mn) and the (+)-enantiomer (1.87 g), [α]$_D$=+45.0 (MeOH, c=1.0), as the second peak (R$_t$=22.0 min).

$^1$H NMR (CDCl$_3$) δ: 2.2–2.35 (m, 2 H), 2.5 (m, 1 H), 2.65–2.85(m, 2 H), 2.9 (m, 1 H), 3.51 and 3.68 (dABq, 2 H), 4.93 (m, 2 H), 6.9–7.0 (m, 2 H), 7.06 (d, 1 H), 7.3–7.4 (m, 1 H).

Step D: (+)-trans-3-Hydroxymethyl-4-(3-fluorophenyl) cyclopentan-1-one

A solution of (+)-trans-1-hydroxymethyl-4-methylene-2-(3-fluorophenyl)cyclopentane from Step C (1.87 g, 9.0 mmol) in methanol (75 mL) was cooled in a dry ice/acetone bath and ozone was bubbled into the solution until the blue color persisted. The excess ozone was removed with a stream of nitrogen and then dimethylsulfide (5 mL) was added. After 10 min, the bath was removed and the reaction was allowed to warm to rt over 2 h. The mixture was treated with 10 drops of sulfuric acid (c) in water (2 mL) for 1 h before most of the methanol was removed in vacuo. The mixture was diluted with water and extracted twice with ethyl acetate and the organic layers were washed with brine, dried over sodium sulfate, combined and concentrated. The residue was purified by FC (50% ethyl acetate in hexanes) to give the title compound (1.87 g)), $[\alpha]_D=+132$ (MeOH, c=1.2).

$^1$H NMR (CDCl$_3$) δ: 2.3–2.45 (m, 2 H), 2.5 (m, 1 H), 2.61 and 2.77 (dABq, 2 H), 2.28 (ddd, 1 H), 3.61 and 3.75 (dABq, 2 H), 6.9–7.0 (m, 2 H), 7.06 (d, 1 H), 7.3–7.4 (m, 1 H).

Step E: 4-Methoxybenzyl (1-(R and S)-3-(S)-t-butyldimethylsilyloxymethyl-4-(S)-(3-fluorophenyl)cyclopent-1-yl)acetate Using essentially the same procedures as in Example 1, Steps C to F, Example 2, Step A, and Example 6 Steps A and B, but substituting non-racemic (+)-trans-3-hydroxymethyl-4-(3-fluorophenyl)cyclopentan-1-one from Step D, the title compound can be prepared.

Step F: 2-(R or S)-(1-(R or S)-3-(S)-((4-(N-(4-Nitrobenzyloxycarbonyl)-N-(allyl)amino)piperidin-1-yl)methyl)-4-(S)-(3-fluorophenyl)cyclopent-1-yl)-3-(cyclopropyl)propanoic acid hydrochloride salt and 2-(R or S)-(1-(S or R)-3-(S)-((4-(N-(4-nitrobenzyloxycarbonyl)-N-(allyl)amino)piperidin-1-yl)methyl)-4-(S)-(3-fluorophenyl)cyclopent-1-yl)-3-(cyclopropyl)propanoic acid hydrochloride salt Using essentially the same procedures as in Example 12, but substituting non-racemic 4-methoxybenzyl (1-(R and S)-3-(S)-t-butyldimethylsilyloxymethyl-4-(S)-(3-fluorophenyl)cyclopent-1-yl)acetate from Step E and using the higher R$_f$ epimer at the 2-position of the propanoate, the title compounds can be prepared as individual epimers at the cyclopentyl C-1.

EXAMPLE 17

2-(S or R)-(1-(R or S)-3-(S)-((4-(N-(4-Nitrobenzyloxycarbonyl)-N-(allyl)amino)piperidin-1-yl)methyl)-4-(S)-(3-fluorophenyl)cyclopent-1-yl)-3-(cyclopropyl)propanoic acid hydrochloride salt and 2-(S or R)-(1-(S or R)-3-(S)-((4-(N-(4-nitrobenzyloxycarbonyl)-N-(allyl)amiino)piperidin-1-yl)methyl)-4-(S)-(3-fluorophenyl)cyclopent-1-yl)-3-(cyclopropyl)propanoic acid hydrochloride salt Using essentially the same procedures as in Example 16, but using the lower R$_f$ epimer at the 2-position of the propanoate, the title compounds can be prepared as individual epimers at the cyclopentyl C-1.

EXAMPLE 18

Using essentially the same procedures as in Examples 12 and 13, but using a different piperidine (prepared as described below in Procedures 1–10), a wide variety of different 2-(R or S)-(1-(R or S)-3-(S)-(4-aminosubstituted)piperidin-1-yl)methyl)-4-(S)-phenylcyclopent-1-yl)-3-(cyclopropyl)propanoic acid hydrochloride salts can be prepared.

EXAMPLE 19

Using essentially the same procedures as in Examples 16 and 17, but using a different piperidine (prepared as described below in Procedures 1–10), a wide variety of different 2-(R or S)-(1-(R or S)-3-(S)-(4-aminosubstituted)piperidin-1-yl)methyl)-4-(S)-(3-fluorophenyl)cyclopent-1-yl)-3-(cyclopropyl)propanoic acid hydrochloride salts can be prepared.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of the formula I:

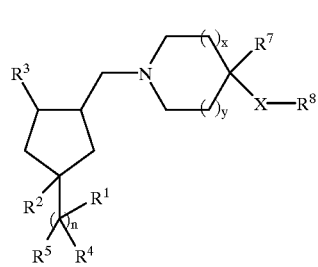

wherein:
X is —Y—, —(C$_{1-2}$ $_{1\ alkyl}$)—Y—(C$_{1-6}$ alkyl)—, —(C$_{1-6}$ alkyl)—, —(C$_{1-2}$)—Y—, or —Y—(C$_{1-6}$ alkyl)—,
  where the alkyl is unsubstituted or substituted with 1–7 substituents where the substituents are independently selected from:
  (a) halo,
  (b) hydroxy,
  (c) —O—C$_{1-3}$ alkyl, and
  (d) trifluoromethyl,
  where Y is selected from: —(CO)—, —(CO)O—, —O(CO)—, —(CO)NR$^9$—, —NR$^9$(CO)—, —O(CO)NR$^9$—, —NR$^9$(CO)O—, and —NR$^9$(CO)NR$^{10}$—,
  where R$^9$ is independently selected from: hydrogen, C$_{1-10}$ alkyl, C$_{3-6}$ cycloalkyl, C$_{1-6}$ alkyl-C$_{3-6}$ cycloalkyl, C$_{2-10}$ alkenyl, C$_{2-10}$ alkynyl, benzyl or phenyl, which is unsubstituted or substituted with 1–3 substituents where the substituents are independently selected from: halo, C$_{1-3}$ alkyl, C$_{1-3}$ alkoxy and trifluoromethyl,
  and where R$^{10}$ is independently selected from: hydrogen, C$_{1-6}$ alkyl, benzyl, or phenyl, which is unstibstituted or substituted with 1–3 substituents where the substituents are independently selected from: halo, $C_{1-3}$ alkyl, $C_{1-3}$ alkoxy and trifluoromethyl, or where $R^9$ and $R^{10}$ are joined together to form a 5–8 membered ring consisting of the —N(CO)N— functional group and a balance of carbon atoms, wherein the ring is be unsubstituted or substituted with halo, $C_{1-3}$ alkyl, and $C_{1-3}$ alkoxy;

$R^1$ is selected from:
(1) —CO$_2$H,
(2) —NO$_2$,
(3) —tetrazolyl,
(4) —hydroxyisoxazole,
(5) —SO$_2$NHCO—R$^9$ or —SO$_2$NHCO—(C$_{1-3}$ alkyl)—R$^9$,
(6) —P(O)(OH)$_2$;

$R^2$ is selected from:
(1) hydrogen, and
(2) hydroxy;

$R^3$ is selected from the group consisting of:
phenyl and thienyl, which is unsubstituted or substituted with 1–7 substituents where the substituents are independently selected from:
(a) halo,
(b) trifluoromethyl,
(c) hydroxy,
(d) $C_{1-3}$ alkyl,
(e) —O—$C_{1-3}$ alkyl,
(f) —CO$_2$R$^9$,
(g) —NR$^9$R$^{10}$, and
(h) —CONR$^9$R$^{10}$;

$R^4$ and $R^5$ are independently selected from:
hydrogen, hydroxy, fluoro, $C_{1-10}$ alkyl, $C_{3-8}$ cycloalkyl, $C_{2-10}$ alkenyl, $C_{2-10}$ alkynyl, phenyl, —(C$_{1-6}$ alkyl)-phenyl, —(C$_{1-6}$ alkyl)—C$_{3-8}$ cycloalkyl, naphthyl, and biphenyl, which is unsubstituted or substituted with 1–7 of $R^{11}$ where $R^{11}$ is independently selected from:
(a) halo,
(b) trifluoromethyl,
(c) hydroxy,
(d) $C_{1-3}$ alkyl,
(e) —O—$C_{1-3}$ alkyl,
(f) —CO$_2$R$^9$, and
(g) —CONR$^9$R$^{10}$, or where $R^4$ and $R^5$ are joined together to form a 3–8 membered saturated ring which is unsubstituted or substituted with 1–7 of $R^{11}$, or where, if n is 1, $R^2$ and $R^4$ are joined together to form a double bond;

$R^7$ is selected from:
(1) hydrogen,
(2) $C_{1-6}$ alkyl, which is unsubstituted or substituted with 1–4 substituents where the substituents are independently selected from: hydroxy, cyano, and halo,
(3) hydroxy, and
(4) halo;

$R^8$ is selected from:
hydrogen, phenyl, naphthyl, and biphenyl, which is unsubstituted or substituted with 1–7 of $R^{12}$ where $R^{12}$ is independently selected from:
(a) halo,
(b) cyano,
(c) hydroxy,
(d) $C_{1-6}$ alkyl, which is unsubstituted or substituted with 1–5 of $R^{13}$ where $R^{13}$ is independently selected from: halo, cyano, hydroxy, $C_{1-6}$ alkoxy, —CO$_2$H, —CO$_2$(C$_{1-6}$ alkyl), phenyl, trifluoromethyl, and —NR$^9$R$^{10}$,
(e) —O—$C_{1-6}$ alkyl, which is unsubstituted or substituted with 1–5 of $R^{13}$,
(f) —CF$_3$,
(g) —CHF$_2$,
(h) —CH$_2$F,
(i) —NO$_2$,
(j) phenyl,
(k) —CO$_2$R$^9$,
(l) tetrazolyl,
(m) —NR$^9$R$^{10}$,
(n) —NR$^9$—COR$^{10}$,
(o) —NR$^9$—CO$_2$R$^{10}$,
(p) —CO—NR$^9$R$^{10}$,
(q) —OCO—NR$^9$R$^{10}$,
(r) —NR$^9$CO—NR$^9$R$^{10}$,
(s) —S(O)$_m$—R$^9$, wherein m is an integer selected from 0, 1 and 2,
(t) —S(O)$_2$—NR$^9$R$^{10}$,
(u) —NR$^9$S(O)$_2$—R$^{10}$, and
(v) —NR$^9$S(O)$_2$—NR$^9$R$^{10}$;

n is an integer selected from 1, 2, 3 and 4;

x is an integer selected from 0, 1 and 2, and y is an integer selected from 0, 1 and 2, with the proviso that the sum of x and y is 2;

or a pharmaceutically acceptable salt thereof or an individual diastereomer thereof.

2. A compound of claim 1, wherein $R^1$ is selected from:
(1) —CO$_2$H,
(2) —NO$_2$,
(3) —tetrazolyl,
(4) —hydroxyisoxazole, and
(5) —P(O)(OH)$_2$;

or a pharmaceutically acceptable salts thereof or an individual diastereomer thereof.

3. A compound of claim 1, wherein $R^1$ is selected from:
(1) —CO$_2$H, and
(2) —tetrazolyl;

or a pharmaceutically acceptable salts thereof or an individual diastereomer thereof.

4. A compound of claim 3, wherein $R^1$ is —CO$_2$H;
or a pharmaceutically acceptable salts thereof or an individual diastereomer thereof.

5. A compound of claim 1, wherein $R^3$ is selected from the group consisting of:
phenyl and thienyl, which may be unsubstituted or substituted with 1–5 substituents where the substituents are independently selected from:
(a) halo,
(b) trifluoromethyl,
(c) hydroxy,
(d) $C_{1-3}$ alkyl, and
(e) —O—$C_{1-3}$ alkyl;

or a pharmaceutically acceptable salts thereof or an individual diastereomer thereof.

6. A compound of claim 5, wherein $R^3$ is selected from the group consisting of:
phenyl, which may be unsubstituted or substituted with 1–5 substituents where the substituents are independently selected from:
(a) fluoro, and
(b) chloro; and
unsubstituted thienyl;

or a pharmaceutically acceptable salts thereof or an individual diastereomer thereof.

7. A compound of claim 6, wherein $R^3$ is unsubstituted phenyl, (3-fluoro)phenyl or 3-thienyl;
or a pharmaceutically acceptable salts thereof or an individual diastereomer thereof.

8. A compound of claim 1, wherein $R^2$ is hydrogen;
or a pharmaceutically acceptable salts thereof or an individual diastereomer thereof.

9. A compound of claim 1, wherein $R^4$ is hydrogen or $C_{1-6}$ alkyl;
or a pharmaceutically acceptable salts thereof or an individual diastereomer thereof.

10. A compound of claim 1, wherein $R^5$ is selected from: hydrogen, methyl, n-propyl, isopropyl, n-butyl, isobutyl, secbutyl, cyclohexyl, —$CH_2$—cyclopropyl, —$CH_2$-cyclobutyl and phenyl;
or a pharmaceutically acceptable salts thereof or an individual diastereomer thereof.

11. A compound of claim 1, wherein $R^7$ is hydrogen, fluoro, hydroxy or $C_{1-6}$ alkyl;
or a pharmaceutically acceptable salts thereof or an individual diastereomer thereof.

12. A compound of claim 11, wherein $R^7$ is hydrogen;
or a pharmaceutically acceptable salts thereof or an individual diastereomer thereof.

13. A compound of claim 1, wherein X is: —Y— or —Y—($C_{1-4}$ alkyl)—,
where the alkyl is unsubstituted,
where Y is selected from:
—O(CO)$NR^9$—, —$NR^9$(CO)O—, and —$NR^9$(CO)$NR^{10}$—,
where $R^9$ is independently selected from: hydrogen, $C_{1-10}$ alkyl, $C_{2-10}$ alkenyl, and $C_{1-6}$ alkyl-$C_{3-6}$ cycloalkyl,
where $R^{10}$ is independently selected from: hydrogen and $C_{1-6}$ alkyl,
or where $R^9$ and $R^{10}$ are joined together to form a 5–8 membered ring consisting of the —N(CO)N— functional group and a balance of carbon atoms, wherein the ring is unsubstituted;
or a pharmaceutically acceptable salts thereof or an individual diastereomer thereof.

14. A compound of claim 13, wherein X is selected from:
—$NR^9$(CO)O—, —$NR^9$(CO)$OCH_2$—, —$NR^9$(CO)NH—, and —$NR^9$(CO)$NHCH_2$—,
where $R^9$ is independently selected from: methyl, ethyl, n-propyl, allyl, and —$CH_2$-cyclopropyl;
or a pharmaceutically acceptable salts thereof or an individual diastereomer thereof.

15. A compound of claim 1, wherein $R^8$ is phenyl which is unsubstituted or substituted with 1–5 substituents where the substituents are independently selected from:
(a) halo,
(b) cyano,
(c) —$NO_2$,
(d) —$CF_3$,
(e) —$CHF_2$,
(f) —$CH_2F$,
(g) tetrazolyl,
(h) $C_{1-6}$ alkyl, which is unsubstituted or substituted with phenyl, and
(i) —O—$C_{1-6}$ alkyl;
or a pharmaceutically acceptable salts thereof or an individual diastereomer thereof.

16. A compound of claim 15, wherein $R^8$ is selected from:

phenyl, 4-chlorophenyl, 2-fluorophenyl, 3-fluorophenyl, 4-fluorophenyl, 2,4-difluorophenyl, 3,4-difluorophenyl, 3,5-difluorophenyl, 4-methylphenyl, 3-nitrophenyl, 4-nitrophenyl, and 4-trifluoromethylphenyl;

or a pharmaceutically acceptable salts thereof or an individual diastereomer thereof.

17. A compound of claim 1, wherein n is an integer which is 1;
or a pharmaceutically acceptable salts thereof or an individual diastereomer thereof.

18. A compound of claim 1, wherein x is an integer which is 1 and y is an integer which is 1;
or a pharmaceutically acceptable salts thereof or an individual diastereomer thereof.

19. A compound of claim 1, wherein the compound which is selected from the group consisting of:

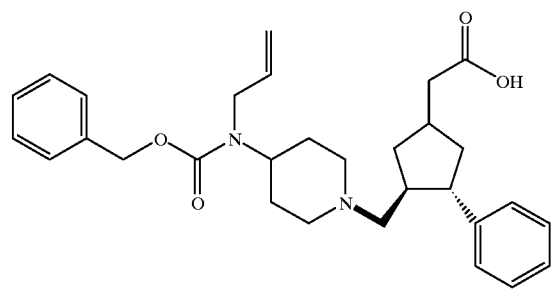

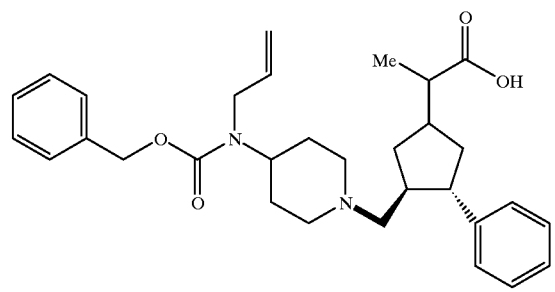

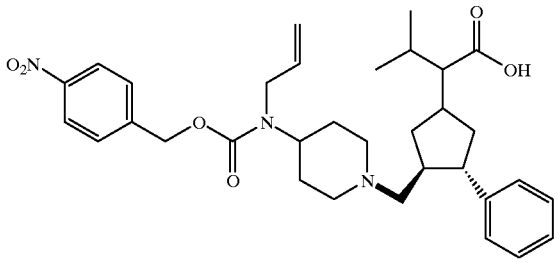

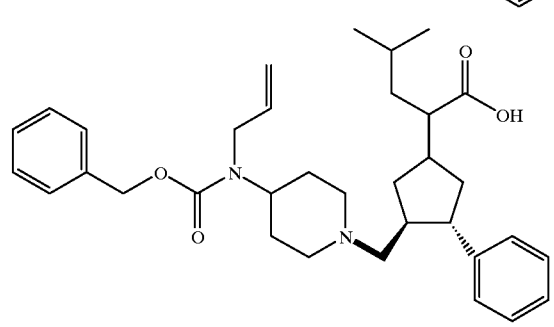

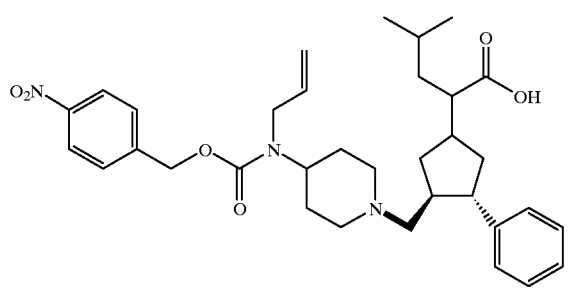
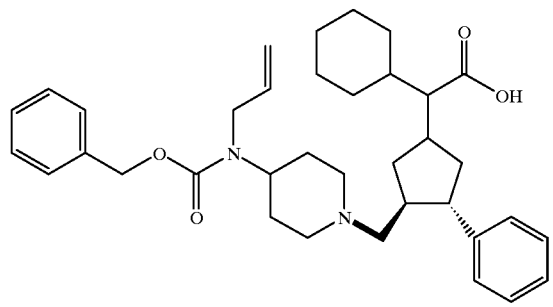
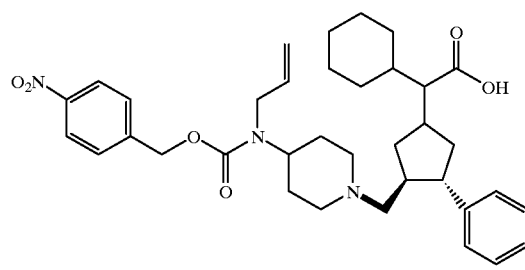
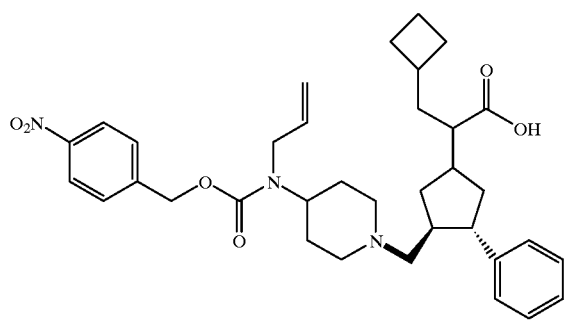
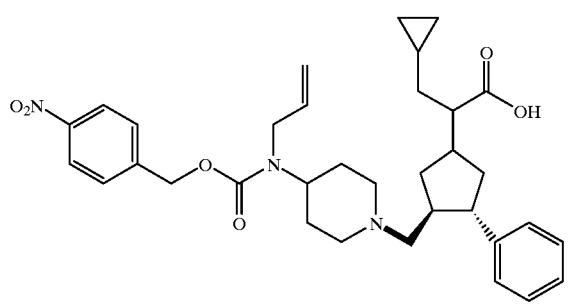
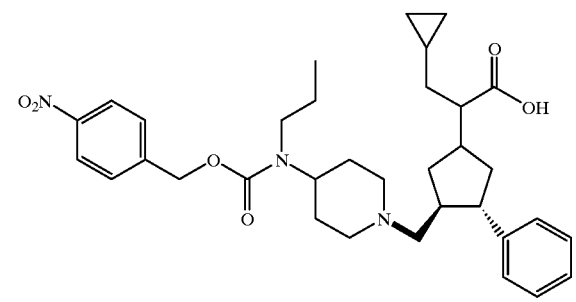
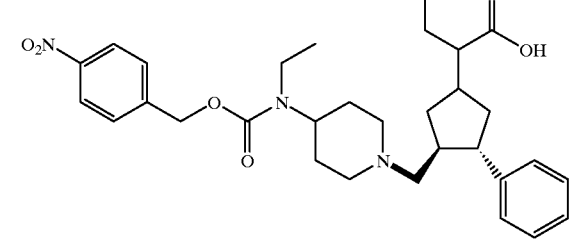
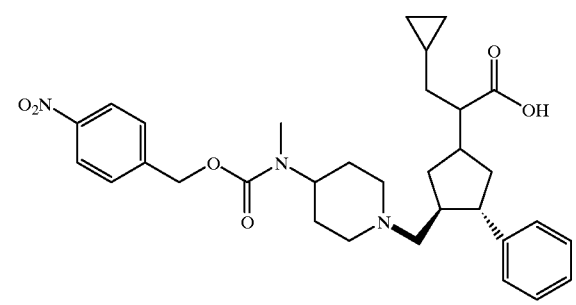
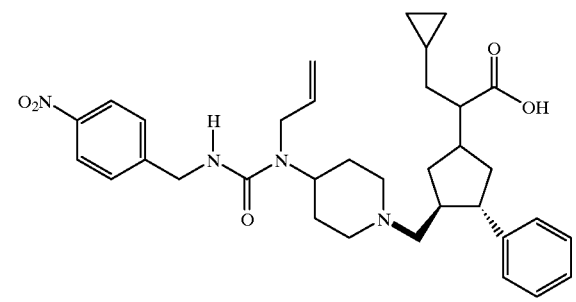
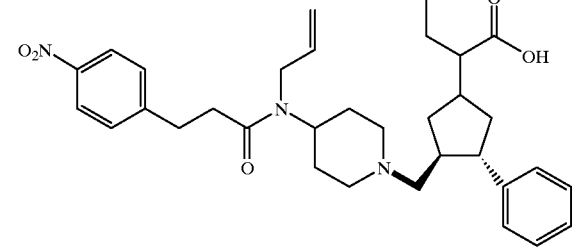

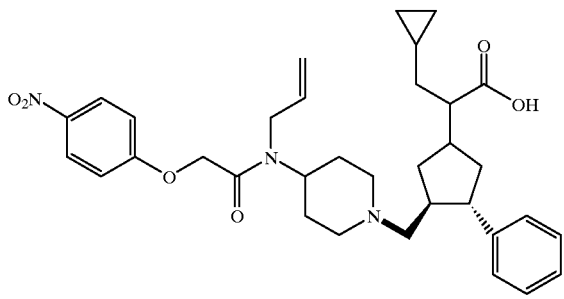

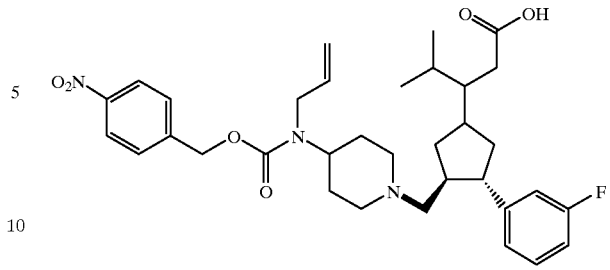

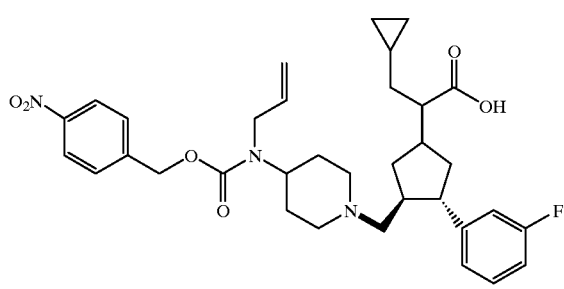

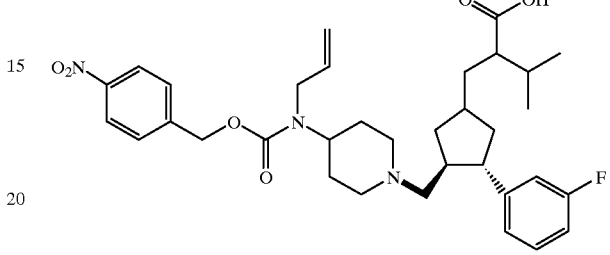

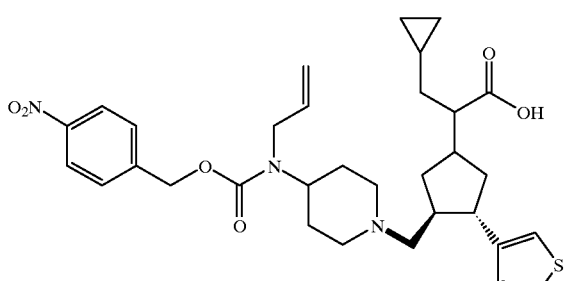

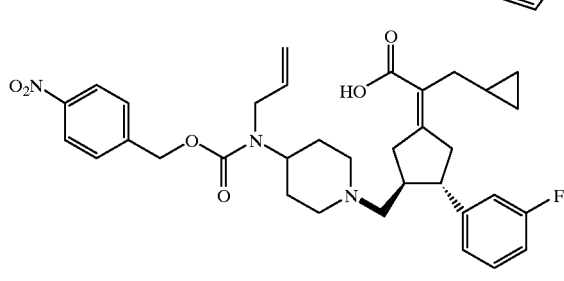

or a pharmaceutically acceptable salts thereof or an individual diastereomer thereof.

20. A pharmaceutical composition which comprises an inert carrier and a compound of claim 1 or a pharmaceutically acceptable salt thereof or an individual diastereomer thereof.

21. A method for modulation of CCR-3 or CCR-5 chemokine receptor activity in a mammal in need thereof to treat asthma, allergic rhinitis, dermatitis, conjunctivitis, atherosclerosis or rheumatoid arthritis, which comprises the administration of an effective amount of the compound of claim 1 or a pharmaceutically acceptable salt thereof or an individual diastereomer thereof.

22. A method for treating infection by HIV, delaying of the onset of AIDS, or treating AIDS comprising the administration to a patient of an effective amount of the compound of claim 1 or a pharmaceutically acceptable salt thereof or an individual diastereomer thereof.

23. A method for the treatment of an inflammatory and immunoregulatory disorder or disease which comprises the administration to a patient of an effective amount of the compound of claim 1.

* * * * *